US012618051B2

(12) United States Patent
Li et al.

(10) Patent No.:  US 12,618,051 B2
(45) Date of Patent:  May 5, 2026

(54) ENGINEERED ALPHA-1,3 BRANCHING ENZYMES

(71) Applicant: NUTRITION & BIOSCIENCES USA 4, INC., Rochester, NY (US)

(72) Inventors: Yougen Li, Glen Mills, PA (US); Ellen D. Semke, Newark, DE (US)

(73) Assignee: NUTRITION & BIOSCIENCES USA 4, INC., Wilmington, DE (US)

( * ) Notice: Subject to any disclaimer, the term of this patent is extended or adjusted under 35 U.S.C. 154(b) by 1035 days.

(21) Appl. No.: 17/625,136

(22) PCT Filed: Jul. 8, 2020

(86) PCT No.: PCT/US2020/041093

§ 371 (c)(1),
(2) Date: Jan. 6, 2022

(87) PCT Pub. No.: WO2021/007264

PCT Pub. Date: Jan. 14, 2021

(65) Prior Publication Data

US 2022/0267745 A1      Aug. 25, 2022

Related U.S. Application Data

(60) Provisional application No. 62/871,796, filed on Jul. 9, 2019.

(51) Int. Cl.
*C12N 9/10*         (2006.01)
*C12P 19/18*        (2006.01)

(52) U.S. Cl.
CPC ............ *C12N 9/1051* (2013.01); *C12P 19/18* (2013.01)

(58) Field of Classification Search
CPC ....... C12N 9/1051; C12N 15/10; C12P 19/18; C12P 19/08
See application file for complete search history.

(56) References Cited

U.S. PATENT DOCUMENTS

| | | | |
|---|---|---|---|
| 10,301,604 B2 * | 5/2019 | Li | C12N 9/1051 |
| 10,774,315 B2 * | 9/2020 | Li | C12N 9/1048 |
| 11,028,373 B2 * | 6/2021 | Li | C12N 9/1051 |
| 11,104,747 B2 * | 8/2021 | Behabtu | A61P 17/02 |
| 11,198,853 B2 * | 12/2021 | Li | C12P 19/18 |
| 11,261,264 B2 * | 3/2022 | Cheng | A23L 7/126 |
| 11,390,692 B2 * | 7/2022 | Nambiar | C12P 19/08 |
| 11,535,683 B2 * | 12/2022 | Paullin | C12N 9/1048 |
| 11,560,551 B2 * | 1/2023 | Li | C12N 9/1051 |
| 11,685,907 B2 * | 6/2023 | Nagy | C12P 19/04 435/101 |
| 11,952,598 B2 * | 4/2024 | Li | C12P 19/18 |
| 12,037,420 B2 * | 7/2024 | Behabtu | C08B 37/0021 |
| 12,110,347 B2 * | 10/2024 | Cheng | C12Y 204/01002 |
| 12,173,091 B2 * | 12/2024 | Nambiar | C08B 37/0021 |
| 12,188,055 B2 * | 1/2025 | Li | C12N 9/1051 |
| 2016/0122445 A1 | 5/2016 | Nambiar et al. | |
| 2016/0136199 A1 | 5/2016 | Remaud-Simeon et al. | |
| 2017/0218093 A1 | 8/2017 | Cheng et al. | |
| 2018/0072998 A1 * | 3/2018 | Li | C12P 19/04 |
| 2018/0104274 A1 * | 4/2018 | Remaud-Simeon | C08L 5/02 |
| 2018/0282385 A1 | 10/2018 | Cheng et al. | |
| 2020/0165360 A1 | 5/2020 | Behabtu et al. | |

FOREIGN PATENT DOCUMENTS

| | | | | |
|---|---|---|---|---|
| FR | 3007038 A1 * | 12/2014 | ............. | C12P 19/18 |
| KR | 20040092250 A | 11/2004 | | |
| WO | 2015119859 A1 | 8/2015 | | |
| WO | 2016205391 A1 | 12/2016 | | |
| WO | 2017079595 A1 | 5/2017 | | |
| WO | 2018052942 A1 | 3/2018 | | |
| WO | 2019007999 A1 | 1/2019 | | |
| WO | 2019055373 A1 | 3/2019 | | |

OTHER PUBLICATIONS

GenPept Accession No. WP_036061154.1 (2 pages, Dec. 24, 2014) (Year: 2014).*
GenBank Accession No. AAB40875.1 (2 pages, Jan. 15, 1997) (Year: 1997).*
Monchois et al. (Gene, 1996, 182:23) (Year: 1996).*
NCBI Accession No. WP_002884027.1 (2 pages, May 6, 2013) (Year: 2013).*
NCBI Accession No. WP_010006776.1 (2 pages, Jun. 6, 2013) (Year: 2013).*
Machine translation of FR 3007038 A1 (9 pages, Dec. 15, 2025) (Year: 2025).*
Vuillemin et al. (2016, J. Biol. Chem. 14:7687-7702).
International Preliminary Report on Patentability for PCT/US2020/041093 issued Jan. 11, 2022.

* cited by examiner

*Primary Examiner* — David Steadman
*Assistant Examiner* — Joseph R Spangler

(57)          ABSTRACT

Disclosed herein are glucosyltransferases with modified amino acid sequences. Such engineered enzymes have modified alpha-1,3-branching activity. Further disclosed are reactions and methods in which engineered glucosyltransferases can be used to add one or more alpha-1,3 branches to a suitable acceptor such as glucan.

18 Claims, No Drawings

Specification includes a Sequence Listing.

SEQUENCE LISTING

<160> NUMBER OF SEQ ID NOS: 15

<210> SEQ ID NO 1
<211> LENGTH: 5229
<212> TYPE: DNA
<213> ORGANISM: Artificial sequence
<220> FEATURE:
<223> OTHER INFORMATION: encoding GTF 2592, truncated, w/ added start
      methionine and C-terminal 6xHis tag

<400> SEQUENCE: 1

```
atgacaactg tagcaagtgc tgatgtacaa aaggatacag tagttgttac tgcagataaa        60
aatactactg ataaggacaa agaaccgatt aagacagcgg gagcaaatgt tgttgataag       120
ggagttgccc agacaacgga cacaaatact actgataaaa agacgataga agtaggtaag       180
tcagtagaca tgagtgctac tgataagaaa gtgacagaaa cagttaaatc agtggacacg       240
agtgctactg ataaaaagac aacagaagct gttaaaccag tagatacgaa tgctactgat       300
aagaaagcaa cagaagcagt taagccagta gatacgaatg ctactgataa gaagacgaca       360
gaagcagtta agccagtaga cacaaatact actgataaga aagtaacaga agcaattaag       420
ccagtaaaca caaatgctga tgataagaca gcagagcctg ttaagacaat atcagcaacc       480
```

-continued

```
aaagataccg ttaaaaccat agctaataag caaaaggggg caactgaaga gcaagcagtt    540
attactgaag ggcattacga agcccaaggt gatggttttg tttatattac taaagatggt    600
aaacaattaa cgggattaca gaatattaat ggtaatactc aatactttga tcctgcaaca    660
ggacaacagc tgaagggcga tattaaagca gttgcaggca cagtctatta ctttgataaa    720
aatagcggta atgcacgcgt ataccaaaaa gtagcagatg gtacttattc agagaataat    780
gagcattggc aatatatcag taaagtagat aataagccgg ttgagggctt atataatgta    840
caaggtaacc tacaatactt tgatatgtcc actggaaatc aagtaaaaaa tgatattcgc    900
tctgtggacg gcgtcactta ctattttgac aaagatagtg gtaatggatc agcatttaat    960
gcattatcag ctggtgaata cgttgaaaag aaggagacgg acgcacaagg caatcagaac    1020
tcatattgga catatagtgg attagatggt aatccggtta aaggattgta tgatattaac    1080
ggttcactac aatattttga tgaaaagaat ggtgcacagt aaaaggtgg aacagccaca    1140 gtcaatggcg taacatatta ttttgaacaa gataagggta acctgattag tgttgttaat    1200
agtgttgaga gtggtcaata taaaattgat aatgacaacg tttattatat tgacaatcaa    1260
ggtaacacgt taaaaggtct atatgctatt aatggacaat aaaattattt tgacatgagc    1320
actggtgttc aactaaaagg tgctagtgag aatgctaatg gtgtcggtta ttacttcgat    1380
aaagataagg gtaatggtca gtatcaatat agtttgatta cttcgacact tgctaatgca    1440
ttttcaaaac ataatgcagc taatgattac actcagagta gtttttactca tactgttgat    1500 ggcttttttga cagctgatac gtggtaccga ccaacagaga tactcaaaaa tggaacgaca    1560
tgggttgctt caacatcaca ggatttgaga ccaatgatta ctgtttggtg gcctaataaa    1620
aatgtacagc ttaactatct taaacttatg caaacagaag ggttgttgga tagtggccaa    1680
gtatatgatt tgaatagcga tcaagcactg ctcaatcaag cagcacaaac ggtgcaagtg    1740
aacattgaaa aaaggataac taaagcagga aattctgatt ggcttaatga tttgctatat    1800
aacagtcacg gtgaaacacc ttcgtttgtt aagcagcagg ctatttggaa tgctgattct    1860
gaatatcatg gcggttggtt ccagggtgga tatttagcat atcggaatag tgatttaaca    1920
ccatatgcga attcatcata cagacattac accggaatgg aattttttgtt ggctaatgat    1980 gttgataatt ccaatccaat tgtacaagct gaagacctta actggttata ctatctaatg    2040
aattttggaa cggaaacagg caatgatccg caagccaatt ttgatagtat ccgtattgat    2100
gctattagct ttgtcgacaa acaagtggct aagaaagcat atgaattact tcatgatatg    2160
tatggcttat cagctagtga cgctgtagca aataagcatg tttctattgt agaagcaagt    2220
gccgatcaga caccagttac gacagaaaat catgatgcat taattgagtc ttactggcgt    2280
gacactatga aaaattcatt gtccaaagat gcgtcaattg attcatctgc tggatcgtta    2340
tctgcaatga taaatgatgg aaatgttgat cgtgctaacg atagtactac agaaagttca    2400
atattcccaa actatacaat tgttcatgcg catgataaag atatacaaga tgctgtaagc    2460
aatgttatga aaattgtaaa taatgatcca tccatttcac tagatggttt tacaatggaa    2520
cagttagaga agggattgtc agcattttat gctgatcaga gatctgctgt taagcaatat    2580
aatcaatata atattccaag tgcttatgcg gttatgttaa ctaacaaaga tactgtgcca    2640
cgtacatttt atggtgatat gtatcaagat gatggtcaat atatggctaa taagtcacta    2700
tactatgatg ctattgatac aatgatgaag gctcgcctga aatatgtttc cggtggtcaa    2760
actatgtctg ttacaaaaat caataatgca aatagtcaga aatctggaga agtattaaca    2820
```

-continued

```
agcgttcgtt ttggaaaagg tgttatggat gctacagatg ccggaagtgc tgaaagtaga    2880
acacaaggca ttggtgtggt tgtgtctaat agtagcggtc ttcaattgaa cgataatgat    2940
aaaattgtgt tacatatggg tgcggcgcat aaaaaccaag aataccgtgc attaatgtta    3000
acaactaatg atggtattaa atcctttaat aacgatgaag caccaattaa ttatactgat    3060
gataatggtg atttaatttt tgatggacac aatattgatg gtcaagagaa tacagcaatc    3120
agaggttatc ttaatccgca agttgctgga tatttagcgg tatgggtacc aactggtgct    3180
aaagatgatc aagatgctag aacacaacct tccaatgaaa aatctactga tggcaaagta    3240
ttacacacaa atgctgcttt ggattctgaa ttgatttatg aaggattttc taacttccaa    3300
cccatgccaa caactaaaga tgaatatacg aatgtgatga ttgctaaaaa tattgatctc    3360
tttaagtcat ggggtatcac taattttgaa ttagcaccac aatatcgatc aagcgatggc    3420
aaaaatatta atgatcgttt tattgattca cttgttcaga atggttatgg tttgagcgac    3480
cgatacgatc ttgggtttga gacgccaact aaatatggta cagatcaaga tttgagaaca    3540
gcgattaaaa cattcacacca agccggtatg actgtcatgg ctgactatgt tgctaaccaa    3600
atttatggat tgaatacaag tcaagaagtg gttgatgcgc aacgagttaa ttcggataat    3660
aatgcagtcg aagttcgcta cggtcagcat ttgaatgttg taaactcaat tggggggcggt    3720 gaatatcaga atttgtatgg tggaaaatac ctagaaattt tgaataaact ttatcctgat    3780
ctgctggtcg atgagaatgg taataaaata gatattgata ccaaaatcaa acaatggtct    3840
gctaaatatc ttaacggcag taatgtaacc ggactcggta tggggtatgt tctaaaagat    3900
tggtcaaatg gacaatactt taatatttct aatactgatg gcaaagttat gttgccagaa    3960
cagttagtta aacatatgcc tgccgtagaa attggtacgc aaacgaatta tacggcgtat    4020
atttcaagta caattcgtcg tgatggtctt tataacaata tgccatgggg tgtcactgct    4080
acaggacaag atggcaacga gataaagtgg gaacgtcaag gtagtacgtc tgattataat    4140
caccagaagg tacaagtaaa ccgacagtat gttgataagc aaggtgttgt ttggaactta    4200
attaattttg atgataaaga tctatgggtt gatagtaatg cactcgtaac ggttaacttt    4260
acatcacaaa agccaactaa gcattttgtc caattcggta tgcgtcaagg taagtatgat    4320
ggcttctatc ttagtgcacc atataagcaa actgagtcaa agtgggttgc ttctacacga    4380
acacatcaag gacaattatt ggaagttgtc ggtcaatata caacagggtc aggtagtcgt    4440
aaggtaactt ggtacttggt tggtcttgat ggtaagcaag tatgggtaga cagtcgagct    4500
gttggtacta atttcagtca taagacaaat attaatttgt tgattaatag tgccacacgc    4560
aatgatggta tgtacttgaa tgcaccgtat ggtcagaagg gttataagcg agaaacatca    4620
agtcgcttct ataatgaaaa gctcgtaaca gttagtcaac aatattacga taataagggt    4680
gttatttgga accttattac tttgaatggt aaaaagctgt gggtagatag ccgagcattt    4740
gcaacagtta ttgataagaa agtgaaccaa agcctgtata tcaatagtcg taatgatggt    4800
atgtacttga atgcaccata tcgtgcacaa ggtgctaaac gatatgcttc aacgaagaca    4860
tatacagggc aacgtgtgca agtgacatta caacgtaaag atactcacgg tgtaacttgg    4920
tatctcacta aggtagatag taagcagttg tgggtagaca gccatgcatt tgcaccaacc    4980
ttcacgcgta atgtgtcgct caatgttaaa gtgaacagtt caaaacgtaa tgatgggatt    5040
tacttaaacg caccatatgg caataaaaaa gccaagcgta ttgcatcaac aaaggcatac    5100
aatggtaagc gtgtaaaagc tagtaaagaa tataaagatg ctaaggggagt aacttggtat    5160 ttggtaaacc ttaataataa acaagtgtgg attgacaaac gtgcatttca ccatcaccac    5220
```

-continued catcactaa                                                                5229

<210> SEQ ID NO 2
<211> LENGTH: 1742
<212> TYPE: PRT
<213> ORGANISM: Artificial sequence
<220> FEATURE:
<223> OTHER INFORMATION: GTF 2592, truncated, w/ added start methionine
      and C-terminal 6xHis tag

<400> SEQUENCE: 2

Met Thr Thr Val Ala Ser Ala Asp Val Gln Lys Asp Thr Val Val Val
1               5                   10                  15

Thr Ala Asp Lys Asn Thr Thr Asp Lys Asp Lys Glu Pro Ile Lys Thr
                20                  25                  30

Ala Gly Ala Asn Val Val Asp Lys Gly Val Ala Gln Thr Thr Asp Thr
            35                  40                  45

Asn Thr Thr Asp Lys Lys Thr Ile Glu Val Gly Lys Ser Val Asp Met
    50                  55                  60

Ser Ala Thr Asp Lys Lys Val Thr Glu Thr Val Lys Ser Val Asp Thr
65                  70                  75                  80

Ser Ala Thr Asp Lys Lys Thr Thr Glu Ala Val Lys Pro Val Asp Thr
                85                  90                  95

Asn Ala Thr Asp Lys Lys Ala Thr Glu Ala Val Lys Pro Val Asp Thr
                100                 105                 110

Asn Ala Thr Asp Lys Lys Thr Thr Glu Ala Val Lys Pro Val Asp Thr
            115                 120                 125

Asn Thr Thr Asp Lys Lys Val Thr Glu Ala Ile Lys Pro Val Asn Thr
    130                 135                 140

Asn Ala Asp Asp Lys Thr Ala Glu Pro Val Lys Thr Ile Ser Ala Thr
145                 150                 155                 160

Lys Asp Thr Val Lys Thr Ile Ala Asn Lys Gln Lys Gly Ala Thr Glu
                165                 170                 175

Glu Gln Ala Val Ile Thr Glu Gly His Tyr Glu Ala Gln Gly Asp Gly
            180                 185                 190

Phe Val Tyr Ile Thr Lys Asp Gly Lys Gln Leu Thr Gly Leu Gln Asn
            195                 200                 205

Ile Asn Gly Asn Thr Gln Tyr Phe Asp Pro Ala Thr Gly Gln Gln Leu
    210                 215                 220

Lys Gly Asp Ile Lys Ala Val Ala Gly Thr Val Tyr Tyr Phe Asp Lys
225                 230                 235                 240

Asn Ser Gly Asn Ala Arg Val Tyr Gln Lys Val Ala Asp Gly Thr Tyr
                245                 250                 255

Ser Glu Asn Asn Glu His Trp Gln Tyr Ile Ser Lys Val Asp Asn Lys
                260                 265                 270

Pro Val Glu Gly Leu Tyr Asn Val Gln Gly Asn Leu Gln Tyr Phe Asp
                275                 280                 285

Met Ser Thr Gly Asn Gln Val Lys Asn Asp Ile Arg Ser Val Asp Gly
    290                 295                 300

Val Thr Tyr Tyr Phe Asp Lys Asp Ser Gly Asn Gly Ser Ala Phe Asn
305                 310                 315                 320

Ala Leu Ser Ala Gly Glu Tyr Val Glu Lys Lys Glu Thr Asp Ala Gln
            325                 330                 335

Gly Asn Gln Asn Ser Tyr Trp Thr Tyr Ser Gly Leu Asp Gly Asn Pro
            340                 345                 350

-continued

```
Val Lys Gly Leu Tyr Asp Ile Asn Gly Ser Leu Gln Tyr Phe Asp Glu
        355                 360                 365

Lys Asn Gly Ala Gln Leu Lys Gly Gly Thr Ala Thr Val Asn Gly Val
        370                 375                 380

Thr Tyr Tyr Phe Glu Gln Asp Lys Gly Asn Leu Ile Ser Val Val Asn
385                 390                 395                 400

Ser Val Glu Ser Gly Gln Tyr Lys Ile Asp Asn Asp Asn Val Tyr Tyr
                405                 410                 415

Ile Asp Asn Gln Gly Asn Thr Leu Lys Gly Leu Tyr Ala Ile Asn Gly
                420                 425                 430

Gln Leu Asn Tyr Phe Asp Met Ser Thr Gly Val Gln Leu Lys Gly Ala
        435                 440                 445

Ser Glu Asn Ala Asn Gly Val Gly Tyr Tyr Phe Asp Lys Asp Lys Gly
        450                 455                 460

Asn Gly Gln Tyr Gln Tyr Ser Leu Ile Thr Ser Thr Leu Ala Asn Ala
465                 470                 475                 480

Phe Ser Lys His Asn Ala Ala Asn Asp Tyr Thr Gln Ser Ser Phe Thr
                485                 490                 495

His Thr Val Asp Gly Phe Leu Thr Ala Asp Thr Trp Tyr Arg Pro Thr
        500                 505                 510

Glu Ile Leu Lys Asn Gly Thr Thr Trp Val Ala Ser Thr Ser Gln Asp
        515                 520                 525

Leu Arg Pro Met Ile Thr Val Trp Trp Pro Asn Lys Asn Val Gln Leu
        530                 535                 540

Asn Tyr Leu Lys Leu Met Gln Thr Glu Gly Leu Leu Asp Ser Gly Gln
545                 550                 555                 560

Val Tyr Asp Leu Asn Ser Asp Gln Ala Leu Leu Asn Gln Ala Ala Gln
                565                 570                 575

Thr Val Gln Val Asn Ile Glu Lys Arg Ile Thr Lys Ala Gly Asn Ser
                580                 585                 590

Asp Trp Leu Asn Asp Leu Leu Tyr Asn Ser His Gly Glu Thr Pro Ser
        595                 600                 605

Phe Val Lys Gln Gln Ala Ile Trp Asn Ala Asp Ser Glu Tyr His Gly
        610                 615                 620

Gly Trp Phe Gln Gly Gly Tyr Leu Ala Tyr Arg Asn Ser Asp Leu Thr
625                 630                 635                 640

Pro Tyr Ala Asn Ser Ser Tyr Arg His Tyr Thr Gly Met Glu Phe Leu
                645                 650                 655

Leu Ala Asn Asp Val Asp Asn Ser Asn Pro Ile Val Gln Ala Glu Asp
                660                 665                 670

Leu Asn Trp Leu Tyr Tyr Leu Met Asn Phe Gly Thr Glu Thr Gly Asn
        675                 680                 685

Asp Pro Gln Ala Asn Phe Asp Ser Ile Arg Ile Asp Ala Ile Ser Phe
        690                 695                 700

Val Asp Lys Gln Val Ala Lys Lys Ala Tyr Glu Leu Leu His Asp Met
705                 710                 715                 720

Tyr Gly Leu Ser Ala Ser Asp Ala Val Ala Asn Lys His Val Ser Ile
                725                 730                 735

Val Glu Ala Ser Ala Asp Gln Thr Pro Val Thr Thr Glu Asn His Asp
                740                 745                 750

Ala Leu Ile Glu Ser Tyr Trp Arg Asp Thr Met Lys Asn Ser Leu Ser
        755                 760                 765
```

```
Lys Asp Ala Ser Ile Asp Ser Ser Ala Gly Ser Leu Ser Ala Met Ile
770             775                 780

Asn Asp Gly Asn Val Asp Arg Ala Asn Asp Ser Thr Thr Glu Ser Ser
785                 790                 795                 800

Ile Phe Pro Asn Tyr Thr Ile Val His Ala His Asp Lys Asp Ile Gln
                805             810             815

Asp Ala Val Ser Asn Val Met Lys Ile Val Asn Asn Asp Pro Ser Ile
            820             825             830

Ser Leu Asp Gly Phe Thr Met Glu Gln Leu Glu Lys Gly Leu Ser Ala
        835             840             845

Phe Tyr Ala Asp Gln Arg Ser Ala Val Lys Gln Tyr Asn Gln Tyr Asn
    850             855             860

Ile Pro Ser Ala Tyr Ala Val Met Leu Thr Asn Lys Asp Thr Val Pro
865             870             875             880

Arg Thr Phe Tyr Gly Asp Met Tyr Gln Asp Asp Gly Gln Tyr Met Ala
            885             890             895

Asn Lys Ser Leu Tyr Tyr Asp Ala Ile Asp Thr Met Met Lys Ala Arg
        900             905             910

Leu Lys Tyr Val Ser Gly Gly Gln Thr Met Ser Val Thr Lys Ile Asn
    915             920             925

Asn Ala Asn Ser Gln Lys Ser Gly Glu Val Leu Thr Ser Val Arg Phe
    930             935             940

Gly Lys Gly Val Met Asp Ala Thr Asp Ala Gly Ser Ala Glu Ser Arg
945             950             955             960

Thr Gln Gly Ile Gly Val Val Val Ser Asn Ser Ser Gly Leu Gln Leu
            965             970             975

Asn Asp Asn Asp Lys Ile Val Leu His Met Gly Ala Ala His Lys Asn
            980             985             990

Gln Glu Tyr Arg Ala Leu Met Leu  Thr Thr Asn Asp Gly  Ile Lys Ser
        995             1000                1005

Phe Asn  Asn Asp Glu Ala Pro  Ile Asn Tyr Thr Asp  Asp Asn Gly
    1010            1015                1020

Asp Leu  Ile Phe Asp Gly His  Asn Ile Asp Gly Gln  Glu Asn Thr
    1025            1030                1035

Ala Ile  Arg Gly Tyr Leu Asn  Pro Gln Val Ala Gly  Tyr Leu Ala
    1040            1045                1050

Val Trp  Val Pro Thr Gly Ala  Lys Asp Asp Gln Asp  Ala Arg Thr
    1055            1060                1065

Gln Pro  Ser Asn Glu Lys Ser  Thr Asp Gly Lys Val  Leu His Thr
    1070            1075                1080

Asn Ala  Ala Leu Asp Ser Glu  Leu Ile Tyr Glu Gly  Phe Ser Asn
    1085            1090                1095

Phe Gln  Pro Met Pro Thr Thr  Lys Asp Glu Tyr Thr  Asn Val Met
    1100            1105                1110

Ile Ala  Lys Asn Ile Asp Leu  Phe Lys Ser Trp Gly  Ile Thr Asn
    1115            1120                1125

Phe Glu  Leu Ala Pro Gln Tyr  Arg Ser Ser Asp Gly  Lys Asn Ile
    1130            1135                1140

Asn Asp  Arg Phe Ile Asp Ser  Leu Val Gln Asn Gly  Tyr Gly Leu
    1145            1150                1155

Ser Asp  Arg Tyr Asp Leu Gly  Phe Glu Thr Pro Thr  Lys Tyr Gly
    1160            1165                1170

Thr Asp  Gln Asp Leu Arg Thr  Ala Ile Lys Thr Leu  His Gln Ala
```

-continued

```
      1175            1180                1185

Gly Met  Thr Val Met Ala Asp  Tyr Val Ala Asn Gln  Ile Tyr Gly
    1190            1195                1200

Leu Asn  Thr Ser Gln Glu Val  Val Asp Ala Gln Arg  Val Asn Ser
    1205            1210                1215

Asp Asn  Asn Ala Val Glu Val  Arg Tyr Gly Gln His  Leu Asn Val
    1220            1225                1230

Val Asn  Ser Ile Gly Gly Gly  Glu Tyr Gln Asn Leu  Tyr Gly Gly
    1235            1240                1245

Lys Tyr  Leu Glu Ile Leu Asn  Lys Leu Tyr Pro Asp  Leu Leu Val
    1250            1255                1260

Asp Glu  Asn Gly Asn Lys Ile  Asp Ile Asp Thr Lys  Ile Lys Gln
    1265            1270                1275

Trp Ser  Ala Lys Tyr Leu Asn  Gly Ser Asn Val Thr  Gly Leu Gly
    1280            1285                1290

Met Gly  Tyr Val Leu Lys Asp  Trp Ser Asn Gly Gln  Tyr Phe Asn
    1295            1300                1305

Ile Ser  Asn Thr Asp Gly Lys  Val Met Leu Pro Glu  Gln Leu Val
    1310            1315                1320

Lys His  Met Pro Ala Val Glu  Ile Gly Thr Gln Thr  Asn Tyr Thr
    1325            1330                1335

Ala Tyr  Ile Ser Ser Thr Ile  Arg Arg Asp Gly Leu  Tyr Asn Asn
    1340            1345                1350

Met Pro  Trp Gly Val Thr Ala  Thr Gly Gln Asp Gly  Asn Glu Ile
    1355            1360                1365

Lys Trp  Glu Arg Gln Gly Ser  Thr Ser Asp Tyr Asn  His Gln Lys
    1370            1375                1380

Val Gln  Val Asn Arg Gln Tyr  Val Asp Lys Gln Gly  Val Val Trp
    1385            1390                1395

Asn Leu  Ile Asn Phe Asp Asp  Lys Asp Leu Trp Val  Asp Ser Asn
    1400            1405                1410

Ala Leu  Val Thr Val Asn Phe  Thr Ser Gln Lys Pro  Thr Lys His
    1415            1420                1425

Phe Val  Gln Phe Gly Met Arg  Gln Gly Lys Tyr Asp  Gly Phe Tyr
    1430            1435                1440

Leu Ser  Ala Pro Tyr Lys Gln  Thr Glu Ser Lys Trp  Val Ala Ser
    1445            1450                1455

Thr Arg  Thr His Gln Gly Gln  Leu Leu Glu Val Val  Gly Gln Tyr
    1460            1465                1470

Thr Thr  Gly Ser Gly Ser Arg  Lys Val Thr Trp Tyr  Leu Val Gly
    1475            1480                1485

Leu Asp  Gly Lys Gln Val Trp  Val Asp Ser Arg Ala  Val Gly Thr
    1490            1495                1500

Asn Phe  Ser His Lys Thr Asn  Ile Asn Leu Leu Ile  Asn Ser Ala
    1505            1510                1515

Thr Arg  Asn Asp Gly Met Tyr  Leu Asn Ala Pro Tyr  Gly Gln Lys
    1520            1525                1530

Gly Tyr  Lys Arg Glu Thr Ser  Ser Arg Phe Tyr Asn  Glu Lys Leu
    1535            1540                1545

Val Thr  Val Ser Gln Gln Tyr  Tyr Asp Asn Lys Gly  Val Ile Trp
    1550            1555                1560

Asn Leu  Ile Thr Leu Asn Gly  Lys Lys Leu Trp Val  Asp Ser Arg
    1565            1570                1575
```

-continued

```
Ala Phe  Ala Thr Val Ile Asp  Lys Lys Val Asn Gln  Ser Leu Tyr
    1580             1585             1590

Ile Asn  Ser Arg Asn Asp Gly  Met Tyr Leu Asn Ala  Pro Tyr Arg
    1595             1600             1605

Ala Gln  Gly Ala Lys Arg Tyr  Ala Ser Thr Lys Thr  Tyr Thr Gly
    1610             1615             1620

Gln Arg  Val Gln Val Thr Leu  Gln Arg Lys Asp Thr  His Gly Val
    1625             1630             1635

Thr Trp  Tyr Leu Thr Lys Val  Asp Ser Lys Gln Leu  Trp Val Asp
    1640             1645             1650

Ser His  Ala Phe Ala Pro Thr  Phe Thr Arg Asn Val  Ser Leu Asn
    1655             1660             1665

Val Lys  Val Asn Ser Ser Lys  Arg Asn Asp Gly Ile  Tyr Leu Asn
    1670             1675             1680

Ala Pro  Tyr Gly Asn Lys Lys  Ala Lys Arg Ile Ala  Ser Thr Lys
    1685             1690             1695

Ala Tyr  Asn Gly Lys Arg Val  Lys Ala Ser Lys Glu  Tyr Lys Asp
    1700             1705             1710

Ala Lys  Gly Val Thr Trp Tyr  Leu Val Asn Leu Asn  Asn Lys Gln
    1715             1720             1725

Val Trp  Ile Asp Lys Arg Ala  Phe His His His His  His His
    1730             1735             1740

<210> SEQ ID NO 3
<211> LENGTH: 1735
<212> TYPE: PRT
<213> ORGANISM: Leuconostoc fallax

<400> SEQUENCE: 3

Thr Thr Val Ala Ser Ala Asp Val Gln Lys Asp Thr Val Val Thr
1               5               10              15

Ala Asp Lys Asn Thr Thr Asp Lys Asp Lys Glu Pro Ile Lys Thr Ala
            20              25              30

Gly Ala Asn Val Val Asp Lys Gly Val Ala Gln Thr Thr Asp Thr Asn
        35              40              45

Thr Thr Asp Lys Lys Thr Ile Glu Val Gly Lys Ser Val Asp Met Ser
    50              55              60

Ala Thr Asp Lys Lys Val Thr Glu Thr Val Lys Ser Val Asp Thr Ser
65              70              75              80

Ala Thr Asp Lys Lys Thr Thr Glu Ala Val Lys Pro Val Asp Thr Asn
            85              90              95

Ala Thr Asp Lys Lys Ala Thr Glu Ala Val Lys Pro Val Asp Thr Asn
            100             105             110

Ala Thr Asp Lys Lys Thr Thr Glu Ala Val Lys Pro Val Asp Thr Asn
        115             120             125

Thr Thr Asp Lys Lys Val Thr Glu Ala Ile Lys Pro Val Asn Thr Asn
    130             135             140

Ala Asp Asp Lys Thr Ala Glu Pro Val Lys Thr Ile Ser Ala Thr Lys
145             150             155             160

Asp Thr Val Lys Thr Ile Ala Asn Lys Gln Lys Gly Ala Thr Glu Glu
            165             170             175

Gln Ala Val Ile Thr Glu Gly His Tyr Glu Ala Gln Gly Asp Gly Phe
        180             185             190

Val Tyr Ile Thr Lys Asp Gly Lys Gln Leu Thr Gly Leu Gln Asn Ile
```

-continued

```
              195                 200                 205

Asn Gly Asn Thr Gln Tyr Phe Asp Pro Ala Thr Gly Gln Gln Leu Lys
    210                 215                 220

Gly Asp Ile Lys Ala Val Ala Gly Thr Val Tyr Tyr Phe Asp Lys Asn
225                 230                 235                 240

Ser Gly Asn Ala Arg Val Tyr Gln Lys Val Ala Asp Gly Thr Tyr Ser
                245                 250                 255

Glu Asn Asn Glu His Trp Gln Tyr Ile Ser Lys Val Asp Asn Lys Pro
            260                 265                 270

Val Glu Gly Leu Tyr Asn Val Gln Gly Asn Leu Gln Tyr Phe Asp Met
        275                 280                 285

Ser Thr Gly Asn Gln Val Lys Asn Asp Ile Arg Ser Val Asp Gly Val
    290                 295                 300

Thr Tyr Tyr Phe Asp Lys Asp Ser Gly Asn Gly Ser Ala Phe Asn Ala
305                 310                 315                 320

Leu Ser Ala Gly Glu Tyr Val Glu Lys Lys Glu Thr Asp Ala Gln Gly
                325                 330                 335

Asn Gln Asn Ser Tyr Trp Thr Tyr Ser Gly Leu Asp Gly Asn Pro Val
            340                 345                 350

Lys Gly Leu Tyr Asp Ile Asn Gly Ser Leu Gln Tyr Phe Asp Glu Lys
        355                 360                 365

Asn Gly Ala Gln Leu Lys Gly Gly Thr Ala Thr Val Asn Gly Val Thr
    370                 375                 380

Tyr Tyr Phe Glu Gln Asp Lys Gly Asn Leu Ile Ser Val Val Asn Ser
385                 390                 395                 400

Val Glu Ser Gly Gln Tyr Lys Ile Asp Asn Asp Asn Val Tyr Tyr Ile
                405                 410                 415

Asp Asn Gln Gly Asn Thr Leu Lys Gly Leu Tyr Ala Ile Asn Gly Gln
            420                 425                 430

Leu Asn Tyr Phe Asp Met Ser Thr Gly Val Gln Leu Lys Gly Ala Ser
        435                 440                 445

Glu Asn Ala Asn Gly Val Gly Tyr Tyr Phe Asp Lys Asp Lys Gly Asn
    450                 455                 460

Gly Gln Tyr Gln Tyr Ser Leu Ile Thr Ser Thr Leu Ala Asn Ala Phe
465                 470                 475                 480

Ser Lys His Asn Ala Ala Asn Asp Tyr Thr Gln Ser Ser Phe Thr His
                485                 490                 495

Thr Val Asp Gly Phe Leu Thr Ala Asp Thr Trp Tyr Arg Pro Thr Glu
            500                 505                 510

Ile Leu Lys Asn Gly Thr Thr Trp Val Ala Ser Thr Ser Gln Asp Leu
        515                 520                 525

Arg Pro Met Ile Thr Val Trp Trp Pro Asn Lys Asn Val Gln Leu Asn
    530                 535                 540

Tyr Leu Lys Leu Met Gln Thr Glu Gly Leu Leu Asp Ser Gly Gln Val
545                 550                 555                 560

Tyr Asp Leu Asn Ser Asp Gln Ala Leu Leu Asn Gln Ala Ala Gln Thr
                565                 570                 575

Val Gln Val Asn Ile Glu Lys Arg Ile Thr Lys Ala Gly Asn Ser Asp
            580                 585                 590

Trp Leu Asn Asp Leu Leu Tyr Asn Ser His Gly Glu Thr Pro Ser Phe
        595                 600                 605

Val Lys Gln Gln Ala Ile Trp Asn Ala Asp Ser Glu Tyr His Gly Gly
    610                 615                 620
```

-continued

```
Trp Phe Gln Gly Gly Tyr Leu Ala Tyr Arg Asn Ser Asp Leu Thr Pro
625                 630                 635                 640

Tyr Ala Asn Ser Ser Tyr Arg His Tyr Thr Gly Met Glu Phe Leu Leu
                645                 650                 655

Ala Asn Asp Val Asp Asn Ser Asn Pro Ile Val Gln Ala Glu Asp Leu
                660                 665                 670

Asn Trp Leu Tyr Tyr Leu Met Asn Phe Gly Thr Glu Thr Gly Asn Asp
        675                 680                 685

Pro Gln Ala Asn Phe Asp Ser Ile Arg Ile Asp Ala Ile Ser Phe Val
        690                 695                 700

Asp Lys Gln Val Ala Lys Lys Ala Tyr Glu Leu Leu His Asp Met Tyr
705                 710                 715                 720

Gly Leu Ser Ala Ser Asp Ala Val Ala Asn Lys His Val Ser Ile Val
                725                 730                 735

Glu Ala Ser Ala Asp Gln Thr Pro Val Thr Thr Glu Asn His Asp Ala
                740                 745                 750

Leu Ile Glu Ser Tyr Trp Arg Asp Thr Met Lys Asn Ser Leu Ser Lys
            755                 760                 765

Asp Ala Ser Ile Asp Ser Ser Ala Gly Ser Leu Ser Ala Met Ile Asn
        770                 775                 780

Asp Gly Asn Val Asp Arg Ala Asn Asp Ser Thr Thr Glu Ser Ser Ile
785                 790                 795                 800

Phe Pro Asn Tyr Thr Ile Val His Ala His Asp Lys Asp Ile Gln Asp
                805                 810                 815

Ala Val Ser Asn Val Met Lys Ile Val Asn Asn Asp Pro Ser Ile Ser
                820                 825                 830

Leu Asp Gly Phe Thr Met Glu Gln Leu Glu Lys Gly Leu Ser Ala Phe
            835                 840                 845

Tyr Ala Asp Gln Arg Ser Ala Val Lys Gln Tyr Asn Gln Tyr Asn Ile
        850                 855                 860

Pro Ser Ala Tyr Ala Val Met Leu Thr Asn Lys Asp Thr Val Pro Arg
865                 870                 875                 880

Thr Phe Tyr Gly Asp Met Tyr Gln Asp Asp Gly Gln Tyr Met Ala Asn
                885                 890                 895

Lys Ser Leu Tyr Tyr Asp Ala Ile Asp Thr Met Met Lys Ala Arg Leu
            900                 905                 910

Lys Tyr Val Ser Gly Gly Gln Thr Met Ser Val Thr Lys Ile Asn Asn
            915                 920                 925

Ala Asn Ser Gln Lys Ser Gly Glu Val Leu Thr Ser Val Arg Phe Gly
        930                 935                 940

Lys Gly Val Met Asp Ala Thr Asp Ala Gly Ser Ala Glu Ser Arg Thr
945                 950                 955                 960

Gln Gly Ile Gly Val Val Val Ser Asn Ser Ser Gly Leu Gln Leu Asn
                965                 970                 975

Asp Asn Asp Lys Ile Val Leu His Met Gly Ala Ala His Lys Asn Gln
            980                 985                 990

Glu Tyr Arg Ala Leu Met Leu Thr  Thr Asn Asp Gly Ile  Lys Ser Phe
            995                 1000                1005

Asn Asn  Asp Glu Ala Pro Ile  Asn Tyr Thr Asp Asp  Asn Gly Asp
        1010                1015                1020

Leu Ile  Phe Asp Gly His Asn  Ile Asp Gly Gln Glu  Asn Thr Ala
        1025                1030                1035
```

-continued

```
Ile Arg  Gly Tyr Leu Asn Pro  Gln Val Ala Gly Tyr  Leu Ala Val
    1040                1045              1050

Trp Val  Pro Thr Gly Ala Lys  Asp Asp Gln Asp Ala  Arg Thr Gln
    1055                1060              1065

Pro Ser  Asn Glu Lys Ser Thr  Asp Gly Lys Val Leu  His Thr Asn
    1070                1075              1080

Ala Ala  Leu Asp Ser Glu Leu  Ile Tyr Glu Gly Phe  Ser Asn Phe
    1085                1090              1095

Gln Pro  Met Pro Thr Thr Lys  Asp Glu Tyr Thr Asn  Val Met Ile
    1100                1105              1110

Ala Lys  Asn Ile Asp Leu Phe  Lys Ser Trp Gly Ile  Thr Asn Phe
    1115                1120              1125

Glu Leu  Ala Pro Gln Tyr Arg  Ser Ser Asp Gly Lys  Asn Ile Asn
    1130                1135              1140

Asp Arg  Phe Ile Asp Ser Leu  Val Gln Asn Gly Tyr  Gly Leu Ser
    1145                1150              1155

Asp Arg  Tyr Asp Leu Gly Phe  Glu Thr Pro Thr Lys  Tyr Gly Thr
    1160                1165              1170

Asp Gln  Asp Leu Arg Thr Ala  Ile Lys Thr Leu His  Gln Ala Gly
    1175                1180              1185

Met Thr  Val Met Ala Asp Tyr  Val Ala Asn Gln Ile  Tyr Gly Leu
    1190                1195              1200

Asn Thr  Ser Gln Glu Val Val  Asp Ala Gln Arg Val  Asn Ser Asp
    1205                1210              1215

Asn Asn  Ala Val Glu Val Arg  Tyr Gly Gln His Leu  Asn Val Val
    1220                1225              1230

Asn Ser  Ile Gly Gly Gly Glu  Tyr Gln Asn Leu Tyr  Gly Gly Lys
    1235                1240              1245

Tyr Leu  Glu Ile Leu Asn Lys  Leu Tyr Pro Asp Leu  Leu Val Asp
    1250                1255              1260

Glu Asn  Gly Asn Lys Ile Asp  Ile Asp Thr Lys Ile  Lys Gln Trp
    1265                1270              1275

Ser Ala  Lys Tyr Leu Asn Gly  Ser Asn Val Thr Gly  Leu Gly Met
    1280                1285              1290

Gly Tyr  Val Leu Lys Asp Trp  Ser Asn Gly Gln Tyr  Phe Asn Ile
    1295                1300              1305

Ser Asn  Thr Asp Gly Lys Val  Met Leu Pro Glu Gln  Leu Val Lys
    1310                1315              1320

His Met  Pro Ala Val Glu Ile  Gly Thr Gln Thr Asn  Tyr Thr Ala
    1325                1330              1335

Tyr Ile  Ser Ser Thr Ile Arg  Arg Asp Gly Leu Tyr  Asn Asn Met
    1340                1345              1350

Pro Trp  Gly Val Thr Ala Thr  Gly Gln Asp Gly Asn  Glu Ile Lys
    1355                1360              1365

Trp Glu  Arg Gln Gly Ser Thr  Ser Asp Tyr Asn His  Gln Lys Val
    1370                1375              1380

Gln Val  Asn Arg Gln Tyr Val  Asp Lys Gln Gly Val  Val Trp Asn
    1385                1390              1395

Leu Ile  Asn Phe Asp Asp Lys  Asp Leu Trp Val Asp  Ser Asn Ala
    1400                1405              1410

Leu Val  Thr Val Asn Phe Thr  Ser Gln Lys Pro Thr  Lys His Phe
    1415                1420              1425

Val Gln  Phe Gly Met Arg Gln  Gly Lys Tyr Asp Gly  Phe Tyr Leu
```

-continued

```
              1430                1435                1440

Ser Ala  Pro Tyr Lys Gln Thr  Glu Ser Lys Trp Val  Ala Ser Thr
    1445                1450                1455

Arg Thr  His Gln Gly Gln Leu  Leu Glu Val Val Gly  Gln Tyr Thr
    1460                1465                1470

Thr Gly  Ser Gly Ser Arg Lys  Val Thr Trp Tyr Leu  Val Gly Leu
    1475                1480                1485

Asp Gly  Lys Gln Val Trp Val  Asp Ser Arg Ala Val  Gly Thr Asn
    1490                1495                1500

Phe Ser  His Lys Thr Asn Ile  Asn Leu Leu Ile Asn  Ser Ala Thr
    1505                1510                1515

Arg Asn  Asp Gly Met Tyr Leu  Asn Ala Pro Tyr Gly  Gln Lys Gly
    1520                1525                1530

Tyr Lys  Arg Glu Thr Ser Ser  Arg Phe Tyr Asn Glu  Lys Leu Val
    1535                1540                1545

Thr Val  Ser Gln Gln Tyr Tyr  Asp Asn Lys Gly Val  Ile Trp Asn
    1550                1555                1560

Leu Ile  Thr Leu Asn Gly Lys  Lys Leu Trp Val Asp  Ser Arg Ala
    1565                1570                1575

Phe Ala  Thr Val Ile Asp Lys  Lys Val Asn Gln Ser  Leu Tyr Ile
    1580                1585                1590

Asn Ser  Arg Asn Asp Gly Met  Tyr Leu Asn Ala Pro  Tyr Arg Ala
    1595                1600                1605

Gln Gly  Ala Lys Arg Tyr Ala  Ser Thr Lys Thr Tyr  Thr Gly Gln
    1610                1615                1620

Arg Val  Gln Val Thr Leu Gln  Arg Lys Asp Thr His  Gly Val Thr
    1625                1630                1635

Trp Tyr  Leu Thr Lys Val Asp  Ser Lys Gln Leu Trp  Val Asp Ser
    1640                1645                1650

His Ala  Phe Ala Pro Thr Phe  Thr Arg Asn Val Ser  Leu Asn Val
    1655                1660                1665

Lys Val  Asn Ser Ser Lys Arg  Asn Asp Gly Ile Tyr  Leu Asn Ala
    1670                1675                1680

Pro Tyr  Gly Asn Lys Lys Ala  Lys Arg Ile Ala Ser  Thr Lys Ala
    1685                1690                1695

Tyr Asn  Gly Lys Arg Val Lys  Ala Ser Lys Glu Tyr  Lys Asp Ala
    1700                1705                1710

Lys Gly  Val Thr Trp Tyr Leu  Val Asn Leu Asn Asn  Lys Gln Val
    1715                1720                1725

Trp Ile  Asp Lys Arg Ala Phe
    1730                1735

<210> SEQ ID NO 4
<211> LENGTH: 1774
<212> TYPE: PRT
<213> ORGANISM: Leuconostoc fallax

<400> SEQUENCE: 4

Met Lys Gln Gln Glu Ser Ile Thr Arg Lys Lys Leu Tyr Lys Ala Gly
1               5                   10                  15

Lys Ser Trp Val Val Ala Ala Thr Leu Phe Ala Ala Thr Leu Phe Ala
            20                  25                  30

Ala Met Gly Ala Ala Gly Ala Thr Thr Val Ala Ser Ala Asp Val Gln
        35                  40                  45
```

-continued

```
Lys Asp Thr Val Val Val Thr Ala Asp Lys Asn Thr Thr Asp Lys Asp
    50                  55                  60

Lys Glu Pro Ile Lys Thr Ala Gly Ala Asn Val Val Asp Lys Gly Val
65                  70                  75                  80

Ala Gln Thr Thr Asp Thr Asn Thr Thr Asp Lys Lys Thr Ile Glu Val
                85                  90                  95

Gly Lys Ser Val Asp Met Ser Ala Thr Asp Lys Lys Val Thr Glu Thr
                100                 105                 110

Val Lys Ser Val Asp Thr Ser Ala Thr Asp Lys Lys Thr Thr Glu Ala
            115                 120                 125

Val Lys Pro Val Asp Thr Asn Ala Thr Asp Lys Lys Ala Thr Glu Ala
    130                 135                 140

Val Lys Pro Val Asp Thr Asn Ala Thr Asp Lys Lys Thr Thr Glu Ala
145                 150                 155                 160

Val Lys Pro Val Asp Thr Asn Thr Thr Asp Lys Lys Val Thr Glu Ala
                165                 170                 175

Ile Lys Pro Val Asn Thr Asn Ala Asp Asp Lys Thr Ala Glu Pro Val
            180                 185                 190

Lys Thr Ile Ser Ala Thr Lys Asp Thr Val Lys Thr Ile Ala Asn Lys
            195                 200                 205

Gln Lys Gly Ala Thr Glu Glu Gln Ala Val Ile Thr Glu Gly His Tyr
    210                 215                 220

Glu Ala Gln Gly Asp Gly Phe Val Tyr Ile Thr Lys Asp Gly Lys Gln
225                 230                 235                 240

Leu Thr Gly Leu Gln Asn Ile Asn Gly Asn Thr Gln Tyr Phe Asp Pro
                245                 250                 255

Ala Thr Gly Gln Gln Leu Lys Gly Asp Ile Lys Ala Val Ala Gly Thr
                260                 265                 270

Val Tyr Tyr Phe Asp Lys Asn Ser Gly Asn Ala Arg Val Tyr Gln Lys
            275                 280                 285

Val Ala Asp Gly Thr Tyr Ser Glu Asn Asn Glu His Trp Gln Tyr Ile
    290                 295                 300

Ser Lys Val Asp Asn Lys Pro Val Glu Gly Leu Tyr Asn Val Gln Gly
305                 310                 315                 320

Asn Leu Gln Tyr Phe Asp Met Ser Thr Gly Asn Gln Val Lys Asn Asp
                325                 330                 335

Ile Arg Ser Val Asp Gly Val Thr Tyr Tyr Phe Asp Lys Asp Ser Gly
            340                 345                 350

Asn Gly Ser Ala Phe Asn Ala Leu Ser Ala Gly Glu Tyr Val Glu Lys
            355                 360                 365

Lys Glu Thr Asp Ala Gln Gly Asn Gln Asn Ser Tyr Trp Thr Tyr Ser
    370                 375                 380

Gly Leu Asp Gly Asn Pro Val Lys Gly Leu Tyr Asp Ile Asn Gly Ser
385                 390                 395                 400

Leu Gln Tyr Phe Asp Glu Lys Asn Gly Ala Gln Leu Lys Gly Gly Thr
                405                 410                 415

Ala Thr Val Asn Gly Val Thr Tyr Tyr Phe Glu Gln Asp Lys Gly Asn
                420                 425                 430

Leu Ile Ser Val Val Asn Ser Val Glu Ser Gly Gln Tyr Lys Ile Asp
            435                 440                 445

Asn Asp Asn Val Tyr Tyr Ile Asp Asn Gln Gly Asn Thr Leu Lys Gly
    450                 455                 460

Leu Tyr Ala Ile Asn Gly Gln Leu Asn Tyr Phe Asp Met Ser Thr Gly
```

-continued

```
465                  470                  475                  480
Val Gln Leu Lys Gly Ala Ser Glu Asn Ala Asn Gly Val Gly Tyr Tyr
                485                  490                  495

Phe Asp Lys Asp Lys Gly Asn Gly Gln Tyr Gln Tyr Ser Leu Ile Thr
                500                  505                  510

Ser Thr Leu Ala Asn Ala Phe Ser Lys His Asn Ala Ala Asn Asp Tyr
                515                  520                  525

Thr Gln Ser Ser Phe Thr His Thr Val Asp Gly Phe Leu Thr Ala Asp
    530                  535                  540

Thr Trp Tyr Arg Pro Thr Glu Ile Leu Lys Asn Gly Thr Thr Trp Val
545                  550                  555                  560

Ala Ser Thr Ser Gln Asp Leu Arg Pro Met Ile Thr Val Trp Trp Pro
                565                  570                  575

Asn Lys Asn Val Gln Leu Asn Tyr Leu Lys Leu Met Gln Thr Glu Gly
                580                  585                  590

Leu Leu Asp Ser Gly Gln Val Tyr Asp Leu Asn Ser Asp Gln Ala Leu
                595                  600                  605

Leu Asn Gln Ala Ala Gln Thr Val Gln Val Asn Ile Glu Lys Arg Ile
    610                  615                  620

Thr Lys Ala Gly Asn Ser Asp Trp Leu Asn Asp Leu Leu Tyr Asn Ser
625                  630                  635                  640

His Gly Glu Thr Pro Ser Phe Val Lys Gln Gln Ala Ile Trp Asn Ala
                645                  650                  655

Asp Ser Glu Tyr His Gly Gly Trp Phe Gln Gly Gly Tyr Leu Ala Tyr
                660                  665                  670

Arg Asn Ser Asp Leu Thr Pro Tyr Ala Asn Ser Ser Tyr Arg His Tyr
                675                  680                  685

Thr Gly Met Glu Phe Leu Leu Ala Asn Asp Val Asp Asn Ser Asn Pro
    690                  695                  700

Ile Val Gln Ala Glu Asp Leu Asn Trp Leu Tyr Tyr Leu Met Asn Phe
705                  710                  715                  720

Gly Thr Glu Thr Gly Asn Asp Pro Gln Ala Asn Phe Asp Ser Ile Arg
                725                  730                  735

Ile Asp Ala Ile Ser Phe Val Asp Lys Gln Val Ala Lys Lys Ala Tyr
                740                  745                  750

Glu Leu Leu His Asp Met Tyr Gly Leu Ser Ala Ser Asp Ala Val Ala
                755                  760                  765

Asn Lys His Val Ser Ile Val Glu Ala Ser Ala Asp Gln Thr Pro Val
    770                  775                  780

Thr Thr Glu Asn His Asp Ala Leu Ile Glu Ser Tyr Trp Arg Asp Thr
785                  790                  795                  800

Met Lys Asn Ser Leu Ser Lys Asp Ala Ser Ile Asp Ser Ser Ala Gly
                805                  810                  815

Ser Leu Ser Ala Met Ile Asn Asp Gly Asn Val Asp Arg Ala Asn Asp
                820                  825                  830

Ser Thr Thr Glu Ser Ser Ile Phe Pro Asn Tyr Thr Ile Val His Ala
                835                  840                  845

His Asp Lys Asp Ile Gln Asp Ala Val Ser Asn Val Met Lys Ile Val
    850                  855                  860

Asn Asn Asp Pro Ser Ile Ser Leu Asp Gly Phe Thr Met Glu Gln Leu
865                  870                  875                  880

Glu Lys Gly Leu Ser Ala Phe Tyr Ala Asp Gln Arg Ser Ala Val Lys
                885                  890                  895
```

-continued

```
Gln Tyr Asn Gln Tyr Asn Ile Pro Ser Ala Tyr Ala Val Met Leu Thr
            900             905             910

Asn Lys Asp Thr Val Pro Arg Thr Phe Tyr Gly Asp Met Tyr Gln Asp
            915             920             925

Asp Gly Gln Tyr Met Ala Asn Lys Ser Leu Tyr Tyr Asp Ala Ile Asp
            930             935             940

Thr Met Met Lys Ala Arg Leu Lys Tyr Val Ser Gly Gly Gln Thr Met
945             950             955             960

Ser Val Thr Lys Ile Asn Asn Ala Asn Ser Gln Lys Ser Gly Glu Val
                965             970             975

Leu Thr Ser Val Arg Phe Gly Lys Gly Val Met Asp Ala Thr Asp Ala
            980             985             990

Gly Ser Ala Glu Ser Arg Thr Gln  Gly Ile Gly Val Val  Val Ser Asn
            995             1000             1005

Ser Ser  Gly Leu Gln Leu Asn  Asp Asn Asp Lys Ile  Val Leu His
    1010             1015             1020

Met Gly  Ala Ala His Lys Asn  Gln Glu Tyr Arg Ala  Leu Met Leu
    1025             1030             1035

Thr Thr  Asn Asp Gly Ile Lys  Ser Phe Asn Asn Asp  Glu Ala Pro
    1040             1045             1050

Ile Asn  Tyr Thr Asp Asp Asn  Gly Asp Leu Ile Phe  Asp Gly His
    1055             1060             1065

Asn Ile  Asp Gly Gln Glu Asn  Thr Ala Ile Arg Gly  Tyr Leu Asn
    1070             1075             1080

Pro Gln  Val Ala Gly Tyr Leu  Ala Val Trp Val Pro  Thr Gly Ala
    1085             1090             1095

Lys Asp  Asp Gln Asp Ala Arg  Thr Gln Pro Ser Asn  Glu Lys Ser
    1100             1105             1110

Thr Asp  Gly Lys Val Leu His  Thr Asn Ala Ala Leu  Asp Ser Glu
    1115             1120             1125

Leu Ile  Tyr Glu Gly Phe Ser  Asn Phe Gln Pro Met  Pro Thr Thr
    1130             1135             1140

Lys Asp  Glu Tyr Thr Asn Val  Met Ile Ala Lys Asn  Ile Asp Leu
    1145             1150             1155

Phe Lys  Ser Trp Gly Ile Thr  Asn Phe Glu Leu Ala  Pro Gln Tyr
    1160             1165             1170

Arg Ser  Ser Asp Gly Lys Asn  Ile Asn Asp Arg Phe  Ile Asp Ser
    1175             1180             1185

Leu Val  Gln Asn Gly Tyr Gly  Leu Ser Asp Arg Tyr  Asp Leu Gly
    1190             1195             1200

Phe Glu  Thr Pro Thr Lys Tyr  Gly Thr Asp Gln Asp  Leu Arg Thr
    1205             1210             1215

Ala Ile  Lys Thr Leu His Gln  Ala Gly Met Thr Val  Met Ala Asp
    1220             1225             1230

Tyr Val  Ala Asn Gln Ile Tyr  Gly Leu Asn Thr Ser  Gln Glu Val
    1235             1240             1245

Val Asp  Ala Gln Arg Val Asn  Ser Asp Asn Asn Ala  Val Glu Val
    1250             1255             1260

Arg Tyr  Gly Gln His Leu Asn  Val Val Asn Ser Ile  Gly Gly Gly
    1265             1270             1275

Glu Tyr  Gln Asn Leu Tyr Gly  Gly Lys Tyr Leu Glu  Ile Leu Asn
    1280             1285             1290
```

-continued

```
Lys Leu Tyr Pro Asp Leu Leu Val Asp Glu Asn Gly Asn Lys Ile
    1295              1300              1305

Asp Ile Asp Thr Lys Ile Lys Gln Trp Ser Ala Lys Tyr Leu Asn
    1310              1315              1320

Gly Ser Asn Val Thr Gly Leu Gly Met Gly Tyr Val Leu Lys Asp
    1325              1330              1335

Trp Ser Asn Gly Gln Tyr Phe Asn Ile Ser Asn Thr Asp Gly Lys
    1340              1345              1350

Val Met Leu Pro Glu Gln Leu Val Lys His Met Pro Ala Val Glu
    1355              1360              1365

Ile Gly Thr Gln Thr Asn Tyr Thr Ala Tyr Ile Ser Ser Thr Ile
    1370              1375              1380

Arg Arg Asp Gly Leu Tyr Asn Asn Met Pro Trp Gly Val Thr Ala
    1385              1390              1395

Thr Gly Gln Asp Gly Asn Glu Ile Lys Trp Glu Arg Gln Gly Ser
    1400              1405              1410

Thr Ser Asp Tyr Asn His Gln Lys Val Gln Val Asn Arg Gln Tyr
    1415              1420              1425

Val Asp Lys Gln Gly Val Val Trp Asn Leu Ile Asn Phe Asp Asp
    1430              1435              1440

Lys Asp Leu Trp Val Asp Ser Asn Ala Leu Val Thr Val Asn Phe
    1445              1450              1455

Thr Ser Gln Lys Pro Thr Lys His Phe Val Gln Phe Gly Met Arg
    1460              1465              1470

Gln Gly Lys Tyr Asp Gly Phe Tyr Leu Ser Ala Pro Tyr Lys Gln
    1475              1480              1485

Thr Glu Ser Lys Trp Val Ala Ser Thr Arg Thr His Gln Gly Gln
    1490              1495              1500

Leu Leu Glu Val Val Gly Gln Tyr Thr Thr Gly Ser Gly Ser Arg
    1505              1510              1515

Lys Val Thr Trp Tyr Leu Val Gly Leu Asp Gly Lys Gln Val Trp
    1520              1525              1530

Val Asp Ser Arg Ala Val Gly Thr Asn Phe Ser His Lys Thr Asn
    1535              1540              1545

Ile Asn Leu Leu Ile Asn Ser Ala Thr Arg Asn Asp Gly Met Tyr
    1550              1555              1560

Leu Asn Ala Pro Tyr Gly Gln Lys Gly Tyr Lys Arg Glu Thr Ser
    1565              1570              1575

Ser Arg Phe Tyr Asn Glu Lys Leu Val Thr Val Ser Gln Gln Tyr
    1580              1585              1590

Tyr Asp Asn Lys Gly Val Ile Trp Asn Leu Ile Thr Leu Asn Gly
    1595              1600              1605

Lys Lys Leu Trp Val Asp Ser Arg Ala Phe Ala Thr Val Ile Asp
    1610              1615              1620

Lys Lys Val Asn Gln Ser Leu Tyr Ile Asn Ser Arg Asn Asp Gly
    1625              1630              1635

Met Tyr Leu Asn Ala Pro Tyr Arg Ala Gln Gly Ala Lys Arg Tyr
    1640              1645              1650

Ala Ser Thr Lys Thr Tyr Thr Gly Gln Arg Val Gln Val Thr Leu
    1655              1660              1665

Gln Arg Lys Asp Thr His Gly Val Thr Trp Tyr Leu Thr Lys Val
    1670              1675              1680

Asp Ser Lys Gln Leu Trp Val Asp Ser His Ala Phe Ala Pro Thr
```

-continued

```
          1685                    1690                    1695

Phe Thr  Arg Asn Val Ser Leu  Asn Val Lys Val Asn  Ser Ser Lys
    1700                    1705                    1710

Arg Asn  Asp Gly Ile Tyr Leu  Asn Ala Pro Tyr Gly  Asn Lys Lys
    1715                    1720                    1725

Ala Lys  Arg Ile Ala Ser Thr  Lys Ala Tyr Asn Gly  Lys Arg Val
    1730                    1735                    1740

Lys Ala  Ser Lys Glu Tyr Lys  Asp Ala Lys Gly Val  Thr Trp Tyr
    1745                    1750                    1755

Leu Val  Asn Leu Asn Asn Lys  Gln Val Trp Ile Asp  Lys Arg Ala
    1760                    1765                    1770

Phe

<210> SEQ ID NO 5
<211> LENGTH: 7
<212> TYPE: PRT
<213> ORGANISM: Leuconostoc fallax

<400> SEQUENCE: 5

Ala Asp Tyr Val Ala Asn Gln
1               5

<210> SEQ ID NO 6
<211> LENGTH: 11
<212> TYPE: PRT
<213> ORGANISM: Leuconostoc fallax

<400> SEQUENCE: 6

Ser Ile Arg Ile Asp Ala Ile Ser Phe Val Asp
1               5                   10

<210> SEQ ID NO 7
<211> LENGTH: 11
<212> TYPE: PRT
<213> ORGANISM: Leuconostoc fallax

<400> SEQUENCE: 7

His Val Ser Ile Val Glu Ala Ser Ala Asp Gln
1               5                   10

<210> SEQ ID NO 8
<211> LENGTH: 15
<212> TYPE: PRT
<213> ORGANISM: Leuconostoc fallax

<400> SEQUENCE: 8

Ile Val His Ala His Asp Lys Asp Ile Gln Asp Ala Val Ser Asn
1               5                   10                  15

<210> SEQ ID NO 9
<211> LENGTH: 7
<212> TYPE: PRT
<213> ORGANISM: Unknown
<220> FEATURE:
<223> OTHER INFORMATION: Alpha-1,3-branching enzyme conserved motif I
<220> FEATURE:
<221> NAME/KEY: MISC_FEATURE
<222> LOCATION: (3)..(3)
<223> OTHER INFORMATION: Xaa is Phe or Tyr

<400> SEQUENCE: 9

Ala Asp Xaa Val Ala Asn Gln
1               5
```

```
<210> SEQ ID NO 10
<211> LENGTH: 11
<212> TYPE: PRT
<213> ORGANISM: Unknown
<220> FEATURE:
<223> OTHER INFORMATION: Alpha-1,3-branching enzyme conserved motif II
<220> FEATURE:
<221> NAME/KEY: MISC_FEATURE
<222> LOCATION: (2)..(2)
<223> OTHER INFORMATION: Xaa is Met or Ile

<400> SEQUENCE: 10

Ser Xaa Arg Ile Asp Ala Ile Ser Phe Val Asp
1               5                   10

<210> SEQ ID NO 11
<211> LENGTH: 11
<212> TYPE: PRT
<213> ORGANISM: Unknown
<220> FEATURE:
<223> OTHER INFORMATION: Alpha-1,3-branching enzyme conserved motif III
<220> FEATURE:
<221> NAME/KEY: MISC_FEATURE
<222> LOCATION: (2)..(2)
<223> OTHER INFORMATION: Xaa is Val or Ile
<220> FEATURE:
<221> NAME/KEY: MISC_FEATURE
<222> LOCATION: (8)..(8)
<223> OTHER INFORMATION: Xaa is Pro or Ser
<220> FEATURE:
<221> NAME/KEY: MISC_FEATURE
<222> LOCATION: (9)..(9)
<223> OTHER INFORMATION: Xaa is Lys or Ala
<220> FEATURE:
<221> NAME/KEY: MISC_FEATURE
<222> LOCATION: (10)..(10)
<223> OTHER INFORMATION: Xaa is Gly or Asp
<220> FEATURE:
<221> NAME/KEY: MISC_FEATURE
<222> LOCATION: (11)..(11)
<223> OTHER INFORMATION: Xaa is Glu or Gln

<400> SEQUENCE: 11

His Xaa Ser Ile Val Glu Ala Xaa Xaa Xaa Xaa
1               5                   10

<210> SEQ ID NO 12
<211> LENGTH: 15
<212> TYPE: PRT
<213> ORGANISM: Unknown
<220> FEATURE:
<223> OTHER INFORMATION: Alpha-1,3-branching enzyme conserved motif IV
<220> FEATURE:
<221> NAME/KEY: MISC_FEATURE
<222> LOCATION: (12)..(12)
<223> OTHER INFORMATION: Xaa is Thr or Ala
<220> FEATURE:
<221> NAME/KEY: MISC_FEATURE
<222> LOCATION: (14)..(14)
<223> OTHER INFORMATION: Xaa is Ser or Ile
<220> FEATURE:
<221> NAME/KEY: MISC_FEATURE
<222> LOCATION: (15)..(15)
<223> OTHER INFORMATION: Xaa is His or Asn

<400> SEQUENCE: 12

Ile Val His Ala His Asp Lys Asp Ile Gln Asp Xaa Val Xaa Xaa
1               5                   10                  15

<210> SEQ ID NO 13
<211> LENGTH: 1888
```

-continued

<212> TYPE: PRT
<213> ORGANISM: Leuconostoc citreum

<400> SEQUENCE: 13

```
Met Glu Met Lys Glu Thr Ile Thr Arg Lys Lys Leu Tyr Lys Ser Gly
1               5                   10                  15

Lys Ser Trp Val Ala Ala Ala Thr Ala Phe Ala Val Met Gly Val Ser
            20                  25                  30

Ala Val Thr Thr Val Ser Ala Asp Thr Gln Thr Pro Val Gly Thr Thr
            35                  40                  45

Gln Ser Gln Gln Asp Leu Thr Gly Gln Thr Gly Gln Asp Lys Pro Thr
        50                  55                  60

Thr Lys Glu Val Ile Asp Lys Lys Glu Pro Val Pro Gln Val Ser Ala
65                  70                  75                  80

Gln Asn Val Gly Asp Leu Ser Ala Asp Ala Lys Thr Pro Lys Ala Asp
                85                  90                  95

Asp Lys Gln Asp Thr Gln Pro Thr Asn Ala Gln Leu Pro Asp Gln Gly
            100                 105                 110

Asn Lys Gln Thr Asn Ser Asn Ser Asp Lys Gly Val Lys Glu Ser Thr
        115                 120                 125

Thr Ala Pro Val Lys Thr Thr Asp Val Pro Ser Lys Ser Val Ala Pro
    130                 135                 140

Glu Thr Asn Thr Ser Ile Asn Gly Gly Gln Tyr Val Glu Lys Asp Gly
145                 150                 155                 160

Gln Phe Val Tyr Ile Asp Gln Ser Gly Lys Gln Val Ser Gly Leu Gln
                165                 170                 175

Asn Ile Glu Gly His Thr Gln Tyr Phe Asp Pro Lys Thr Gly Tyr Gln
            180                 185                 190

Thr Lys Gly Glu Leu Lys Asn Ile Asp Asp Asn Ala Tyr Tyr Phe Asp
        195                 200                 205

Lys Asn Ser Gly Asn Gly Arg Thr Phe Thr Lys Ile Ser Asn Gly Ser
    210                 215                 220

Tyr Ser Glu Lys Asp Gly Met Trp Gln Tyr Val Asp Ser His Asp Lys
225                 230                 235                 240

Gln Pro Val Lys Gly Leu Tyr Asp Val Glu Gly Asn Leu Gln Tyr Phe
                245                 250                 255

Asp Leu Ser Thr Gly Asn Gln Ala Lys His Gln Ile Arg Ser Val Asp
            260                 265                 270

Gly Val Thr Tyr Tyr Phe Asp Ala Asp Ser Gly Asn Ala Thr Ala Phe
        275                 280                 285

Lys Ala Val Thr Asn Gly Arg Tyr Ala Glu Gln Thr Thr Lys Asp Lys
    290                 295                 300

Asp Gly Asn Glu Thr Ser Tyr Trp Ala Tyr Leu Asp Asn Gln Gly Asn
305                 310                 315                 320

Ala Ile Lys Gly Leu Asn Asp Val Asn Gly Glu Ile Gln Tyr Phe Asp
                325                 330                 335

Glu His Thr Gly Glu Gln Leu Lys Gly His Thr Ala Thr Val Asp Gly
            340                 345                 350

Thr Thr Tyr Tyr Phe Glu Gly Asn Lys Gly Asn Leu Val Ser Val Val
        355                 360                 365

Asn Thr Ala Pro Thr Gly Gln Tyr Lys Ile Asn Gly Asp Asn Val Tyr
    370                 375                 380

Tyr Leu Asp Asn Asn Asn Glu Ala Ile Lys Gly Leu Tyr Gly Ile Asn
385                 390                 395                 400
```

```
Gly Asn Leu Asn Tyr Phe Asp Leu Ala Thr Gly Ile Gln Leu Lys Gly
                405                 410                 415

Gln Ala Lys Asn Ile Asp Gly Ile Gly Tyr Tyr Phe Asp Gln Asn Asn
                420                 425                 430

Gly Asn Gly Glu Tyr Arg Tyr Ser Leu Thr Gly Pro Val Val Lys Asp
                435                 440                 445

Val Tyr Ser Gln His Asn Ala Val Asn Asn Leu Ser Ala Asn Asn Phe
        450                 455                 460

Lys Asn Leu Val Asp Gly Phe Leu Thr Ala Glu Thr Trp Tyr Arg Pro
465                 470                 475                 480

Ala Gln Ile Leu Ser His Gly Thr Asp Trp Val Ala Ser Thr Asp Lys
                485                 490                 495

Asp Phe Arg Pro Leu Ile Thr Val Trp Trp Pro Asn Lys Asp Ile Gln
                500                 505                 510

Val Asn Tyr Leu Lys Leu Met Gln Gln Ile Gly Ile Leu Asp Asn Ser
                515                 520                 525

Val Val Phe Asp Thr Asn Asn Asp Gln Leu Val Leu Asn Lys Gly Ala
        530                 535                 540

Glu Ser Ala Gln Ile Gly Ile Glu Lys Lys Val Ser Glu Thr Gly Asn
545                 550                 555                 560

Thr Asp Trp Leu Asn Glu Leu Leu Phe Ala Pro Asn Gly Asn Gln Pro
                565                 570                 575

Ser Phe Ile Lys Gln Gln Tyr Leu Trp Asn Val Asp Ser Glu Tyr Pro
                580                 585                 590

Gly Gly Trp Phe Gln Gly Gly Tyr Leu Ala Tyr Gln Asn Ser Asp Leu
                595                 600                 605

Thr Pro Tyr Ala Asn Thr Asn Pro Asp Tyr Arg Thr His Asn Gly Leu
        610                 615                 620

Glu Phe Leu Leu Ala Asn Asp Val Asp Asn Ser Asn Pro Val Val Gln
625                 630                 635                 640

Ala Glu Gln Leu Asn Trp Leu Tyr Tyr Leu Met Asn Phe Gly Gln Ile
                645                 650                 655

Thr Ala Asn Asp Ser Asn Ala Asn Phe Asp Ser Met Arg Ile Asp Ala
                660                 665                 670

Ile Ser Phe Val Asp Pro Gln Ile Ala Lys Lys Ala Tyr Asp Leu Leu
                675                 680                 685

Asp Lys Met Tyr Gly Leu Thr Asp Asn Glu Ala Val Ala Asn Gln His
        690                 695                 700

Ile Ser Ile Val Glu Ala Pro Lys Gly Glu Thr Pro Ile Thr Val Glu
705                 710                 715                 720

Lys Gln Ser Ala Leu Val Glu Ser Asn Trp Arg Asp Arg Met Lys Gln
                725                 730                 735

Ser Leu Ser Lys Asn Ala Thr Leu Asp Lys Leu Asp Pro Asp Pro Ala
                740                 745                 750

Ile Asn Ser Leu Glu Lys Leu Val Ala Asp Asp Leu Val Asn Arg Ser
                755                 760                 765

Gln Ser Ser Asp Lys Asp Ser Ser Thr Ile Pro Asn Tyr Ser Ile Val
        770                 775                 780

His Ala His Asp Lys Asp Ile Gln Asp Thr Val Ile His Ile Met Lys
785                 790                 795                 800

Ile Val Asn Asn Asn Pro Asn Ile Ser Met Ser Asp Phe Thr Met Gln
                805                 810                 815
```

-continued

```
Gln Leu Gln Asn Gly Leu Lys Ala Phe Tyr Glu Asp Gln His Gln Ser
            820                 825                 830

Val Lys Lys Tyr Asn Gln Tyr Asn Ile Pro Ser Ala Tyr Ala Leu Leu
        835                 840                 845

Leu Thr Asn Lys Asp Thr Val Pro Arg Val Phe Tyr Gly Asp Met Tyr
    850                 855                 860

Gln Asp Tyr Gly Asp Asp Leu Asp Gly Gly Gln Tyr Met Ala Thr Lys
865                 870                 875                 880

Ser Ile Tyr Tyr Asn Ala Ile Glu Gln Met Met Lys Ala Arg Leu Lys
                885                 890                 895

Tyr Val Ala Gly Gly Gln Ile Met Ala Val Thr Lys Ile Lys Asn Asp
            900                 905                 910

Gly Ile Asn Lys Asp Gly Thr Asn Lys Ser Gly Glu Val Leu Thr Ser
        915                 920                 925

Val Arg Phe Gly Lys Asp Ile Met Asp Ala Gln Gly Gln Gly Thr Ala
    930                 935                 940

Glu Ser Arg Asn Gln Gly Ile Gly Val Ile Val Ser Asn Ser Ser Gly
945                 950                 955                 960

Leu Glu Leu Lys Asn Ser Asp Ser Ile Thr Leu His Met Gly Ile Ala
                965                 970                 975

His Lys Asn Gln Ala Tyr Arg Ala Leu Met Leu Thr Asn Asp Lys Gly
            980                 985                 990

Ile Val Asn Tyr Asp Gln Asp Asn  Asn Ala Pro Ile Ala  Trp Thr Asn
        995                 1000                 1005

Asp His  Gly Asp Leu Ile Phe  Thr Asn Gln Met Ile  Asn Gly Gln
    1010                 1015                 1020

Ser Asp  Thr Ala Val Lys Gly  Tyr Leu Asn Pro Glu  Val Ala Gly
    1025                 1030                 1035

Tyr Leu  Ala Val Trp Val Pro  Val Gly Ala Asn Asp  Asn Gln Asp
    1040                 1045                 1050

Ala Arg  Thr Val Thr Thr Asn  Gln Lys Asn Thr Asp  Gly Lys Val
    1055                 1060                 1065

Leu His  Thr Asn Ala Ala Leu  Asp Ser Lys Leu Met  Tyr Glu Gly
    1070                 1075                 1080

Phe Ser  Asn Phe Gln Lys Met  Pro Thr Arg Gly Asn  Gln Tyr Ala
    1085                 1090                 1095

Asn Val  Val Ile Thr Lys Asn  Ile Asp Leu Phe Lys  Ser Trp Gly
    1100                 1105                 1110

Ile Thr  Asp Phe Glu Leu Ala  Pro Gln Tyr Arg Ser  Ser Asp Gly
    1115                 1120                 1125

Lys Asp  Ile Thr Asp Arg Phe  Leu Asp Ser Ile Val  Gln Asn Gly
    1130                 1135                 1140

Tyr Gly  Leu Ser Asp Arg Tyr  Asp Leu Gly Phe Lys  Thr Pro Thr
    1145                 1150                 1155

Lys Tyr  Gly Thr Asp Gln Asp  Leu Arg Lys Ala Ile  Glu Arg Leu
    1160                 1165                 1170

His Gln  Ala Gly Met Ser Val  Met Ala Asp Phe Val  Ala Asn Gln
    1175                 1180                 1185

Ile Tyr  Gly Leu His Ala Asp  Lys Glu Val Val Ser  Ala Gln His
    1190                 1195                 1200

Val Asn  Ile Asn Gly Asp Thr  Lys Leu Val Val Asp  Pro Arg Tyr
    1205                 1210                 1215

Gly Thr  Gln Met Thr Val Val  Asn Ser Val Gly Gly  Gly Asp Tyr
```

-continued

```
        1220            1225            1230

Gln Ala Lys Tyr Gly Gly Glu  Tyr Leu Asp Thr Ile  Ser Lys Leu
    1235            1240            1245

Tyr Pro Gly Leu Leu Leu Asp  Ser Asn Gly Gln Lys  Ile Asp Leu
    1250            1255            1260

Ser Thr Lys Ile Lys Glu Trp  Ser Ala Lys Tyr Leu  Asn Gly Ser
    1265            1270            1275

Asn Ile Pro Gln Val Gly Met  Gly Tyr Val Leu Lys  Asp Trp Asn
    1280            1285            1290

Asn Gly Gln Tyr Phe His Ile  Leu Asp Lys Glu Gly  Gln Tyr Ser
    1295            1300            1305

Leu Pro Thr Gln Leu Val Ser  Asn Asp Pro Glu Thr  Gln Ile Gly
    1310            1315            1320

Glu Ser Val Asn Tyr Lys Tyr  Phe Ile Gly Asn Ser  Asp Ala Thr
    1325            1330            1335

Tyr Asn Met Tyr His Asn Leu  Pro Asn Thr Val Ser  Leu Ile Asn
    1340            1345            1350

Ser Gln Glu Gly Gln Ile Lys  Thr Gln Gln Ser Gly  Val Thr Ser
    1355            1360            1365

Asp Tyr Glu Gly Gln Gln Val  Gln Val Thr Arg Gln  Tyr Thr Asp
    1370            1375            1380

Ser Lys Gly Val Ser Trp Asn  Leu Ile Thr Phe Ala  Gly Gly Asp
    1385            1390            1395

Leu Gln Gly Gln Lys Leu Trp  Val Asp Ser Arg Ala  Leu Thr Met
    1400            1405            1410

Thr Pro Phe Lys Thr Met Asn  Gln Ile Ser Phe Ile  Ser Tyr Ala
    1415            1420            1425

Asn Arg Asn Asp Gly Leu Phe  Leu Asn Ala Pro Tyr  Gln Val Lys
    1430            1435            1440

Gly Tyr Gln Leu Ala Gly Met  Ser Asn Gln Tyr Lys  Gly Gln Gln
    1445            1450            1455

Val Thr Ile Ala Gly Val Ala  Asn Val Ser Gly Lys  Asp Trp Ser
    1460            1465            1470

Leu Ile Ser Phe Asn Gly Thr  Gln Tyr Trp Ile Asp  Ser Gln Ala
    1475            1480            1485

Leu Asn Thr Asn Phe Thr His  Asp Met Asn Gln Lys  Val Phe Val
    1490            1495            1500

Asn Thr Thr Ser Asn Leu Asp  Gly Leu Phe Leu Asn  Ala Pro Tyr
    1505            1510            1515

Arg Gln Pro Gly Tyr Lys Leu  Ala Gly Leu Ala Lys  Asn Tyr Asn
    1520            1525            1530

Asn Gln Thr Val Thr Val Ser  Gln Gln Tyr Phe Asp  Asp Gln Gly
    1535            1540            1545

Thr Val Trp Ser Glu Val Val  Leu Gly Gly Gln Thr  Val Trp Val
    1550            1555            1560

Asp Asn His Ala Leu Ala Gln  Met Gln Val Ser Asp  Thr Ser Gln
    1565            1570            1575

Gln Leu Tyr Val Asn Ser Asn  Gly Arg Asn Asp Gly  Leu Phe Leu
    1580            1585            1590

Asn Ala Pro Tyr Arg Gly Gln  Gly Ser Gln Leu Ile  Gly Met Thr
    1595            1600            1605

Ala Asp Tyr Asn Gly Gln His  Val Gln Val Thr Lys  Gln Gly Gln
    1610            1615            1620
```

-continued

```
Asp Ala  Tyr Gly Ala Gln Trp  Arg Leu Ile Thr Leu  Asn Asn Gln
    1625                1630                1635

Gln Val  Trp Val Asp Ser Arg  Ala Leu Ser Thr Thr  Ile Val Gln
    1640                1645                1650

Ala Met  Asn Asp Asp Met Tyr  Val Asn Ser Asn Gln  Arg Thr Asp
    1655                1660                1665

Gly Leu  Trp Leu Asn Ala Pro  Tyr Thr Met Ser Gly  Ala Lys Trp
    1670                1675                1680

Ala Gly  Asp Thr Arg Ser Ala  Asn Gly Arg Tyr Val  His Ile Ser
    1685                1690                1695

Lys Ala  Tyr Ser Asn Glu Val  Gly Asn Thr Tyr Tyr  Leu Thr Asn
    1700                1705                1710

Leu Asn  Gly Gln Ser Thr Trp  Ile Asp Lys Arg Ala  Phe Thr Ala
    1715                1720                1725

Thr Phe  Asp Gln Val Val Ala  Leu Asn Ala Thr Ile  Val Ala Arg
    1730                1735                1740

Gln Arg  Pro Asp Gly Met Phe  Lys Thr Ala Pro Tyr  Gly Glu Ala
    1745                1750                1755

Gly Ala  Gln Phe Val Asp Tyr  Val Thr Asn Tyr Asn  Gln Gln Thr
    1760                1765                1770

Val Pro  Val Thr Lys Gln His  Ser Asp Ala Gln Gly  Asn Gln Trp
    1775                1780                1785

Tyr Leu  Ala Thr Val Asn Gly  Thr Gln Tyr Trp Ile  Asp Gln Arg
    1790                1795                1800

Ser Phe  Ser Pro Val Val Thr  Lys Val Val Asp Tyr  Gln Ala Lys
    1805                1810                1815

Ile Val  Pro Arg Thr Thr Arg  Asp Gly Val Phe Ser  Gly Ala Pro
    1820                1825                1830

Tyr Gly  Glu Val Asn Ala Lys  Leu Val Asn Met Ala  Thr Ala Tyr
    1835                1840                1845

Gln Asn  Gln Val Val His Ala  Thr Gly Glu Tyr Thr  Asn Ala Ser
    1850                1855                1860

Gly Ile  Thr Trp Ser Gln Phe  Ala Leu Ser Gly Gln  Glu Asp Lys
    1865                1870                1875

Leu Trp  Ile Asp Lys Arg Ala  Leu Gln Ala
    1880                1885
```

```
<210> SEQ ID NO 14
<211> LENGTH: 868
<212> TYPE: PRT
<213> ORGANISM: Leuconostoc citreum

<400> SEQUENCE: 14

Val Lys Asp Val Tyr Ser Gln His Asn Ala Val Asn Asn Leu Ser Ala
1               5                   10                  15

Asn Asn Phe Lys Asn Leu Val Asp Gly Phe Leu Thr Ala Glu Thr Trp
            20                  25                  30

Tyr Arg Pro Ala Gln Ile Leu Ser His Gly Thr Asp Trp Val Ala Ser
        35                  40                  45

Thr Asp Lys Asp Phe Arg Pro Leu Ile Thr Val Trp Trp Pro Asn Lys
    50                  55                  60

Asp Ile Gln Val Asn Tyr Leu Lys Leu Met Gln Gln Ile Gly Ile Leu
65                  70                  75                  80

Asp Asn Ser Val Val Phe Asp Thr Asn Asn Asp Gln Leu Val Leu Asn
```

-continued

```
                    85                    90                    95
Lys Gly Ala Glu Ser Ala Gln Ile Gly Ile Glu Lys Lys Val Ser Glu
                100                   105                   110

Thr Gly Asn Thr Asp Trp Leu Asn Glu Leu Leu Phe Ala Pro Asn Gly
                115                   120                   125

Asn Gln Pro Ser Phe Ile Lys Gln Gln Tyr Leu Trp Asn Val Asp Ser
        130                   135                   140

Glu Tyr Pro Gly Gly Trp Phe Gln Gly Gly Tyr Leu Ala Tyr Gln Asn
145                   150                   155                   160

Ser Asp Leu Thr Pro Tyr Ala Asn Thr Asn Pro Asp Tyr Arg Thr His
                165                   170                   175

Asn Gly Leu Glu Phe Leu Leu Ala Asn Asp Val Asp Asn Ser Asn Pro
                180                   185                   190

Val Val Gln Ala Glu Gln Leu Asn Trp Leu Tyr Tyr Leu Met Asn Phe
        195                   200                   205

Gly Gln Ile Thr Ala Asn Asp Ser Asn Ala Asn Phe Asp Ser Met Arg
        210                   215                   220

Ile Asp Ala Ile Ser Phe Val Asp Pro Gln Ile Ala Lys Lys Ala Tyr
225                   230                   235                   240

Asp Leu Leu Asp Lys Met Tyr Gly Leu Thr Asp Asn Glu Ala Val Ala
                245                   250                   255

Asn Gln His Ile Ser Ile Val Glu Ala Pro Lys Gly Glu Thr Pro Ile
                260                   265                   270

Thr Val Glu Lys Gln Ser Ala Leu Val Glu Ser Asn Trp Arg Asp Arg
        275                   280                   285

Met Lys Gln Ser Leu Ser Lys Asn Ala Thr Leu Asp Lys Leu Asp Pro
        290                   295                   300

Asp Pro Ala Ile Asn Ser Leu Glu Lys Leu Val Ala Asp Asp Leu Val
305                   310                   315                   320

Asn Arg Ser Gln Ser Ser Asp Lys Asp Ser Ser Thr Ile Pro Asn Tyr
                325                   330                   335

Ser Ile Val His Ala His Asp Lys Asp Ile Gln Asp Thr Val Ile His
                340                   345                   350

Ile Met Lys Ile Val Asn Asn Asn Pro Asn Ile Ser Met Ser Asp Phe
        355                   360                   365

Thr Met Gln Gln Leu Gln Asn Gly Leu Lys Ala Phe Tyr Glu Asp Gln
        370                   375                   380

His Gln Ser Val Lys Lys Tyr Asn Gln Tyr Asn Ile Pro Ser Ala Tyr
385                   390                   395                   400

Ala Leu Leu Leu Thr Asn Lys Asp Thr Val Pro Arg Val Phe Tyr Gly
                405                   410                   415

Asp Met Tyr Gln Asp Tyr Gly Asp Asp Leu Asp Gly Gly Gln Tyr Met
                420                   425                   430

Ala Thr Lys Ser Ile Tyr Tyr Asn Ala Ile Glu Gln Met Met Lys Ala
        435                   440                   445

Arg Leu Lys Tyr Val Ala Gly Gly Gln Ile Met Ala Val Thr Lys Ile
        450                   455                   460

Lys Asn Asp Gly Ile Asn Lys Asp Gly Thr Asn Lys Ser Gly Glu Val
465                   470                   475                   480

Leu Thr Ser Val Arg Phe Gly Lys Asp Ile Met Asp Ala Gln Gly Gln
                485                   490                   495

Gly Thr Ala Glu Ser Arg Asn Gln Gly Ile Gly Val Ile Val Ser Asn
                500                   505                   510
```

-continued

```
Ser Ser Gly Leu Glu Leu Lys Asn Ser Asp Ser Ile Thr Leu His Met
        515             520             525

Gly Ile Ala His Lys Asn Gln Ala Tyr Arg Ala Leu Met Leu Thr Asn
        530             535             540

Asp Lys Gly Ile Val Asn Tyr Asp Gln Asp Asn Asn Ala Pro Ile Ala
545             550             555             560

Trp Thr Asn Asp His Gly Asp Leu Ile Phe Thr Asn Gln Met Ile Asn
        565             570             575

Gly Gln Ser Asp Thr Ala Val Lys Gly Tyr Leu Asn Pro Glu Val Ala
        580             585             590

Gly Tyr Leu Ala Val Trp Val Pro Val Gly Ala Asn Asp Asn Gln Asp
        595             600             605

Ala Arg Thr Val Thr Thr Asn Gln Lys Asn Thr Asp Gly Lys Val Leu
        610             615             620

His Thr Asn Ala Ala Leu Asp Ser Lys Leu Met Tyr Glu Gly Phe Ser
625             630             635             640

Asn Phe Gln Lys Met Pro Thr Arg Gly Asn Gln Tyr Ala Asn Val Val
        645             650             655

Ile Thr Lys Asn Ile Asp Leu Phe Lys Ser Trp Gly Ile Thr Asp Phe
        660             665             670

Glu Leu Ala Pro Gln Tyr Arg Ser Ser Asp Gly Lys Asp Ile Thr Asp
        675             680             685

Arg Phe Leu Asp Ser Ile Val Gln Asn Gly Tyr Gly Leu Ser Asp Arg
        690             695             700

Tyr Asp Leu Gly Phe Lys Thr Pro Thr Lys Tyr Gly Thr Asp Gln Asp
705             710             715             720

Leu Arg Lys Ala Ile Glu Arg Leu His Gln Ala Gly Met Ser Val Met
        725             730             735

Ala Asp Phe Val Ala Asn Gln Ile Tyr Gly Leu His Ala Asp Lys Glu
        740             745             750

Val Val Ser Ala Gln His Val Asn Ile Asn Gly Asp Thr Lys Leu Val
        755             760             765

Val Asp Pro Arg Tyr Gly Thr Gln Met Thr Val Val Asn Ser Val Gly
        770             775             780

Gly Gly Asp Tyr Gln Ala Lys Tyr Gly Gly Glu Tyr Leu Asp Thr Ile
785             790             795             800

Ser Lys Leu Tyr Pro Gly Leu Leu Leu Asp Ser Asn Gly Gln Lys Ile
        805             810             815

Asp Leu Ser Thr Lys Ile Lys Glu Trp Ser Ala Lys Tyr Leu Asn Gly
        820             825             830

Ser Asn Ile Pro Gln Val Gly Met Gly Tyr Val Leu Lys Asp Trp Asn
        835             840             845

Asn Gly Gln Tyr Phe His Ile Leu Asp Lys Glu Gly Gln Tyr Ser Leu
        850             855             860

Pro Thr Gln Leu
865

<210> SEQ ID NO 15
<211> LENGTH: 1849
<212> TYPE: PRT
<213> ORGANISM: Leuconostoc citreum

<400> SEQUENCE: 15

Asp Thr Gln Thr Pro Val Gly Thr Thr Gln Ser Gln Gln Asp Leu Thr
```

-continued

```
 1                5                    10                   15

Gly Gln Thr Gly Gln Asp Lys Pro Thr Thr Lys Glu Val Ile Asp Lys
             20                  25                  30

Lys Glu Pro Val Pro Gln Val Ser Ala Gln Asn Val Gly Asp Leu Ser
             35                  40                  45

Ala Asp Ala Lys Thr Pro Lys Ala Asp Asp Lys Gln Asp Thr Gln Pro
 50                  55                  60

Thr Asn Ala Gln Leu Pro Asp Gln Gly Asn Lys Gln Thr Asn Ser Asn
 65                  70                  75                  80

Ser Asp Lys Gly Val Lys Glu Ser Thr Thr Ala Pro Val Lys Thr Thr
             85                  90                  95

Asp Val Pro Ser Lys Ser Val Ala Pro Glu Thr Asn Thr Ser Ile Asn
             100                 105                 110

Gly Gly Gln Tyr Val Glu Lys Asp Gly Gln Phe Val Tyr Ile Asp Gln
             115                 120                 125

Ser Gly Lys Gln Val Ser Gly Leu Gln Asn Ile Glu Gly His Thr Gln
             130                 135                 140

Tyr Phe Asp Pro Lys Thr Gly Tyr Gln Thr Lys Gly Glu Leu Lys Asn
 145                 150                 155                 160

Ile Asp Asp Asn Ala Tyr Tyr Phe Asp Lys Asn Ser Gly Asn Gly Arg
             165                 170                 175

Thr Phe Thr Lys Ile Ser Asn Gly Ser Tyr Ser Glu Lys Asp Gly Met
             180                 185                 190

Trp Gln Tyr Val Asp Ser His Asp Lys Gln Pro Val Lys Gly Leu Tyr
             195                 200                 205

Asp Val Glu Gly Asn Leu Gln Tyr Phe Asp Leu Ser Thr Gly Asn Gln
             210                 215                 220

Ala Lys His Gln Ile Arg Ser Val Asp Gly Val Thr Tyr Tyr Phe Asp
 225                 230                 235                 240

Ala Asp Ser Gly Asn Ala Thr Ala Phe Lys Ala Val Thr Asn Gly Arg
             245                 250                 255

Tyr Ala Glu Gln Thr Thr Lys Asp Lys Asp Gly Asn Glu Thr Ser Tyr
             260                 265                 270

Trp Ala Tyr Leu Asp Asn Gln Gly Asn Ala Ile Lys Gly Leu Asn Asp
             275                 280                 285

Val Asn Gly Glu Ile Gln Tyr Phe Asp Glu His Thr Gly Glu Gln Leu
             290                 295                 300

Lys Gly His Thr Ala Thr Val Asp Gly Thr Thr Tyr Tyr Phe Glu Gly
 305                 310                 315                 320

Asn Lys Gly Asn Leu Val Ser Val Val Asn Thr Ala Pro Thr Gly Gln
             325                 330                 335

Tyr Lys Ile Asn Gly Asp Asn Val Tyr Tyr Leu Asp Asn Asn Asn Glu
             340                 345                 350

Ala Ile Lys Gly Leu Tyr Gly Ile Asn Gly Asn Leu Asn Tyr Phe Asp
             355                 360                 365

Leu Ala Thr Gly Ile Gln Leu Lys Gly Gln Ala Lys Asn Ile Asp Gly
             370                 375                 380

Ile Gly Tyr Tyr Phe Asp Gln Asn Asn Gly Asn Gly Glu Tyr Arg Tyr
 385                 390                 395                 400

Ser Leu Thr Gly Pro Val Val Lys Asp Val Tyr Ser Gln His Asn Ala
             405                 410                 415

Val Asn Asn Leu Ser Ala Asn Asn Phe Lys Asn Leu Val Asp Gly Phe
             420                 425                 430
```

```
Leu Thr Ala Glu Thr Trp Tyr Arg Pro Ala Gln Ile Leu Ser His Gly
        435                 440                 445

Thr Asp Trp Val Ala Ser Thr Asp Lys Asp Phe Arg Pro Leu Ile Thr
        450                 455                 460

Val Trp Trp Pro Asn Lys Asp Ile Gln Val Asn Tyr Leu Lys Leu Met
465                 470                 475                 480

Gln Gln Ile Gly Ile Leu Asp Asn Ser Val Val Phe Asp Thr Asn Asn
                485                 490                 495

Asp Gln Leu Val Leu Asn Lys Gly Ala Glu Ser Ala Gln Ile Gly Ile
                500                 505                 510

Glu Lys Lys Val Ser Glu Thr Gly Asn Thr Asp Trp Leu Asn Glu Leu
                515                 520                 525

Leu Phe Ala Pro Asn Gly Asn Gln Pro Ser Phe Ile Lys Gln Gln Tyr
        530                 535                 540

Leu Trp Asn Val Asp Ser Glu Tyr Pro Gly Gly Trp Phe Gln Gly Gly
545                 550                 555                 560

Tyr Leu Ala Tyr Gln Asn Ser Asp Leu Thr Pro Tyr Ala Asn Thr Asn
                565                 570                 575

Pro Asp Tyr Arg Thr His Asn Gly Leu Glu Phe Leu Leu Ala Asn Asp
                580                 585                 590

Val Asp Asn Ser Asn Pro Val Val Gln Ala Glu Gln Leu Asn Trp Leu
                595                 600                 605

Tyr Tyr Leu Met Asn Phe Gly Gln Ile Thr Ala Asn Asp Ser Asn Ala
        610                 615                 620

Asn Phe Asp Ser Met Arg Ile Asp Ala Ile Ser Phe Val Asp Pro Gln
625                 630                 635                 640

Ile Ala Lys Lys Ala Tyr Asp Leu Leu Asp Lys Met Tyr Gly Leu Thr
                645                 650                 655

Asp Asn Glu Ala Val Ala Asn Gln His Ile Ser Ile Val Glu Ala Pro
                660                 665                 670

Lys Gly Glu Thr Pro Ile Thr Val Glu Lys Gln Ser Ala Leu Val Glu
                675                 680                 685

Ser Asn Trp Arg Asp Arg Met Lys Gln Ser Leu Ser Lys Asn Ala Thr
        690                 695                 700

Leu Asp Lys Leu Asp Pro Asp Pro Ala Ile Asn Ser Leu Glu Lys Leu
705                 710                 715                 720

Val Ala Asp Asp Leu Val Asn Arg Ser Gln Ser Ser Asp Lys Asp Ser
                725                 730                 735

Ser Thr Ile Pro Asn Tyr Ser Ile Val His Ala His Asp Lys Asp Ile
                740                 745                 750

Gln Asp Thr Val Ile His Ile Met Lys Ile Val Asn Asn Asn Pro Asn
                755                 760                 765

Ile Ser Met Ser Asp Phe Thr Met Gln Gln Leu Gln Asn Gly Leu Lys
        770                 775                 780

Ala Phe Tyr Glu Asp Gln His Gln Ser Val Lys Lys Tyr Asn Gln Tyr
785                 790                 795                 800

Asn Ile Pro Ser Ala Tyr Ala Leu Leu Leu Thr Asn Lys Asp Thr Val
                805                 810                 815

Pro Arg Val Phe Tyr Gly Asp Met Tyr Gln Asp Tyr Gly Asp Asp Leu
                820                 825                 830

Asp Gly Gly Gln Tyr Met Ala Thr Lys Ser Ile Tyr Tyr Asn Ala Ile
        835                 840                 845
```

-continued

```
Glu Gln Met Met Lys Ala Arg Leu Lys Tyr Val Ala Gly Gly Gln Ile
    850             855             860

Met Ala Val Thr Lys Ile Lys Asn Asp Gly Ile Asn Lys Asp Gly Thr
865             870             875             880

Asn Lys Ser Gly Glu Val Leu Thr Ser Val Arg Phe Gly Lys Asp Ile
            885             890             895

Met Asp Ala Gln Gly Gln Gly Thr Ala Glu Ser Arg Asn Gln Gly Ile
        900             905             910

Gly Val Ile Val Ser Asn Ser Ser Gly Leu Glu Leu Lys Asn Ser Asp
        915             920             925

Ser Ile Thr Leu His Met Gly Ile Ala His Lys Asn Gln Ala Tyr Arg
    930             935             940

Ala Leu Met Leu Thr Asn Asp Lys Gly Ile Val Asn Tyr Asp Gln Asp
945             950             955             960

Asn Asn Ala Pro Ile Ala Trp Thr Asn Asp His Gly Asp Leu Ile Phe
            965             970             975

Thr Asn Gln Met Ile Asn Gly Gln Ser Asp Thr Ala Val Lys Gly Tyr
        980             985             990

Leu Asn Pro Glu Val Ala Gly Tyr  Leu Ala Val Trp Val  Pro Val Gly
        995             1000             1005

Ala Asn  Asp Asn Gln Asp Ala  Arg Thr Val Thr Thr  Asn Gln Lys
    1010             1015             1020

Asn Thr  Asp Gly Lys Val Leu  His Thr Asn Ala Ala  Leu Asp Ser
    1025             1030             1035

Lys Leu  Met Tyr Glu Gly Phe  Ser Asn Phe Gln Lys  Met Pro Thr
    1040             1045             1050

Arg Gly  Asn Gln Tyr Ala Asn  Val Val Ile Thr Lys  Asn Ile Asp
    1055             1060             1065

Leu Phe  Lys Ser Trp Gly Ile  Thr Asp Phe Glu Leu  Ala Pro Gln
    1070             1075             1080

Tyr Arg  Ser Ser Asp Gly Lys  Asp Ile Thr Asp Arg  Phe Leu Asp
    1085             1090             1095

Ser Ile  Val Gln Asn Gly Tyr  Gly Leu Ser Asp Arg  Tyr Asp Leu
    1100             1105             1110

Gly Phe  Lys Thr Pro Thr Lys  Tyr Gly Thr Asp Gln  Asp Leu Arg
    1115             1120             1125

Lys Ala  Ile Glu Arg Leu His  Gln Ala Gly Met Ser  Val Met Ala
    1130             1135             1140

Asp Phe  Val Ala Asn Gln Ile  Tyr Gly Leu His Ala  Asp Lys Glu
    1145             1150             1155

Val Val  Ser Ala Gln His Val  Asn Ile Asn Gly Asp  Thr Lys Leu
    1160             1165             1170

Val Val  Asp Pro Arg Tyr Gly  Thr Gln Met Thr Val  Val Asn Ser
    1175             1180             1185

Val Gly  Gly Gly Asp Tyr Gln  Ala Lys Tyr Gly Gly  Glu Tyr Leu
    1190             1195             1200

Asp Thr  Ile Ser Lys Leu Tyr  Pro Gly Leu Leu Leu  Asp Ser Asn
    1205             1210             1215

Gly Gln  Lys Ile Asp Leu Ser  Thr Lys Ile Lys Glu  Trp Ser Ala
    1220             1225             1230

Lys Tyr  Leu Asn Gly Ser Asn  Ile Pro Gln Val Gly  Met Gly Tyr
    1235             1240             1245

Val Leu  Lys Asp Trp Asn Asn  Gly Gln Tyr Phe His  Ile Leu Asp
```

```
    1250              1255              1260

Lys Glu Gly Gln Tyr Ser Leu Pro Thr Gln Leu Val Ser Asn Asp
    1265              1270              1275

Pro Glu Thr Gln Ile Gly Glu Ser Val Asn Tyr Lys Tyr Phe Ile
    1280              1285              1290

Gly Asn Ser Asp Ala Thr Tyr Asn Met Tyr His Asn Leu Pro Asn
    1295              1300              1305

Thr Val Ser Leu Ile Asn Ser Gln Glu Gly Gln Ile Lys Thr Gln
    1310              1315              1320

Gln Ser Gly Val Thr Ser Asp Tyr Glu Gly Gln Gln Val Gln Val
    1325              1330              1335

Thr Arg Gln Tyr Thr Asp Ser Lys Gly Val Ser Trp Asn Leu Ile
    1340              1345              1350

Thr Phe Ala Gly Gly Asp Leu Gln Gly Gln Lys Leu Trp Val Asp
    1355              1360              1365

Ser Arg Ala Leu Thr Met Thr Pro Phe Lys Thr Met Asn Gln Ile
    1370              1375              1380

Ser Phe Ile Ser Tyr Ala Asn Arg Asn Asp Gly Leu Phe Leu Asn
    1385              1390              1395

Ala Pro Tyr Gln Val Lys Gly Tyr Gln Leu Ala Gly Met Ser Asn
    1400              1405              1410

Gln Tyr Lys Gly Gln Gln Val Thr Ile Ala Gly Val Ala Asn Val
    1415              1420              1425

Ser Gly Lys Asp Trp Ser Leu Ile Ser Phe Asn Gly Thr Gln Tyr
    1430              1435              1440

Trp Ile Asp Ser Gln Ala Leu Asn Thr Asn Phe Thr His Asp Met
    1445              1450              1455

Asn Gln Lys Val Phe Val Asn Thr Thr Ser Asn Leu Asp Gly Leu
    1460              1465              1470

Phe Leu Asn Ala Pro Tyr Arg Gln Pro Gly Tyr Lys Leu Ala Gly
    1475              1480              1485

Leu Ala Lys Asn Tyr Asn Asn Gln Thr Val Thr Val Ser Gln Gln
    1490              1495              1500

Tyr Phe Asp Asp Gln Gly Thr Val Trp Ser Glu Val Val Leu Gly
    1505              1510              1515

Gly Gln Thr Val Trp Val Asp Asn His Ala Leu Ala Gln Met Gln
    1520              1525              1530

Val Ser Asp Thr Ser Gln Gln Leu Tyr Val Asn Ser Asn Gly Arg
    1535              1540              1545

Asn Asp Gly Leu Phe Leu Asn Ala Pro Tyr Arg Gly Gln Gly Ser
    1550              1555              1560

Gln Leu Ile Gly Met Thr Ala Asp Tyr Asn Gly Gln His Val Gln
    1565              1570              1575

Val Thr Lys Gln Gly Gln Asp Ala Tyr Gly Ala Gln Trp Arg Leu
    1580              1585              1590

Ile Thr Leu Asn Asn Gln Gln Val Trp Val Asp Ser Arg Ala Leu
    1595              1600              1605

Ser Thr Thr Ile Val Gln Ala Met Asn Asp Asp Met Tyr Val Asn
    1610              1615              1620

Ser Asn Gln Arg Thr Asp Gly Leu Trp Leu Asn Ala Pro Tyr Thr
    1625              1630              1635

Met Ser Gly Ala Lys Trp Ala Gly Asp Thr Arg Ser Ala Asn Gly
    1640              1645              1650
```

-continued

```
Arg Tyr  Val His Ile Ser Lys  Ala Tyr Ser Asn Glu  Val Gly Asn
    1655             1660             1665

Thr Tyr  Tyr Leu Thr Asn Leu  Asn Gly Gln Ser Thr  Trp Ile Asp
    1670             1675             1680

Lys Arg  Ala Phe Thr Ala Thr  Phe Asp Gln Val Val  Ala Leu Asn
    1685             1690             1695

Ala Thr  Ile Val Ala Arg Gln  Arg Pro Asp Gly Met  Phe Lys Thr
    1700             1705             1710

Ala Pro  Tyr Gly Glu Ala Gly  Ala Gln Phe Val Asp  Tyr Val Thr
    1715             1720             1725

Asn Tyr  Asn Gln Gln Thr Val  Pro Val Thr Lys Gln  His Ser Asp
    1730             1735             1740

Ala Gln  Gly Asn Gln Trp Tyr  Leu Ala Thr Val Asn  Gly Thr Gln
    1745             1750             1755

Tyr Trp  Ile Asp Gln Arg Ser  Phe Ser Pro Val Val  Thr Lys Val
    1760             1765             1770

Val Asp  Tyr Gln Ala Lys Ile  Val Pro Arg Thr Thr  Arg Asp Gly
    1775             1780             1785

Val Phe  Ser Gly Ala Pro Tyr  Gly Glu Val Asn Ala  Lys Leu Val
    1790             1795             1800

Asn Met  Ala Thr Ala Tyr Gln  Asn Gln Val Val His  Ala Thr Gly
    1805             1810             1815

Glu Tyr  Thr Asn Ala Ser Gly  Ile Thr Trp Ser Gln  Phe Ala Leu
    1820             1825             1830

Ser Gly  Gln Glu Asp Lys Leu  Trp Ile Asp Lys Arg  Ala Leu Gln
    1835             1840             1845

Ala
```

ENGINEERED ALPHA-1,3 BRANCHING ENZYMES

This application is a National Stage application of International Application No. PCT/US2020/041093 (filed Jul. 8, 2020), which claims the benefit of U.S. Provisional Application No. 62/871,796 (filed Jul. 9, 2019), both of which prior applications are incorporated herein by reference in their entirety.

FIELD

The present disclosure is in the field of enzyme catalysis. For example, the disclosure pertains to alpha-1,3 branching enzymes with modified amino acid sequences. Such modified enzymes can be used to synthesize glucan products with at least one alpha-1,3 branch, for example.

REFERENCE TO SEQUENCE LISTING SUBMITTED ELECTRONICALLY

The official copy of the sequence listing is submitted electronically via EFS-Web as an ASCII formatted sequence listing with a file named 20200702_CL6645PCT_SequenceListing.txt created on Jul. 2, 2020, and having a size of about 91000 bytes and is filed concurrently with the specification. The sequence listing contained in this ASCII-formatted document is part of the specification and is herein incorporated by reference in its entirety.

BACKGROUND

The enzymatic addition of alpha-1,3 branches to acceptor molecules has been reported. Early biochemical studies of *Leuconostoc mesenteroides* and *Streptococcus mutans* suggested that alpha-1,3-branching enzymes exist and play a role, for example, in branching of exopolysaccharides (e.g., Vote and Robyt, 1983, *Carb. Res.* 119:141-156; Remaud et al., 1992, *J. Carb. Chem.* 11:359-378; Walker, 1980, *Carb. Res.* 82:404-410). More recently, Vuillemin et al. (2016, *J. Biol. Chem.* 14:7687-7702) and Remaud-Simeon et al. (U.S. Patent Appl. Publ. No. 2016/0136199) directly identified alpha-1,3-branching enzymes from *Leuconostoc citreum* and *Leuconostoc fallax* and use thereof to introduce alpha-1,3 branches to dextran. These enzymes were characterized as members of the GH70 family of glucosyltransferases (sucrases), which include enzymes with other activities such as alpha-1,2-branching or alpha-glucan polymerization (Vuillemin et al., ibid.).

While advances have been made in understanding and using alpha-1,3-branching enzymes, less attention appears to have been drawn to modulating the activity of these enzymes. Such modulated enzymes could prove to be a valuable tool for providing glucan products with defined structure for specific applications. Addressing this technological gap, disclosed herein are alpha-1,3-branching enzymes with modified amino acid sequences that have altered alpha-1,3-branching activity.

SUMMARY

In one embodiment, the present disclosure concerns a composition comprising a non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, wherein the non-native glucosyltransferase is capable of forming at least one alpha-1,3 branch from an acceptor molecule.

In another embodiment, the present disclosure concerns a polynucleotide comprising a nucleotide sequence encoding a non-native glucosyltransferase as disclosed herein, optionally wherein one or more regulatory sequences are operably linked to the nucleotide sequence, and preferably wherein the one or more regulatory sequences include a promoter sequence.

In another embodiment, the present disclosure concerns a reaction composition comprising water, sucrose, an acceptor molecule, and a non-native glucosyltransferase as disclosed herein.

In another embodiment, the present disclosure concerns a method of producing a glucan composition that comprises at least one alpha-1,3 branch, the method comprising: (a) contacting at least water, sucrose, a glucan substrate, and a non-native glucosyltransferase enzyme according to claim 1, whereby a glucan composition comprising at least one alpha-1,3 branch is produced; and (b) optionally isolating the glucan composition produced in step (a).

In another embodiment, the present disclosure concerns a method of preparing a polynucleotide sequence encoding a non-native glucosyltransferase, the method comprising: (a) identifying a polynucleotide sequence encoding a parent glucosyltransferase that (i) comprises an amino acid sequence that is at least about 40% identical to SEQ ID NO:3 or positions 477-1322 of SEQ ID NO:2, and (ii) is capable of forming at least one alpha-1,3 branch from an acceptor molecule; and (b) modifying the polynucleotide sequence identified in step (a) to substitute at least one amino acid of the parent glucosyltransferase at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, thereby providing a polynucleotide sequence encoding a non-native glucosyltransferase that forms at least one alpha-1,3 branch from an acceptor molecule.

TABLE 1

| BRIEF DESCRIPTION OF THE SEQUENCES Summary of Nucleic Acid and Protein SEQ ID Numbers | | |
|---|---|---|
| Description | Nucleic acid SEQ ID NO. | Protein SEQ ID NO. |
| GTF 2592, *Leuconostoc fallax*. The first 39 amino acid residues (which includes most of predicted signal peptide) of the protein are deleted compared to GENBANK Accession No. WP_010006776.1 (Identification No. 497692592). A start methionine and C-terminal 6xHis tag are included. | 1 | 2 (1742 aa) |

TABLE 1-continued

BRIEF DESCRIPTION OF THE SEQUENCES
Summary of Nucleic Acid and Protein SEQ ID Numbers

| Description | Nucleic acid SEQ ID NO. | Protein SEQ ID NO. |
|---|---|---|
| GTF 2592, *Leuconostoc fallax*. Represents SEQ ID NO: 2 without start methionine and C-terminal 6xHis tag. | | 3 (1668 aa) |
| Full-length (immature), wild type GTF corresponding to GTF 2592, *Leuconostoc fallax*, including predicted signal peptide (residues 1-45). | | 4 (1774 aa) |
| GTF 2592 conserved motif I (ADYVANQ). | | 5 (7 aa) |
| GTF 2592 conserved motif II (SIRIDAISFVD). | | 6 (11 aa) |
| GTF 2592 conserved motif III (HVSIVEASADQ). | | 7 (11 aa) |
| GTF 2592 conserved motif IV (IVHAHDKDIQDAVSN). | | 8 (15 aa) |
| Alpha-1,3-branching enzyme conserved motif I (ADXVANQ, X is F or Y). | | 9 (7 aa) |
| Alpha-1,3-branching enzyme conserved motif II (SXRIDAISFVD, X is M or I). | | 10 (11 aa) |
| Alpha-1,3-branching enzyme conserved motif III (HX$_1$SIVEAX$_2$X$_3$X$_4$X$_5$, X$_1$ is V or I, X$_2$ is P or S, X$_3$ is K or A, X$_4$ is G or D, X$_5$ represents E or Q). | | 11 (11 aa) |
| Alpha-1,3-branching enzyme conserved motif IV (IVHAHDKDIQDX$_1$VX$_2$X$_3$, X$_1$ is T or A, X$_2$ is S or I, and X$_3$ is H or N). | | 12 (15 aa) |
| GTF BRS-B, *Leuconostoc citreum*, full-length (immature), wild type sequence, including predicted signal peptide (residues 1-39). | | 13 (1888 aa) |
| GTF BRS-B-Δ1, *L. citreum*, represents residues 446-1313 of BRS-B (SEQ ID NO: 13). | | 14 (868 aa) |
| GTF BRS-B, L. citreum, mature, wild type sequence (i.e., without signal peptide). | | 15 (1849 aa) |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The term "saccharide" and other like terms herein refer to monosaccharides and/or disaccharides/oligosaccharides, unless otherwise noted. A "disaccharide" herein refers to a carbohydrate having two monosaccharides joined by a glycosidic linkage. An "oligosaccharide" herein can refer to a carbohydrate having 3 to 15 monosaccharides, for example, joined by glycosidic linkages. An oligosaccharide can also be referred to as an "oligomer". Monosaccharides (e.g., glucose and/or fructose) comprised within disaccharides/ oligosaccharides (or any larger glucan polymer) can be referred to as "monomeric units", "monosaccharide units", "glycosyl groups", or other like terms.

The terms "glucan", "glucan polymer" and the like herein refer to a glucose polymer (i.e., polyglucose) in which the constituent glucose monomeric units (glucosyl groups) are linked by glycosidic linkages. Examples of glucan herein include alpha-glucan (e.g., dextran, glucan with mixed alpha-1,3 and -1,6 linkages, alternan [glucan with alternating alpha-1,3 and -1,6 linkages], starch/amylose, reuteran) and beta-glucan (e.g., beta-1,3-glucan, beta-1,6-glucan, cellulose). "Alpha-glucan" and like terms herein refer to a glucan comprising glucose monomeric units linked together by alpha-glycosidic linkages. In typical embodiments, at least about 80%, 81%, 82%, 83%, 84%, 85%, 86%, 87%, 88%, 89%, 90%, 91%, 92%, 93%, 94%, 95%, 96%, 97%, 98%, 99%, or 100% of the linkages of an alpha-glucan herein are alpha-glycosidic linkages. "Beta-glucan" and like terms herein refer to a glucan comprising glucose monomeric units linked together by beta-glycosidic linkages. In typical embodiments, at least about 80%, 81%, 82%, 83%, 84%, 85%, 86%, 87%, 88%, 89%, 90%, 91%, 92%, 93%, 94%, 95%, 96%, 97%, 98%, 99%, or 100% of the linkages of a beta-glucan herein are beta-glycosidic linkages.

The terms "dextran", "dextran polymer", "dextran molecule" and the like herein refer to a water-soluble alpha-glucan comprising at least 50% alpha-1,6 glycosidic linkages (with the balance of the linkages typically being alpha-1,3). Enzymes capable of synthesizing dextran from sucrose may be described as "dextransucrases" (EC 2.4.1.5).

A "substantially linear" dextran herein has 5% or less branches, before optionally being modified to contain alpha-1,3 branches. A "completely linear" dextran has no branches, before optionally being modified to contain alpha-1,3 branches. Dextran branches, if present prior to modification with alpha-1,3 branches, typically are short, being one (pendant) to three glucose monomers in length, and comprise less than about 10% of all the glucose monomers of a dextran polymer.

The terms "linkage", "glycosidic linkage", "glycosidic bond" and the like herein refer to the covalent bonds connecting the sugar monomers within a saccharide compound (e.g., oligosaccharides, polysaccharides). Examples of glycosidic linkages herein are alpha- and beta-glycosidic linkages. Examples of alpha-glycosidic linkages herein include 1,6-alpha-D-glycosidic linkages, 1,3-alpha-D-glycosidic linkages, 1,4-alpha-D-glycosidic linkages, and 1,2-alpha-D-glycosidic linkages, which are herein also referred to as, respectively, alpha-1,6 linkages, alpha-1,3 linkages, alpha-1,4 linkages, and alpha-1,2 linkages. The glycosidic linkages of a glucan polymer herein can also be referred to as "glucosidic linkages". Herein, "alpha-D-glucose" is referred to as "glucose".

An "alpha-1,3 branch" (and like terms) herein comprises a glucose unit that is alpha-1,3-linked to a glucan; such a glucan can optionally be referred to as a backbone herein. Typically, to be considered a "branch" herein, the backbone glucose unit to which the branch glucose unit is linked is not a non-reducing end glucose unit (i.e., a branch herein typically is not a linkage to a non-reducing end of a glucan). Herein, "alpha-1,3,6" refers to a branch point in which the branch glucose is alpha-1,3-linked to an alpha-1,6-linked glucose monomer of a backbone (e.g., dextran). Herein, "alpha-1,3,4" refers to a branch point in which the branch glucose is alpha-1,3-linked to an alpha-1,4-linked glucose monomer of a backbone (e.g., starch or amylose). An alpha-1,3 branch herein typically comprises or consists of a single (pendant) glucose unit that is alpha-1,3-linked to a backbone.

The percent branching in a glucan herein refers to the percentage of all the glycosidic linkages therein that represent branch points. Percent branching can be with respect to one type of branching. For example, the percent alpha-1,3-branching in a glucan refers to the percentage of all the glycosidic linkages therein that are alpha-1,3 branch points. With respect to one type of branching (e.g., alpha-1,3), there can only be, at most, 50% branching.

A glucosyltransferase (GTF) that is capable of forming at least one alpha-1,3 branch from an acceptor molecule can also be referred to herein as an "alpha-1,3-branching enzyme", "alpha-1,3-branching glucosyltransferase", "alpha-1,3-branching glucansucrase", or other like term. An alpha-1,3-branching enzyme herein is a catalytically active glucosyltransferase (or active fragment thereof) capable of introducing at least one alpha-1,3 glycosidic linkage as a branch to a glucan (glucan backbone) (i.e., glucan is the acceptor in such aspects). In typical aspects, an alpha-1,3-branching enzyme forms an alpha-1,3 branch by transferring the glucose unit from sucrose to a glucan backbone, thereby linking the glucose to the glucan backbone via a glycosidic linkage. Fructose (derived from the sucrose substrate) is a byproduct of this reaction. Besides being able to form alpha-1,3 branches, an alpha-1,3-branching enzyme herein is believed to also be able to link glucose to a non-reducing end of a glucan backbone; however, such a linkage is not considered to be a branch as defined above. An alpha-1,3-branching enzyme herein typically adds one glucose unit per branch (i.e., forms a pendant glucose unit as each branch). Alpha-1,3-branching enzymes herein are classified under glycoside hydrolase family 70 (GH70) and are structurally organized as disclosed in Vuillemin et al. (2016, *J. Biol. Chem.* 14:7687-7702) and Remaud-Simeon et al. (U.S. Patent Appl. Publ. No. 2016/0136199), which are both incorporated herein by reference.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar. Sucrose can alternatively be referred to as "alpha-D-glucopyranosyl-(1→2)-beta-D-fructofuranoside". "Alpha-D-glucopyranosyl" and "glucosyl" are used interchangeably herein.

The terms "acceptor", "acceptor molecule", "acceptor compound" and the like are used interchangeably herein. A suitable acceptor herein is contemplated to be an organic molecule comprising at least one hydroxyl moiety (—OH), which hydroxyl moiety is capable of being involved in formation of a glycosidic linkage (involving the oxygen atom of the hydroxyl moiety) with the 1-position of a glucosyl group (borne from sucrose) via catalytic activity of an alpha-1,3-branching enzyme. A suitable acceptor herein can be a carbohydrate or non-carbohydrate. Examples of carbohydrate acceptors herein include disaccharides, oligosaccharides and polysaccharides; all or some of the monomeric units of a carbohydrate acceptor in some embodiments can be glucose units and/or linked by alpha-glycosidic linkages (e.g., alpha-glucan). When an acceptor herein comprises glucose, the 3-position hydroxyl of a glucose unit of the acceptor is involved in forming a glycosidic linkage with the added branch glucose unit. The term "initial acceptor" can optionally be used herein to characterize an acceptor as used when first preparing an alpha-1,3-branching reaction. An initial acceptor has not yet had any alpha-1,3 branches added to it by the soon-to-be-prepared branching reaction. During the ensuing branching reaction, an acceptor typically serves iteratively as an acceptor for subsequent glucose addition (e.g., typically formation of new pendant glucoses) by the non-native glucosyltransferase.

The linkage profile of a glucan herein can be determined using any method known in the art. For example, a linkage profile can be determined using methods using nuclear magnetic resonance (NMR) spectroscopy (e.g., $^{13}$C NMR or $^1$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, FL, 2005), which is incorporated herein by reference.

The "molecular weight" of large glucan and herein can be represented as weight-average molecular weight (Mw) or number-average molecular weight (Mn), the units of which are in Daltons or grams/mole. Alternatively, such molecular weight can be represented as DPw (weight average degree of polymerization) or DPn (number average degree of polymerization). The molecular weight of smaller polymers such as oligosaccharides typically can be provided as "DP" (degree of polymerization), which simply refers to the number of glucoses comprised within the glucan; "DP" can also characterize the molecular weight of a polymer on an individual molecule basis. Various means for calculating these various molecular weight measurements can be employed such as high-pressure liquid chromatography (HPLC), size exclusion chromatography (SEC), or gel permeation chromatography (GPC).

The terms "enzymatic reaction", "glucosyltransferase reaction", "reaction composition", "reaction formulation", "branching enzyme reaction", "branching reaction" and the like herein generally refer to a reaction that initially comprises water, sucrose, an acceptor molecule (e.g., glucan), at least one non-native glucosyltransferase as presently disclosed, and optionally other components. Components that can be further present in an enzymatic reaction herein include fructose, glucose, leucrose, and soluble gluco-oligosaccharides, one or more of which would typically be present after the reaction has commenced. It is in an enzymatic reaction herein where the step of contacting water, sucrose, acceptor molecule, and a non-native glucosyltransferase enzyme is performed. The term "under suitable reaction conditions" as used herein refers to reaction conditions that support conversion of sucrose and acceptor molecule to products fructose and alpha-1,3-branched acceptor via glucosyltransferase enzyme activity.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. A branching reaction herein is performed under aqueous conditions.

A glucan herein that is "insoluble", "aqueous-insoluble", "water-insoluble" (and like terms) (e.g., alpha-1,3-glucan with a DP of 8 or higher) does not dissolve (or does not appreciably dissolve) in water or other aqueous conditions, optionally where the aqueous conditions are further characterized to have a pH of 4-9 (e.g., pH 6-8) (i.e., non-caustic) and/or a temperature of about 1 to 85° C. (e.g., 20-25° C.). In contrast, glucan herein that is "soluble", "aqueous-soluble", "water-soluble" and the like (e.g., dextran, alpha-1,3-glucan with a DP less than 8) appreciably dissolves under these conditions.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The term "weight/volume percent", "w/v %" and the like are used interchangeably herein. Weight/volume percent can be calculated as: ((mass [g] of material)/(total volume [mL] of the material plus the liquid in which the material is placed))×100%. The material can be insoluble in the liquid (i.e., be a solid phase in a liquid phase, such as with a dispersion), or soluble in the liquid (i.e., be a solute dissolved in the liquid).

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into the host organism by gene transfer. Foreign/heterologous genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

As used herein, the term "polypeptide" is defined as a chain of amino acid residues, usually having a defined sequence. As used herein the term polypeptide is interchangeable with the terms "peptides" and "proteins". Typical amino acids contained in polypeptides herein include (respective three- and one-letter codes shown parenthetically): alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), valine (Val, V).

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". A promoter may alternatively be inducible. One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are well known and exemplified in Sambrook J, Fritsch E F and Maniatis T, *Molecular Cloning: A Laboratory Manual,* 2nd ed., Cold Spring Harbor Laboratory: Cold Spring Harbor, NY (1989), which is incorporated herein by reference, particularly Chapter 11 and Table 11.1.

The term "DNA manipulation technique" refers to any technique in which the sequence of a DNA polynucleotide sequence is modified. Although the DNA polynucleotide sequence being modified can be used as a substrate itself for modification, it does not have to be physically in hand for certain techniques (e.g., a sequence stored in a computer can be used as the basis for the manipulation technique). A DNA manipulation technique can be used to delete and/or mutate one or more DNA sequences in a longer sequence. Examples of a DNA manipulation technique include recombinant DNA techniques (restriction and ligation, molecular cloning), polymerase chain reaction (PCR), and synthetic DNA methods (e.g., oligonucleotide synthesis and ligation). Regarding synthetic DNA techniques, a DNA manipulation technique can entail observing a DNA sequence in silico, determining desired modifications of the DNA sequence, and synthesizing a DNA sequence that contains the desired modifications.

The term "in silico" herein means in or on an information storage and/or processing device such as a computer, and/or done or produced using computer software or simulation, i.e., virtual reality.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting and/or effecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1)

*Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, WI), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.,* 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191(1992); Thompson, J. D. et al, *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with a sequence disclosed herein. A variant amino acid sequence or polynucleotide sequence herein has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "aligns with", "corresponds with", and the like can be used interchangeably herein. Some embodiments herein relate to a non-native glucosyltransferase comprising at least one amino acid substitution at a position corresponding with at least one particular amino acid residue of SEQ ID NO:4. An amino acid position of a non-native glucosyltransferase or subsequence thereof (e.g., catalytic domain) (can refer to such an amino acid position or sequence as a "query" position or sequence) can be characterized to correspond with a particular amino acid residue of SEQ ID NO:4 (can refer to such an amino acid position or sequence as a "subject" position or sequence) if (1) the query sequence can be aligned with the subject sequence (e.g., where an alignment indicates that the query sequence and the subject sequence [or a subsequence of the subject sequence] are at least about 30%, 40%, 50%, 60%, 70%, 80%, or 90% identical), and (2) if the query amino acid position directly aligns with (directly lines up against) the subject amino acid position in the alignment of (1). In general, one can align a query amino acid sequence with a subject sequence (SEQ ID NO:4 or a subsequence of SEQ ID NO:4) using any alignment algorithm, tool and/or software described disclosed herein (e.g., BLASTP, ClustalW, ClustalV, Clustal-Omega, EMBOSS) to determine percent identity. Just for further example, one can align a query sequence with a subject sequence herein using the Needleman-Wunsch algorithm (Needleman and Wunsch, *J. Mol. Biol.* 48:443-453, 1970) as implemented in the Needle program of the European Molecular Biology Open Software Suite (EMBOSS [e.g., version 5.0.0 or later], Rice et al., *Trends Genet.* 16:276-277, 2000). The parameters of such an EMBOSS alignment can comprise, for example: gap open penalty of 10, gap extension penalty of 0.5, EBLOSUM62 (EMBOSS version of BLOSUM62) substitution matrix.

The numbering of particular amino acid residues of SEQ ID NO:4 herein (e.g., Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237) is with respect to the full-length amino acid sequence of SEQ ID NO:4. The first amino acid (i.e., position 1, Met-1) of SEQ ID NO:4 is at the start of the signal peptide. Unless otherwise disclosed, substitutions herein are with respect to the full-length amino acid sequence of SEQ ID NO:4.

A "non-native glucosyltransferase" herein ("mutant", "variant", "modified" and like terms can likewise be used to describe such a glucosyltransferase) has at least one amino acid substitution at a position corresponding with a particular amino acid residue of SEQ ID NO:4. Such at least one amino acid substitution typically is in place of the amino acid residue(s) that normally (natively) occurs at the same position in the native counterpart (parent) of the non-native glucosyltransferase (i.e., although SEQ ID NO:4 is used as a reference for position, an amino acid substitution herein is with respect to the native counterpart of a non-native glucosyltransferase) (considered another way, when aligning the sequence of a non-native glucosyltransferase with SEQ ID NO:4, determining whether a substitution exists at a particular position does not depend in-and-of-itself on the respective amino acid residue in SEQ ID NO:4, but rather depends on what amino acid exists at the subject position within the native counterpart of the non-native glucosyltransferase). The amino acid normally occurring at the relevant site in the native counterpart glucosyltransferase often (but not always) is the same as (or conserved with) the particular amino acid residue of SEQ ID NO:4 for which the alignment is made. A non-native glucosyltransferase optionally can have other amino acid changes (mutations, deletions, and/or insertions) relative to its native counterpart sequence.

It may be instructive to illustrate a substitution/alignment herein. SEQ ID NO:15 (GTF BRS-B) is a full-length, mature *Leuconostoc citreum* alpha-1,3-branching enzyme. It is noted that Ser-628 of SEQ ID NO:15 corresponds with Ser-734 of SEQ ID NO:4 (alignment not shown). If SEQ ID NO:15 is mutated at position 628 to substitute the Ser residue with a different residue (e.g., Gly), then it can be stated that the position 628-mutated version of SEQ ID NO:15 represents a non-native glucosyltransferase having an amino acid substitution at a position corresponding with Ser-734 of SEQ ID NO:4, for example.

The term "motif" herein refers to a distinctive and recurring structural unit, such as within an amino acid sequence. By "recurring" it is meant that a motif occurs in multiple related polypeptides, for example.

The term "isolated" means a substance (or process) in a form or environment that does not occur in nature. Non-limiting examples of isolated substances include (1) any non-naturally occurring substance (e.g., a non-native glucosyltransferase herein), (2) any substance including, but not limited to, any host cell, enzyme, variant, nucleic acid, protein, peptide, cofactor, or carbohydrate/saccharide that is at least partially removed from one or more or all of the naturally occurring constituents with which it is associated in nature; (3) any substance modified by the hand of man relative to that substance found in nature (e.g., a non-native glucosyltransferase herein); or (4) any substance modified by increasing the amount of the substance relative to other components with which it is naturally associated. It is believed that the embodiments (e.g., enzymes and reaction compositions) disclosed herein are synthetic/man-made (could not have been made except for human intervention/ involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

While advances have been made in understanding and using alpha-1,3-branching enzymes, less attention appears to have been drawn to modulating the activity of these enzymes. Such modulated enzymes could prove to be a valuable tool for providing glucan products with defined structure for specific applications. Addressing this technological gap, disclosed herein are alpha-1,3-branching enzymes with modified amino acid sequences that have altered alpha-1,3-branching activity.

Certain embodiments of the present disclosure concern a non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, wherein the non-native glucosyltransferase is capable of forming at least one alpha-1,3 branch from an acceptor molecule. Such a non-native glucosyltransferase typically has modified alpha-1,3 branching activity (increased or decreased) as compared to a second glucosyltransferase that only differs from the non-native glucosyltransferase at the substitution position(s). This modified activity can be taken advantage of, for example, to better control alpha-1,3 branching of a glucan acceptor.

A non-native glucosyltransferase of the present disclosure can, for example, (i) comprise at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, and (ii) comprise, or consist of, an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:2 (or residues 477-1322 of SEQ ID NO:2), 3, 4, 13, 14 (i.e., residues 446-1313 of SEQ ID NO:13), or 15. In some aspects, a non-native glucosyltransferase (i) comprises at least one of the foregoing amino acid substitutions, and (ii) comprises, or consists of, an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to a polypeptide sequence as disclosed in Vuillemin et al. (2016, *J. Biol. Chem.* 14:7687-7702) or Remaud-Simeon et al. (U.S. Patent Appl. Publ. No. 2016/0136199) (both references incorporated herein by reference) to have alpha-1,3-branching activity.

Although amino acid substitutions in a non-native glucosyltransferase are generally disclosed herein with respect to the corresponding positions in SEQ ID NO:4, such substitutions can alternatively be stated simply with respect to its position number in the sequence of the non-native glucosyltransferase itself, as convenience may dictate.

Still further examples of non-native glucosyltransferases can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A non-native glucosyltransferase herein typically lacks an N-terminal signal peptide; such an enzyme can optionally be characterized as being mature if its signal peptide was removed during a secretion process.

A non-native glucosyltransferase herein can be derived/ derivable from any suitable microbial source, for example, such as bacteria. Examples of bacterial glucosyltransferases with alpha-1,3-branching activity can be derived/derivable from a *Leuconostoc* species such as *L. fallax* and *L. citreum*. In some aspects, a non-native glucosyltransferase can comprise an amino acid sequence as disclosed in GenBank Acc. No. WP_010006776.1, TDG68566.1, WP_080984265.1, WP_040190490.1, WP_040177263.1, OSP81041.1, or TDM37010.1, but with the exception that the non-native glucosyltransferase comprises at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4. In some aspects, such a non-native glucosyltransferase (i) has at least one of the foregoing substitutions, and (ii) comprises an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of the respective counterpart/ parent glucosyltransferase not having the at least one sub-stitution.

A non-native glucosyltransferase in some aspects only differs from a second glucosyltransferase (or, simply, "another" glucosyltransferase) (e.g., parent glucosyltrans-ferase) at its substitution position(s), wherein the second glucosyltransferase is an alpha-1,3-branching enzyme that comprises the motifs of: (i) an amino acid sequence that is at least 80% identical to SEQ ID NO:9 or 5, (ii) an amino acid sequence that is at least 80% identical to SEQ ID NO:10 or 6, (iii) an amino acid sequence that is at least 80% identical to SEQ ID NO:11 or 7, and (iv) an amino acid sequence that is at least 80% identical to SEQ ID NO:12 or 8. A second glucosyltransferase in some aspects comprises each of these motifs that, respectively, are at least 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NOs:9-12 (or 5-8). In some of these aspects, motif (ii) can comprise an Asp residue at position 5 thereof, motif (iii) can comprise a Glu residue at position 6 thereof, and motif (iv) can comprise an Asp residue at position 6 thereof, for example. The order of the motifs as they exist in a second glucosyltransferase typically is (ii)-(iii)-(iv)-(i). A second glucosyltransferase herein, for example, can be com-prised of all of, or mostly, native amino acid sequence. Thus, while a second glucosyltransferase herein can be a native glucosyltransferase in some aspects, it can be a prior-modified (or otherwise variant) glucosyltransferase in other aspects (e.g., a glucosyltransferase with one or more other amino acid substitutions differing from the substitution[s] of the present disclosure). In some embodiments, a second glucosyltransferase to which a non-native glucosyltransfer-ase is compared has a native amino acid residue(s) at the substitution position(s). Determining whether an amino acid residue is native can be done by comparing the second glucosyltransferase amino acid sequence to the native/wild type glucosyltransferase amino acid sequence from which the second glucosyltransferase is derived/derivable. A non-native glucosyltransferase herein is typically derived/deriv-able from a second glucosyltransferase as disclosed above.

A non-native glucosyltransferase in some aspects com-prises motifs with amino acid sequences that are less than 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identical to SEQ ID NOs:9-12 (or 5-8) (the stated percent identity is with respect to each sequence considered individually), but that are more than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, or 93% identical to SEQ ID NOs: 9-12 (or 5-8) (the stated percent identity is with respect to each sequence considered individually). It is noted that the disclosed amino acid substitutions occur in the conserved motifs of SEQ ID NOs:9-12 (or 5-8). The order of motifs in a non-native glucosyltransferase typically are as they occur in a second glucosyltransferase (above).

A non-native glucosyltransferase herein can be prepared by fermentation of an appropriately engineered microbial strain, for example. Recombinant enzyme production by fermentation is well known in the art using microbial species such as E. coli, Bacillus strains (e.g., B. subtilis), Ralstonia eutropha, Pseudomonas fluorescens, Saccharomyces cerevi-siae, Pichia pastoris, Hansenula polymorpha, and species of Aspergillus (e.g., A. awamori) and Trichoderma (e.g., T.

reesei) (e.g., see Adrio and Demain, Biomolecules 4:117-139, 2014, which is incorporated herein by reference). A nucleotide sequence encoding a non-native glucosyltrans-ferase amino acid sequence is typically linked to a heter-ologous promoter sequence to create an expression cassette for the enzyme, and/or is codon-optimized accordingly. Such an expression cassette may be incorporated in a suitable plasmid or integrated into the microbial host chro-mosome, using methods well known in the art. The expres-sion cassette may include a transcriptional terminator nucleotide sequence following the amino acid coding sequence. The expression cassette may also include, between the promoter sequence and glucosyltransferase amino acid coding sequence, a nucleotide sequence encod-ing a signal peptide (e.g., heterologous signal peptide) that is designed for direct secretion of the glucosyltransferase enzyme. At the end of fermentation, cells may be ruptured accordingly (generally when a signal peptide for secretion is not employed) and the glucosyltransferase enzyme can be isolated using methods such as precipitation, filtration, and/ or concentration. Alternatively, a lysate or extract compris-ing a glucosyltransferase can be used without further isola-tion. If the glucosyltransferase was secreted (i.e., it is present in the fermentation broth), it can optionally be used as isolated from, or as comprised in, the fermentation broth.

A non-native glucosyltransferase herein can comprise at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4. In some aspects, the amino acid substitution at the position corresponding with amino acid residue Ser-734 is with a Cys, Asp, Gly, His, Lys, Leu, Met, Asn, Thr, or Val residue. In some aspects, the amino acid substitution at the position corresponding with amino acid residue Ile-735 is with an Ala, Leu, or Val residue. In some aspects, the amino acid substitution at the position corresponding with amino acid residue Ile-737 is with an Ala, Cys, Asp, Gly, His, Leu, Met, Asn, Ser, Val, Trp, or Tyr residue. In some aspects, the amino acid substitution at the position corresponding with amino acid residue Ile-740 is with an Ala, Leu, or Val residue. In some aspects, the amino acid substitution at the position corresponding with amino acid residue Asp-744 is with an Ala, Cys, Glu, Phe, Gly, His, Lys, Met, Asn, Pro, Gln, Arg, Ser, Thr, Val, Trp, or Tyr residue. In some aspects, the amino acid substitution at the position corresponding with amino acid residue His-771 is with an Ala residue. In some aspects, the amino acid substitution at the position corresponding with amino acid residue Val-772 is with an Ala or Leu residue. In some aspects, the amino acid substi-tution at the position corresponding with amino acid residue Ser-773 is with an Ala or Asn residue. In some aspects, the amino acid substitution at the position corresponding with amino acid residue Val-775 is with an Ala residue. In some aspects, the amino acid substitution at the position corre-sponding with amino acid residue Ser-778 is with a Trp residue. In some aspects, the amino acid substitution at the position corresponding with amino acid residue Ala-779 is with an Asp, Gly, or Ser residue. In some aspects, the amino acid substitution at the position corresponding with amino acid residue Asp-780 is with an Ala, Gln, or Tyr residue. In some aspects, the amino acid substitution at the position corresponding with amino acid residue Ile-845 is with an Ala or Phe residue. In some aspects, the amino acid substi-tution at the position corresponding with amino acid residue Val-846 is with an Ala, Ile, or Thr residue. In some aspects, the amino acid substitution at the position corresponding with amino acid residue Asp-852 is with an Ala, Glu, Leu, or Asn residue. In some aspects, the amino acid substitution at the position corresponding with amino acid residue Ile-853 is with a Val residue. In some aspects, the amino acid substitution at the position corresponding with amino acid residue Asp-855 is with an Ala, Gly, or Ser residue. In some aspects, the amino acid substitution at the position corresponding with amino acid residue Ser-858 is with an Ala, Gly, Gln, or Arg residue. In some aspects, the amino acid substitution at the position corresponding with amino acid residue Asn-859 is with an Ala, Asp, Glu, Lys, Ser, or Thr residue. In some aspects, the amino acid substitution at the position corresponding with amino acid residue Ala-1232 is with a Cys, Asp, Glu, Phe, Gly, His, Leu, Met, Asn, Pro, Gln, Ser, Thr, Val, or Tyr residue. In some aspects, the amino acid substitution at the position corresponding with amino acid residue Tyr-1234 is with a Cys, Glu, His, Leu, Met, Thr, Val, or Trp residue. In some aspects, the amino acid substitution at the position corresponding with amino acid residue Asn-1237 is with an Asp or Gly residue.

A non-native glucosyltransferase only comprises one of the foregoing amino acid substitution in some embodiments. In some instances, a non-native glucosyltransferase does not comprise an amino acid substitution with (i) an Ile, Arg, Trp, Pro, or Tyr residue at the position corresponding with amino acid residue Ser-734 of SEQ ID NO:4, (ii) a Glu or Thr residue at the position corresponding with amino acid residue Ile-737 of SEQ ID NO:4, (iii) an Arg residue at the position corresponding with amino acid residue His-847 of SEQ ID NO:4, (iv) a Lys residue at the position corresponding with amino acid residue Ala-1232 of SEQ ID NO:4, and/or (v) a Phe, Ile, or Leu residue at the position corresponding with amino acid residue Asn-1237 of SEQ ID NO:4.

Suitable substitution sites, and examples of particular substitutions at these sites, can include those as listed in Table 3 in Example 1 (below). For example, suitable substitution sites, and examples of particular substitutions at these sites, can be any of those in Table 3 that are associated with an increase of about, or at least about, 10%, 25%, 50%, 75%, 100%, 150%, 200%, 250%, 300%, 325%, 10%-325%, 25%-325%, 50%-325%, 100%-325%, 10%-200%, 25%-200%, 50%-200%, or 100%-200% in alpha-1,3-branching activity. As another example, suitable substitution sites, and examples of particular substitutions at these sites, can be any of those in Table 3 that are associated with a decrease of about, or at least about, 10%, 25%, 50%, 75%, 10%-75%, 25%-75%, or 50%-75% in alpha-1,3-branching activity. The foregoing substitutions as listed in Table 3 are as they correspond with the listed residue position number in SEQ ID NO:4; the foregoing percent changes are with respect to the activity of SEQ ID NO:2.

In some aspects, a non-native glucosyltransferase comprises two, three, four, five, six, seven, eight, nine, ten, eleven, twelve or more amino acid substitutions, wherein at least one of the substitutions is at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4. Examples of particular substitutions at these sites are as listed above. In any of these or other aspects, at least one of the substitutions is at a position corresponding with amino acid residue Ser-734, Ile-735, Ser-778, Asp-780, Ile-845, Asp-852, Ile-853, Asp-855, Ala-1232, or Tyr-1234 of SEQ ID NO:4, optionally wherein the amino acid substitution at the position corresponding with amino acid residue Ser-734 is with a Cys residue, the amino acid substitution at the position corresponding with amino acid residue Ile-735 is with a Val residue, the amino acid substitution at the position corresponding with amino acid residue Ser-778 is with a Trp residue, the amino acid substitution at the position corresponding with amino acid residue Asp-780 is with a Tyr residue, the amino acid substitution at the position corresponding with amino acid residue Ile-845 is with a Phe residue, the amino acid substitution at the position corresponding with amino acid residue Asp-852 is with a Glu residue, the amino acid substitution at the position corresponding with amino acid residue Ile-853 is with a Val residue, the amino acid substitution at the position corresponding with amino acid residue Asp-855 is with a Gly residue, the amino acid substitution at the position corresponding with amino acid residue Ala-1232 is with a Gly, Met, Ser, or Val residue, and/or the amino acid substitution at the position corresponding with amino acid residue Tyr-1234 is with a Trp residue.

A non-native glucosyltransferase herein can comprise one, two, three, four, five, six, seven, eight, nine, ten, eleven, twelve, or more of the presently disclosed amino acid substitutions, for instance. For example, a non-native glucosyltransferase can comprise substitutions at positions corresponding with:

(i) amino acid residue Ser-734, Ile-735, Ile-740, and/or Asp-744 of SEQ ID NO:4;

(ii) amino acid residue Val-775, Ser-778, and/or Asp-780 of SEQ ID NO:4;

(iii) amino acid residue Ile-845, Asp-852, Ile-853, Asp-855 of SEQ ID NO:4; and/or (iv) amino acid residue Ala-1232 and/or Tyr-1234 of SEQ ID NO:4.

In some aspects, the amino acid substitution positions can be (i), (ii), (iii), (iv), (i)+(ii), (i)+(iii), (i)+(iv), (ii)+(iii), (ii)+(iv), (iii)+(iv), (i)+(ii)+(iii), (i)+(ii)+(iv), (i)+(iii)+(iv), (ii)+(iii)+(iv), or (i)+(ii)+(iii)+(iv). Examples of substitutions in any of these combinations include S734(C), I735(L or V), I740(A or L), D744(T or N), V775(A), S778(W), D780(Y), I845(F), D852(E), I853(V), D855(G), A1232(G, M, S, or V), Y1234AO, and Y1237(G), where substituting amino acid residues are listed parenthetically as examples.

Simply for illustration purposes, a non-native glucosyltransferase herein can comprise a combination of amino acid substitutions at positions as shown in Table A (i-xxvii), where each substitution position corresponds with the respective amino acid position number in SEQ ID NO:4. The substituting amino acid residues in Table A are listed parenthetically as examples. In some aspects, a non-native glucosyltransferase can comprise a combination of amino acid substitutions as shown in Table A, where the substituting amino acids are those shown parenthetically in Table A.

TABLE A

| Examples of Amino Acid Substitution Combinations |
| --- |
| Substitution[a] Combinations |

| | |
| --- | --- |
| i | I735(L)/D780(Y)/I845(F)/D852(E)/I853(V)/D855(G)/A1232(G)/Y1234(W) |
| ii | I735(L)/D780(Y)/I845(F)/D852(E)/I853(V)/D855(G)/A1232(M)/Y1234(W) |
| iii | I735(V)/D780(Y)/I845(F)/D852(E)/I853(V)/D855(G)/A1232(S)/Y1234(W) |
| iv | I735(V)/D780(Y)/I845(F)/D852(E)/I853(V)/D855(G)/A1232(G)/Y1234(W) |
| v | I735(V)/D780(Y)/I845(F)/D852(E)/I853(V)/D855(G)/A1232(M)/Y1234(W) |
| vi | I735(V)/D780(Y)/I845(F)/D852(E)/I853(V)/D855(G)/A1232(V)/Y1234(W) |
| vii | S734(C)/D780(Y)/I845(F)/D852(E)/I853(V)/D855(G)/A1232(V)/N1237(G) |
| viii | S734(C)/S778(W)/I845(F)/D852(E)/I853(V)/D855(G)/A1232(V)/Y1234(W) |
| ix | S734(C)/S778(W)/I845(F)/D852(E)/I853(V)/D855(G)/A1232(G)/Y1234(W) |
| x | 5734(C)/S778(W)/I845(F)/D852(E)/I853(V)/D855(G)/A1232(G)/Y1234(W) |
| xi | 5734(C)/S778(W)/I845(F)/D852(E)/I853(V)/D855(G)/A1232(M)/Y1234(W) |
| xii | 5734(C)/S778(W)/I845(F)/D852(E)/I853(V)/D855(G)/A1232(S)/Y1234(W) |
| xiii | I735(V)/V775(A)/D780(Y)/I845(F)/D852(E)/I853(V)/D855(G)/A1232(V)/Y1234(W) |
| xiv | I735(V)/S778(W)/D780(Y)/I845(F)/D852(E)/I853(V)/D855(G)/A1232(V)/Y1234(W) |
| xv | I735(V)/S778(W)/D780(Y)/I845(F)/D852(E)/I853(V)/D855(G)/A1232(V)/Y1234(W) |
| xvi | S734(C)/V775(A)/S778(W)/D780(Y)/I845(F)/D852(E)/I853(V)/D855(G)/A1232(V)/Y1234(W) |
| xvii | S734(C)/I735(V)/V775(A)/S778(W)/I845(F)/D852(E)/I853(V)/D855(G)/A1232(G)/Y1234(W) |
| xviii | S734(C)/I735(V)/V775(A)/S778(W)/I845(F)/D852(E)/I853(V)/D855(G)/A1232(V)/Y1234(W) |
| xix | S734(C)/I735(V)/V775(A)/S778(W)/D780(Y)/I845(F)/D852(E)/I853(V)/D855(G)/A1232(V)/Y1234(W) |
| xx | S734(C)/I735(V)/V775(A)/S778(W)/D780(Y)/I845(F)/D852(E)/I853(V)/D855(G)/A1232(G)/Y1234(W) |
| xxi | S734(C)/I735(L)/I740(A)/S778(W)/D780(Y)/I845(F)/D852(E)/I853(V)/D855(G)/A1232(G)/Y1234(W) |
| xxii | 5734(C)/I735(V)/I740(A)/S778(W)/D780(Y)/I845(F)/D852(E)/I853(V)/D855(G)/A1232(G)/Y1234(W) |
| xxiii | 5734(C)/I735(V)/D744(T)/S778(W)/D780(Y)/I845(F)/D852(E)/I853(V)/D855(G)/A1232(V)/Y1234(W) |
| xxiv | 5734(C)/I735(V)/D744(T)/V775(A)/S778(W)/D780(Y)/I845(F)/D852(E)/I853(V)/D855(G)/A1232(G)/Y1234(W) |
| xxv | 5734(C)/I735(V)/D744(N)/V775(A)/S778(W)/D780(Y)/I845(F)/D852(E)/I853(V)/D855(G)/A1232(G)/Y1234(W) |
| xxvi | 5734(C)/I735(V)/I740(L)/V775(A)/S778(W)/D780(Y)/I845(F)/D852(E)/I853(V)/D855(G)/A1232(G)/Y1234(W) |
| xxvii | 5734(C)/I735(V)/I740(A)/V775(A)/S778(W)/D780(Y)/I845(F)/D852(E)/I853(V)/D855(G)/A1232(G)/Y1234(W) |

[a]Amino acid residues listed parenthetically are examples of substituting amino acid residues.

A non-native glucosyltransferase with one or more amino acid substitutions herein can be based on any of a variety of glucosyltransferase amino acid sequences as presently disclosed, for example. Simply for illustration purposes, examples of such a non-native glucosyltransferase include those with at least one amino acid substitution (e.g., at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4) or a combination of amino acid substitutions (e.g., any of embodiments i-xxvii of Table A) and that comprise or consist of an amino acid sequence that is at least about 90%, 91%, 92%, 93%, 94%, 95%, 96%, 97%, 98%, 99%, or 99.5% identical to: SEQ ID NO:2 (optionally without the start methionine and/or 6xHis tag of SEQ ID NO:2), SEQ ID NO:3, residues 477-1322 of SEQ ID NO:2, SEQ ID NO:15, or residues 446-1313 of SEQ ID NO:13.

In some aspects, one or more substitutions are conserved or non-conserved substitutions; such conservation (or not) can be, for instance, with respect to the amino acid that occurs in the native glucosyltransferase from which the non-native glucosyltransferase is derived.

A non-native glucosyltransferase as presently disclosed is capable of forming at least one alpha-1,3 branch from a suitable acceptor molecule. An acceptor herein typically is aqueous-soluble, or at least a portion (more than 10, 20, 30, 40, 50, 60, 70, 80, 90, or 95 wt %) thereof is soluble. In some aspects, an acceptor comprises or consists of glucan (e.g., oligosaccharide and/or polysaccharide forms of glucan) such as alpha-glucan (e.g., dextran).

In some aspects, an acceptor molecule comprises a monosaccharide, disaccharide, or oligosaccharide. Yet in some aspects, an acceptor consists of a monosaccharide, disaccharide, or oligosaccharide (e.g., the saccharide acceptor is not chemically derivatized/substituted). A disaccharide or oligosaccharide acceptor molecule typically comprises one or more glucose monomeric units (e.g., at least about 10%, 20%, 30%, 40%, 50%, 60%, 70%, 80%, 90%, or 95% of the monomeric units are glucose), or comprises only glucose monomeric units. A disaccharide or oligosaccharide can optionally comprise, typically in addition to one or more glucose monomeric units, one or more non-glucose monomeric units. A non-glucose monomeric unit of a disaccharide or oligosaccharide (or a non-glucose monosaccharide acceptor) can be fructose, arabinose, xylose, or galactose in some aspects. In some aspects, an acceptor is not (does not consist of) glucose, fructose, mannose, or glucosamine. An acceptor can be linear (no branches) or branched, for example.

A disaccharide or oligosaccharide acceptor molecule herein can comprise alpha-glycosidic linkages and/or beta-glycosidic linkages. The linkages of an acceptor can be 100% alpha-glycosidic linkages, or at least about 50%, 60%, 70%, 80%, 90%, or 95% alpha-glycosidic linkages, for example. Alpha- or beta-glycosidic linkages between glucose monomers of a disaccharide or oligosaccharide acceptor can comprise one type of, or more than one type of, the following linkages: 1,1; 1,2; 1,3; 1,4; and/or 1,6. Just to illustrate, the linkages can be all alpha-1,6 glucosidic linkages or all alpha-1,4 glucosidic linkages, or a mix of alpha-1,6 and alpha-1,6 glucosidic linkages. Also to illustrate, the linkages can be at least 50%, 60%, 70%, 80%, 90%, 91%, 92%, 93%, 94%, 95%, 96%, 97%, 98%, or 99% alpha-1,6 glycosidic linkages, where the balance of the linkages can be alpha-1,3, alpha-1,4, alpha-1,2, or a mix thereof; these types of oligosaccharide can optionally be characterized as forms of dextran. A disaccharide or oligosaccharide acceptor herein typically is aqueous-soluble.

An oligosaccharide acceptor herein can have, have at least, or have up to, 3, 4, 5, 6, 7, 8, 9, 10, 11, 12, 13, 14, or 15 monomeric units, for example. Particular examples of such an oligosaccharide acceptor molecule can comprise only glucose monomeric units and/or which are linked by alpha-1,6 linkages.

In some aspects, an acceptor molecule comprises a polysaccharide. Yet in some aspects, an acceptor consists of a polysaccharide (e.g., the polysaccharide acceptor is not chemically derivatized/substituted). A polysaccharide acceptor molecule typically comprises one or more glucose monomeric units (e.g., at least about 10%, 20%, 30%, 40%, 50%, 60%, 70%, 80%, 90%, or 95% of the monomeric units are glucose), or comprises only glucose monomeric units (i.e., a form of glucan). A polysaccharide can optionally comprise, typically in addition to one or more glucose monomeric units, one or more non-glucose monomeric units. A non-glucose monomeric unit of a polysaccharide can be fructose, arabinose, xylose, or galactose in some aspects.

A polysaccharide acceptor molecule herein can comprise alpha-glycosidic linkages and/or beta-glycosidic linkages. The linkages of a polysaccharide acceptor can be 100% alpha-glycosidic linkages (e.g., alpha-glucan), or at least about 50%, 60%, 70%, 80%, 90%, or 95% alpha-glycosidic linkages, for example. Alpha- or beta-glycosidic linkages between glucose monomers of a polysaccharide acceptor can comprise one type of, or more than one type of, the following linkages: 1,1; 1,2; 1,3; 1,4; and/or 1,6. Just to illustrate, the linkages can be all alpha-1,6 glucosidic linkages, all alpha-1,4 glucosidic linkages, or a mix of alpha-1,6 and alpha-1,4 glucosidic linkages. Also to illustrate, the linkages can be at least 50%, 60%, 70%, 80%, 90%, 91%, 92%, 93%, 94%, 95%, 96%, 97%, 98%, or 99% alpha-1,6 glycosidic linkages, where the balance of the linkages can be alpha-1,3, alpha-1,4, alpha-1,2, or a mix thereof; these types of polysaccharide can optionally be characterized as forms of dextran. A polysaccharide acceptor herein typically is aqueous-soluble.

A polysaccharide acceptor herein can have a DP or DPw of about, or at least about, 16, 17, 18, 19, 20, 21, 22, 23, 24, 25, 26, 27, 28, 29, 30, 35, 40, 45, 50, 75, 100, 150, 200, 225, 250, 275, 300, 350, 400, 450, 500, 550, 575, 600, 625, 650, or 700, for example. This DP/DPw can optionally be expressed as a range between any two of these values (e.g., 200-300, 225-275, 550-650, 575-625).

An acceptor in some aspects is dextran. Dextran can comprise, for example, about 100% alpha-1,6-glycosidic linkages (i.e., completely linear dextran backbone), or about, or at least about, 95%, 96%, 97%, 98%, 99%, or 99.5% alpha-1,6-glycosidic linkages (i.e., substantially linear dextran backbone), for example. Such a percent alpha-1,6 linkage profile is that taking account of the total of all linkages in the dextran (combination of main chain and, if present, branch portions). In some aspects, a substantially linear dextran acceptor can comprise 5%, 4%, 3%, 2%, 1%, 0.5% or less branches. If present, dextran branches typically are short, being one (pendant) to three glucose monomers in length, and comprise less than about 10%, 9%, 8%, 7%, 6%, 5%, 4%, 3%, 2%, or 1% of all the glucose monomers of the dextran acceptor. All the foregoing dextran linkage information pertains to a dextran acceptor prior to its modification with alpha-1,3 branches.

In some aspects, a dextran acceptor can have a DP or DPw of about, or at least about, or no more than about, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 85, 90, 95, 100, 105, 110, 150, 200, 225, 250, 275, 300, 350, 400, 450, 500, 550, 575, 600, 625, 650, or 700. This DP or DPw can optionally be expressed as a range between any two of these values. Merely as examples, the DP or DPw can be about 8-20, 8-30, 8-100, or 8-500, 3-4, 3-5, 3-6, 3-7, 3-8, 4-5, 4-6, 4-7, 4-8, 5-6, 5-7, 5-8, 6-7, 6-8, or 7-8. Merely as other examples, this DP or DPw can be 90-120, 95-120, 100-120, 105-120, 110-120, 115-120, 90-115, 95-115, 100-115, 105-115, 110-115, 90-110, 95-110, 100-110, 105-110, 90-105, 95-105, 100-105, 90-100, 95-100, 90-95, 85-95, 85-90, 200-300, 225-275, 550-650, or 575-625. As yet more examples, a dextran acceptor can have an Mw of about, or at least about, or no more than about, 0.1, 0.125, 0.15, 0.175, 0.2, 0.24, 0.25, 0.5, 0.75, 0.1, 0.1-0.2, 0.125-0.175, 0.13-0.17, 0.135-0.165, 0.14-0.16, 1, 2, 3, 4, 5, 6, 7, 8, 9, 10, 20, 30, 40, 50, 60, 70, 80, 90, 100, 110, 120, 130, 140, 150, 160, 170, 180, 190, 200, 10-80, 20-70, 30-60, 40-50, 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 90-110, 100-120, 110-120, 50-110, 60-110, 70-110, 80-110, 90-110, 100-110, 50-100, 60-100, 70-100, 80-100, 90-100, or 95-105 million Daltons. Yet, in some aspects, a dextran acceptor can be any as disclosed in U.S. Patent Appl. Publ. Nos. 2016/0122445, 2018/0282385, or 2020/0165360, or International Patent Appl. Publ. No. WO2017/079595, for example, which are all incorporated herein by reference.

Dextran for use as an acceptor herein can be produced enzymatically, for example. In certain embodiments, dextran can be synthesized using a dextransucrase and/or methodology as disclosed in U.S. Patent Appl. Publ. Nos. 2018/0282385 or 2017/0218093, which are incorporated herein by reference. The dextransucrase identified as GTF8117, GTF6831, or GTF5604 in these references can be used, if desired (or any dextransucrase comprising an amino acid sequence that is at least about 90%, 91%, 92%, 93%, 94%, 95%, 96%, 97%, 98%, or 99% identical to any of these particular dextransucrases). Such enzymatically produced dextran is typically linear (i.e., 100% alpha-1,6 linkages) and aqueous soluble.

Some embodiments disclosed herein concern a polynucleotide comprising a nucleotide sequence that encodes a non-native glucosyltransferase as presently disclosed (e.g., a non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4). Optionally, one or more regulatory sequences are operably linked to the nucleotide sequence, and preferably a promoter sequence is included as a regulatory sequence.

A polynucleotide comprising a nucleotide sequence encoding a non-native glucosyltransferase herein can be a vector or construct useful for transferring a nucleotide sequence into a cell, for example. Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding a non-native glucosyltransferase. For example, a nucleotide sequence encoding a non-native glucosyltransferase may be in operable linkage with a promoter sequence (e.g., a heterologous promoter). A promoter sequence can be suitable for expression in a cell (e.g., bacterial cell such as *E. coli* or *Bacillus*; eukaryotic cell such as a fungus, yeast, insect, or mammalian cell) or in an in vitro protein expression system, for example. Examples of other suitable regulatory sequences include transcription terminator sequences.

Some aspects herein are drawn to a cell comprising a polynucleotide sequence as presently disclosed; such a cell can be any type disclosed herein (e.g., bacterial cell such as *E. coli* or *Bacillus*; eukaryotic cell such as a fungus, yeast, insect, or mammalian cell). A cell can optionally express a non-native glucosyltransferase encoded by the polynucleotide sequence. In some aspects, the polynucleotide sequence exists transiently (i.e., not integrated into the genome) or stably (i.e., integrated into the genome) in the cell.

Some embodiments disclosed herein concern a reaction composition comprising water, sucrose, a suitable acceptor molecule, and one or more non-native glucosyltransferases herein (e.g., a non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4). Such a reaction composition can produce, at least, a glucan composition that comprises at least one alpha-1,3 branch.

The temperature of a reaction composition herein can be controlled, if desired, and can be about 5-50° C., 20-40° C., 30-40° C., 20-30° C., 20-25° C., 20° C., 25° C., 30° C., 35° C., or 40° C., for example.

The initial concentration of sucrose in a reaction composition herein can be about, or at least about, 1, 3, 5, 25, 50, 75, 100, 150, 200, 25-200, 25-150, 25-100, or 25-75 g/L, for example. "Initial concentration of sucrose" refers to the sucrose concentration in a reaction composition just after all the reaction components have been added/combined (e.g., at least water, sucrose, acceptor, non-native glucosyltransferase enzyme).

The pH of a reaction composition in certain embodiments can be about 4.0-9.0, 4.0-8.5, 4.0-8.0, 5.0-8.0, 5.0-7.5, 5.0-6.5, or 5.0-6.0. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, acetate, or a combination thereof. The buffer concentration in a reaction composition herein can be about 0.1-300 mM, 01.-150 mM, 0.1-100 mM, 10-150 mM, 10-100 mM, 10 mM, 20 mM, 50 mM, 75 mM, or 100 mM, for example.

The initial concentration of an acceptor in a reaction herein can be about 25, 50, 75, 100, 150, 200, 25-200, 25-150, 25-100, or 25-75 g/L, for example. In some aspects, the initial concentration of an acceptor can be about, or at least about, 1, 2, 5, 10, 15, 1-10, or 1-5 mM. "Initial concentration" of a substrate such as an acceptor refers to the substrate concentration in an enzymatic reaction just after all the reaction components have been added (e.g., at least water, sucrose, acceptor, non-native glucosyltransferase enzyme). An acceptor can be any as disclosed herein.

A reaction composition can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein), can be about, or at least about, 1, 10, 50, 100, 500, 1000, 2500, 5000, 10000, 12500, 15000, or 20000 liters. An inert vessel can optionally be equipped with a stirring device. Any of the foregoing features, for example, can be used to characterize an isolated reaction herein.

A reaction composition herein can contain one, two, or more different glucosyltransferase enzymes, for example, just as long that at least one of the enzymes is a non-native glucosyltransferase as presently disclosed. In some embodiments, only one or two glucosyltransferase enzymes is/are comprised in a reaction composition. A glucosyltransferase reaction herein can be, and typically is, cell-free (e.g., no whole cells present). In some aspects, a reaction composition can comprise about, or at least about, 0.5, 1.0, 1.5, 2.0, 2.5, 0.5-2.5, 0.5-2.0, or 0.5-1.5 units/mL. A unit of alpha-1,3-branching glucosyltransferase activity can optionally be set as the amount of glucosyltransferase that produces 1 μmol of fructose/minute at 30° C. in 50 mM sodium acetate buffer at pH 5.75 from 100 g/L sucrose.

Any of the features disclosed herein (e.g., above and in the below Examples) regarding a reaction composition can characterize appropriate aspects of an alpha-1,3-branched glucan production method herein, and vice versa.

The present disclosure also concerns a method for producing a glucan composition that comprises at least one alpha-1,3 branch, the method comprising: (a) contacting at least water, sucrose, a glucan substrate (glucan acceptor), and one or more non-native glucosyltransferases herein (e.g., a non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4), whereby a glucan composition comprising at least one alpha-1,3 branch is produced; and (b) optionally isolating the glucan composition produced in step (a). Conducting such a method, which can optionally be characterized as an alpha-1,3-branched glucan synthesis method, is typically also performed when conducting a reaction composition herein.

An alpha-1,3-branched glucan synthesis method as presently disclosed comprises contacting at least water, sucrose, a glucan substrate (glucan acceptor), and one or more non-native glucosyltransferases herein. These and optionally other reagents can be added altogether or in any order as discussed below. This step can optionally be characterized as providing a reaction composition comprising at least water, sucrose, a glucan substrate (glucan acceptor), and one or more non-native glucosyltransferases herein. The contacting step herein can be performed in any number of ways. For example, the desired amount of sucrose can first be dissolved in water (optionally, other components may also be added at this stage of preparation, such as buffer components), followed by addition of glucosyltransferase enzyme. The solution may be kept still, or agitated via stirring or orbital shaking, for example. A glucan synthesis method can be performed by batch, fed-batch, continuous mode, or by any variation of these modes.

A reaction of the disclosed process can be conducted for about 1 hour to about, or at least about, 2, 4, 6, 8, 10, 12, 14, 16, 18, 20, 22, 24, 36, 48, 60, 72, 96, 120, 144, or 168 hours, for example.

In some aspects, a non-native glucosyltransferase only differs from a second glucosyltransferase at the substitution position(s) as disclosed herein, and the alpha-1,3 branching activity of the non-native glucosyltransferase is about, at least about, or no more than about, 25%, 30%, 40%, 50%, 60%, 70%, 80%, 90%, 110%, 125%, 150%, 175%, 200%, 225%, 250%, 275%, 300%, 325%, 25%-90%, 25%-70%, 25-50%, 110%-325%, 110%-250%, 110-200%, 125%-325%, 125%-250%, 125-200%, 150%-325%, 150%-250%, or 150-200% of the alpha-1,3 branching activity of the second glucosyltransferase. Alpha-1,3 branching activity determinations for such a comparison can be as described in Vuillemin et al. (2016, *J. Biol. Chem.* 14:7687-7702) or Remaud-Simeon et al. (U.S. Patent Appl. Publ. No. 2016/0136199) (both references incorporated herein by reference), or with respect to any branching reaction/process as disclosed herein (e.g., taking into account initial sucrose conc., acceptor, temperature, pH, and/or reaction time), and using any suitable measurement technique. Typically, a comparison between non-native and second glucosyltransferases herein is made under identical or similar reaction conditions.

A glucan composition comprising at least one alpha-1,3 branch is produced in an alpha-1,3-branched glucan synthesis method herein. In some aspects, such a product comprises about, or at least about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 1-50%, 1-40%, 1-30%, 1-20%, 1-10%, 1-5%, 5-50%, 5-40%, 5-30%, 5-20%, or 5-10% alpha-1,3 branches. This percentage level can be either that of newly added alpha-1,3 branches (e.g., as that achieved when using dextran with no pre-existing alpha-1,3 branches as an acceptor), or a total of newly added alpha-1,3 branches plus any pre-existing alpha-1,3 branches. An alpha-1,3-branched glucan product herein typically is soluble, but can be insoluble in some aspects.

A glucan composition comprising at least one alpha-1,3 branch produced in a method herein can optionally be isolated. In certain embodiments, isolating such a product can include at least conducting a step of centrifugation, filtration, fractionation, chromatographic separation, dialysis, evaporation, precipitation, and/or dilution. Some of these steps are more relevant for isolating a soluble product, while some are more relevant for isolating an insoluble product. Isolation in some aspects can optionally further comprise washing the product one, two, or more times with water or another suitable fluid (e.g., 70-95 wt % ethanol), depending on the solubility profile of the product. A wash volume can optionally be at least about 10-100% of the volume of the reaction composition used to produce the branched product. Isolation herein can optionally further comprise drying the branched product, and/or preparing an aqueous dispersion of the product if it is insoluble.

Any of the disclosed conditions for synthesizing an alpha-1,3-branched glucan product, such as the foregoing or those described in the below Examples, can be applied to practicing a reaction composition as presently disclosed (and vice versa), and/or used to characterize features/activity of a non-native glucosyltransferase, accordingly.

In some aspects, an alpha-1,3-branched glucan product that has been isolated (optionally characterized as "purified") can be present in a composition at a wt % (e.g., dry weight basis) of at least about 50%, 60%, 70%, 80%, 85%, 90%, 91%, 92%, 93%, 94%, 95%, 96%, 97%, 98%, 98.5%, 99%, 99.5%, 99.8%, or 99.9%. Such isolated product can be used as an ingredient/component in a product/application, for example.

The present disclosure also concerns a method of preparing a polynucleotide sequence encoding a non-native glucosyltransferase herein. This method comprises:

(a) identifying a polynucleotide sequence encoding a parent glucosyltransferase that (i) comprises an amino acid sequence that is at least about 40% identical to SEQ ID NO:3 or positions 477-1322 of SEQ ID NO:2, and (ii) is capable of forming at least one alpha-1,3 branch from an acceptor molecule; and (b) modifying the polynucleotide sequence identified in step (a) to substitute at least one amino acid of the parent glucosyltransferase at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, thereby providing a polynucleotide sequence encoding a non-native glucosyltransferase that forms at least one alpha-1,3 branch from an acceptor molecule.

Such a method can optionally further comprise using a polynucleotide prepared in this manner in a method of expressing the non-native glucosyltransferase encoded by the polynucleotide. Such an expression method can follow any heterologous protein expression method as known in the art, for example. The present method of preparing a polynucleotide can optionally alternatively be characterized as a method of modifying the branching activity of an alpha-1,3-branching enzyme.

A parent glucosyltransferase enzyme herein can comprise an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:3 or positions 477-1322 of SEQ ID NO:2, for example. It is noted simply for reference purposes that SEQ ID NO:3 and positions 477-1322 of SEQ ID NO:2 are subsequences of SEQ ID NO:4.

Identification step (a) herein can, in some instances, comprise identifying an amino acid sequence of a parent glucosyltransferase enzyme. A polynucleotide sequence can be determined from this amino acid sequence according to the genetic code (codons), such as the genetic code used in the species from which the parent glucosyltransferase was identified.

Identifying a polynucleotide encoding a parent glucosyltransferase herein can be performed (a) in silico, (b) with a method comprising a nucleic acid hybridization step, (c) with a method comprising a protein sequencing step, and/or (d) with a method comprising a protein binding step, for example.

Regarding in silico detection, the amino acid sequences of candidate parent glucosyltransferase enzymes (and/or nucleotide sequences encoding such glucosyltransferase enzymes) stored in a computer or database (e.g., public databases such as GENBANK, EMBL, REFSEQ, GENE-PEPT, SWISS-PROT, PIR, PDB) can be reviewed in silico to identify a glucosyltransferase enzyme comprising an amino acid sequence with a percent sequence identity as described above for a parent glucosyltransferase. Such review could comprise using any means known in the art such as through use of an alignment algorithm or software as described above (e.g., BLASTN, BLASTP, ClustalW, ClustalV, Clustal-Omega, EMBOSS).

Identifying a parent glucosyltransferase as disclosed above can optionally be performed via a method comprising a nucleic acid hybridization step. Such a method can comprise using DNA hybridization (e.g., Southern blot, dot blot), RNA hybridization (e.g., northern blot), or any other method that has a nucleic acid hybridization step (e.g., DNA sequencing, PCR, RT-PCR, all of which may comprise hybridization of an oligonucleotide), for example. A polynucleotide sequence encoding SEQ ID NO:3 or a subsequence thereof (e.g., positions 477-1322 of SEQ ID NO:2) can be used as a probe, for example, in such a hybridization. Conditions and parameters for carrying out hybridization methods in general are well known and disclosed, for example, in Sambrook J, Fritsch E F and Maniatis T, *Molecular Cloning: A Laboratory Manual*, Cold Spring Harbor Laboratory: Cold Spring Harbor, NY (1989); Silhavy T J, Bennan M L and Enquist L W, *Experiments with Gene Fusions*, Cold Spring Harbor Laboratory: Cold Spring Harbor, NY (1984); Ausubel F M et al., Current Protocols in Molecular Biology, published by Greene Publishing Assoc. and Wiley-Interscience, Hoboken, NJ (1987); and Innis M A, Gelfand D H, Sninsky J J and White T J (Editors), *PCR Protocols: A Guide to Methods and Applications*, Academic Press, Inc., San Diego, CA (1990).

Identifying a parent glucosyltransferase as disclosed above can optionally be performed via a method comprising a protein sequencing step. Such a protein sequencing step can comprise one or more procedures such as N-terminal amino acid analysis, C-terminal amino acid analysis, Edman degradation, or mass spectrometry, for example.

Identifying a parent glucosyltransferase as disclosed above can optionally be performed via a method comprising a protein binding step. Such a protein binding step can be performed using an antibody that binds to a motif or epitope within SEQ ID NO:3 (e.g., within positions 477-1322 of SEQ ID NO:2), for example.

A polynucleotide identified in step (a) (i.e., before its modification in step [b]) can, in some aspects, encode a glucosyltransferase comprising an amino acid sequence that is identical to, or at least 90%, 91%, 92%, 93%, 94%, 95%, 96%, 97%, 98%, 99%, or 99.5% identical to, the amino acid sequence of any glucosyltransferase disclosed in Table 1. An alpha-glucan as produced by such a glucosyltransferase can be as disclosed herein, for example.

A method of preparing a polynucleotide sequence encoding a non-native glucosyltransferase herein comprises step (b) of modifying the polynucleotide sequence (encoding a parent glucosyltransferase) identified in step (a). Such modification substitutes at least one amino acid of the parent glucosyltransferase at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4. The non-native glucosyltransferase (encoded by the modified polynucleotide sequence) resulting from such one or more substitutions can be optionally be characterized as a "child glucosyltransferase" herein.

A suitable modification of a polynucleotide in step (b) can be made following any DNA manipulation technique known in the art. Modifying step (b) can optionally be performed in silico, followed by synthesis of the polynucleotide sequence encoding a non-native glucosyltransferase. For example, a polynucleotide sequence identified in step (a) can be manipulated in silico using a suitable sequence manipulation program/software (e.g., VECTOR NTI, LIFE TECHNOLOGIES, Carlsbad, CA; DNAStrider; DNASTAR, Madison, WI). Following such virtual manipulation, the modified polynucleotide sequence can be artificially synthesized by any suitable technique (e.g., annealing-based connection of oligonucleotides, or any technique disclosed in Hughes et al., *Methods Enzymol.* 498:277-309, which is incorporated herein by reference). It should be appreciated that the foregoing methodology is not believed to necessarily rely on having a pre-existing polynucleotide (encoding a parent glucosyltransferase) in hand.

Modifying step (b) can optionally be performed using a physical copy of a polynucleotide sequence identified in step (a) encoding a parent glucosyltransferase. As an example, such a polynucleotide can serve as a template for amplification using primers designed in a manner such that the amplified product encodes a non-native glucosyltransferase herein (e.g., refer to Innis et al., ibid.).

The amino acid substitutions in this method can be one or more substitutions as disclosed herein. Essentially any non-native glucosyltransferase as presently disclosed can be encoded by a polynucleotide as prepared by this method, for instance.

Non-limiting examples of compositions and methods disclosed herein include:

1. A non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, wherein the non-native glucosyltransferase is capable of forming at least one alpha-1,3 branch from an acceptor molecule.

2. The non-native glucosyltransferase of embodiment 1, wherein: the amino acid substitution at the position corresponding with amino acid residue Ser-734 is with a Cys, Asp, Gly, His, Lys, Leu, Met, Asn, Thr, or Val residue; the amino acid substitution at the position corresponding with amino acid residue Ile-735 is with an Ala, Leu, or Val residue; the amino acid substitution at the position corresponding with amino acid residue Ile-737 is with an Ala, Cys, Asp, Gly, His, Leu, Met, Asn, Ser, Val, Trp, or Tyr residue; the amino acid substitution at the position corresponding with amino acid residue Ile-740 is with an Ala, Leu, or Val residue; the amino acid substitution at the position corresponding with amino acid residue Asp-744 is with an Ala, Cys, Glu, Phe, Gly, His, Lys, Met, Asn, Pro, Gln, Arg, Ser, Thr, Val, Trp, or Tyr residue; the amino acid substitution at the position corresponding with amino acid residue His-771 is with an Ala residue; the amino acid substitution at the position corresponding with amino acid residue Val-772 is with an Ala or Leu residue; the amino acid substitution at the position corresponding with amino acid residue Ser-773 is with an Ala or Asn residue; the amino acid substitution at the position corresponding with amino acid residue Val-775 is with an Ala residue; the amino acid substitution at the position corresponding with amino acid residue Ser-778 is with a Trp residue; the amino acid substitution at the position corresponding with amino acid residue Ala-779 is with an Asp, Gly, or Ser residue; the amino acid substitution at the position corresponding with amino acid residue Asp-780 is with an Ala, Gln, or Tyr residue; the amino acid substitution at the position corresponding with amino acid residue Ile-845 is with an Ala or Phe residue; the amino acid substitution at the position corresponding with amino acid residue Val-846 is with an Ala, Ile, or Thr residue; the amino acid substitution at the position corresponding with amino acid residue Asp-852 is with an Ala, Glu, Leu, or Asn residue; the amino acid substitution at the position corresponding with amino acid residue Ile-853 is with a Val residue; the amino acid substitution at the position corresponding with amino acid residue Asp-855 is with an Ala, Gly, or Ser residue; the amino acid substitution at the position corresponding with amino acid residue Ser-858 is with an Ala, Gly, Gln, or Arg residue; the amino acid substitution at the position corresponding with amino acid residue Asn-859 is with an Ala, Asp, Glu, Lys, Ser, or Thr residue; the amino acid substitution at the position corresponding with amino acid residue Ala-1232 is with a Cys, Asp, Glu, Phe, Gly, His, Leu, Met, Asn, Pro, Gln, Ser, Thr, Val, or Tyr residue; the amino acid substitution at the position corresponding with amino acid residue Tyr-1234 is with a Cys, Glu, His, Leu, Met, Thr, Val, or Trp residue; and/or the amino acid substitution at the position corresponding with amino acid residue Asn-1237 is with an Asp or Gly residue.

3. The non-native glucosyltransferase of embodiment 1 or 2, comprising two or more amino acid substitutions, wherein at least one of the substitutions is at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4.

4. The non-native glucosyltransferase of embodiment 1,2, or 3, wherein at least one of the substitutions is at a position corresponding with amino acid residue Ser-734, Ile-735, Ser-778, Asp-780, Ile-845, Asp-852, Ile-853, Asp-855, Ala-1232, or Tyr-1234 of SEQ ID NO:4, optionally wherein: the amino acid substitution at the position corresponding with amino acid residue Ser-734 is with a Cys residue; the amino acid substitution at the position corresponding with amino acid residue Ile-735 is with a Val residue; the amino acid substitution at the position corresponding with amino acid residue Ser-778 is with a Trp residue; the amino acid substitution at the position corresponding with amino acid residue Asp-780 is with a Tyr residue; the amino acid substitution at the position corresponding with amino acid residue Ile-845 is with a Phe residue; the amino acid substitution at the position corresponding with amino acid residue Asp-852 is with a Glu residue; the amino acid substitution at the position corresponding with amino acid residue Ile-853 is with a Val residue; the amino acid substitution at the position corresponding with amino acid residue Asp-855 is with a Gly residue; the amino acid substitution at the position corresponding with amino acid residue Ala-1232 is with a Gly, Met, Ser, or Val residue; and/or the amino acid substitution at the position corresponding with amino acid residue Tyr-1234 is with a Trp residue.

5. The non-native glucosyltransferase of embodiment 1, 2, 3, or 4, wherein the acceptor molecule comprises glucan.

6. The non-native glucosyltransferase of embodiment 5, wherein the glucan is soluble glucan.

7. The non-native glucosyltransferase of embodiment 5 or 6, wherein the glucan comprises alpha-glucan.

8. The non-native glucosyltransferase of embodiment 7, wherein the alpha-glucan comprises dextran.

9. The non-native glucosyltransferase of embodiment 1, 2, 3, 4, 5, 6, 7, or 8, wherein the non-native glucosyltransferase only differs from a second glucosyltransferase at the substitution position(s), wherein the alpha-1,3 branching activity of the non-native glucosyltransferase is at least about 50% of the alpha-1,3 branching activity of the second glucosyltransferase.

10. The non-native glucosyltransferase of embodiment 1, 2, 3, 4, 5, 6, 7, 8, or 9, wherein the non-native glucosyltransferase only differs from a second glucosyltransferase at the substitution position(s), wherein the second glucosyltransferase comprises the motifs of: (i) an amino acid sequence that is at least 80% identical to SEQ ID NO:9, (ii) an amino acid sequence that is at least 80% identical to SEQ ID NO:10, (iii) an amino acid sequence that is at least 80% identical to SEQ ID NO:11, and (iv) an amino acid sequence that is at least 80% identical to SEQ ID NO:12.

11. The non-native glucosyltransferase of embodiment 1, 2, 3, 4, 5, 6, 7, 8, 9, or 10, wherein the non-native glucosyltransferase comprises an amino acid sequence that is at least about 90% identical to: residues 477-1322 of SEQ ID NO:2, or residues 446-1313 of SEQ ID NO:13.

12. The non-native glucosyltransferase of embodiment 1, 2, 3, 4, 5, 6, 7, 8, 9, 10, or 11, wherein the non-native glucosyltransferase comprises an amino acid sequence that is at least about 90% identical to SEQ ID NO:2, 3, or 15.

13. A polynucleotide comprising a nucleotide sequence encoding a non-native glucosyltransferase according to embodiment 1, 2, 3, 4, 5, 6, 7, 8, 9, 10, 11, or 12, optionally wherein one or more regulatory sequences are operably linked to the nucleotide sequence, and preferably wherein the one or more regulatory sequences include a promoter sequence.

14. A reaction composition comprising water, sucrose, an acceptor molecule, and a non-native glucosyltransferase according to embodiment 1, 2, 3, 4, 5, 6, 7, 8, 9, 10, 11, or 12.

15. The reaction composition of embodiment 14, wherein the acceptor molecule comprises glucan, optionally wherein: (i) the glucan is soluble glucan, and/or (ii) the glucan comprises alpha-glucan, preferably wherein the alpha-glucan comprises dextran.

16. A method of producing a glucan composition that comprises at least one alpha-1,3 branch, the method comprising: (a) contacting at least water, sucrose, a glucan substrate, and a non-native glucosyltransferase enzyme according to embodiment 1, 2, 3, 4, 5, 6, 7, 8, 9, 10, 11, or 12, whereby a glucan composition comprising at least one alpha-1,3 branch is produced; and (b) optionally isolating the glucan composition produced in step (a). 16b. A glucan composition produced by (i) a reaction composition of embodiment 14 or 15, or (ii) a method of embodiment 16.

17. A method of preparing a polynucleotide sequence encoding a non-native glucosyltransferase, the method comprising: (a) identifying a polynucleotide sequence encoding a parent glucosyltransferase that (i) comprises an amino acid sequence that is at least about 40% identical to SEQ ID NO:3 or positions 477-1322 of SEQ ID NO:2, and (ii) is capable of forming at least one alpha-1,3 branch from an acceptor molecule; and (b) modifying the polynucleotide sequence identified in step (a) to substitute at least one amino acid of the parent glucosyltransferase at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, thereby providing a polynucleotide sequence encoding a non-native glucosyltransferase that forms at least one alpha-1,3 branch from an acceptor molecule.

18. The method of embodiment 17, wherein the identifying step is performed: (a) in silico, (b) with a method comprising a nucleic acid hybridization step, (c) with a method comprising a protein sequencing step, and/or (d) with a method comprising a protein binding step; and/or wherein the modifying step is performed: (e) in silico, followed by synthesis of the polynucleotide sequence encoding the non-native glucosyltransferase enzyme, or (f) using a physical copy of the polynucleotide sequence encoding the parent glucosyltransferase.

EXAMPLES

The present disclosure is further exemplified in the below Examples. It should be understood that these Examples, (encoded by SEQ ID NO:1). This enzyme can add branches to a glucan substrate such as dextran via alpha-1,3-glycosidic linkage; each branch is typically a pendant glucose. GTF 2592 essentially is an N-terminally truncated version (all of signal peptide removed) of a full-length (immature) wild type alpha-1,3-branching glucosyltransferase (represented by SEQ ID NO:4) from *Leuconostoc fallax*. In addition to having an N-terminal truncation, GTF 2592 (SEQ ID NO:2) has a C-terminal polyhistidine (6×His) tag. GTF 2592 (SEQ ID NO:2) corresponds structurally and functionally with SEQ ID NO:3, which is GTF 2592 without a start methionine and 6×His tag. Amino acid substitutions made in GTF 2592 (SEQ ID NO:2) can be characterized as substituting for native amino acid residues, as each amino acid residue/position of SEQ ID NO:2 (apart from the Met-1 residue and C-terminal 6×His tag of SEQ ID NO:2) corresponds accordingly with an amino acid residue/position within SEQ ID NO:4.

GTF 2592 contains four motifs (I-IV), which are listed in Table 2 below. These motifs are conserved with respect to other alpha-1,3-branching glucosyltransferases (refer to Vuillemin et al., 2016, *J. Biol. Chem.* 14:7687-7702; U.S. Patent Appl. Publ. No. 2016/0136199; both incorporated herein by reference). The amino acid substitutions in this Example were made at various positions within each of these motifs in GTF 2592.

TABLE 2

| | | | | Position in full-length wild |
|---|---|---|---|---|
| | | SEQ | Position in GTF 2592 | type version of GTF 2592 |
| Motif | Sequence | ID NO. | (SEQ ID NO: 2) | (SEQ ID NO: 4) |
| II | SIRIDAISFVD | 6 | 696-706 | 734-744 |
| III | HVSIVEASADQ | 7 | 733-743 | 771-781 |
| IV | IVHAHDKDIQDAVSN | 8 | 807-821 | 845-859 |
| I | ADYVANQ | 5 | 1194-1200 | 1232-1238 |

Conserved Motifs of GTF 2592 while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Analysis of Amino Acid Sites Affecting Activity of Alpha-1,3-Branching Enzyme This Example describes screening alpha-1,3-branching glucosyltransferase variants for alpha-1,3-branching activity. In particular, enzyme variants containing single amino acid substitutions in conserved motifs were tested for alpha-1,3-branching activity on a dextran substrate. Several alpha-1,3-branching glucosyltransferase variants were identified to have either similar or enhanced alpha-1,3-branching activity as compared to a non-amino acid-substituted control enzyme.

The amino acid sequence of the alpha-1,3-branching glucosyltransferase to which amino acid substitutions were made in this Example was SEQ ID NO:2 (GTF 2592)

It is noted that amino acid residues 477-1322 of GTF 2592 (SEQ ID NO:2) align with (by conducting a CLUSTAL OMEGA alignment, data not shown) the entire amino acid sequence of a fragment (BRS-B-M) of the *Leuconostoc citreum* alpha-1,3-branching enzyme, BRS-B. BRS-B-M (SEQ ID NO:14), which represents residues 446-1313 of BRS-B (SEQ ID NO:13), is disclosed by Vuillemin et al. (ibid.) to have branching activity similar to that of BRS-B. It is therefore contemplated that proteins comprising amino acid residues 477-1322 of GTF 2592 (SEQ ID NO:2 or 3) or related sequences (e.g., with at least 90% identity to amino acid residues 477-1322 of GTF 2592) have alpha-1,3-branching activity that is the same or similar to that of GTF 2592 (SEQ ID NO:2). SEQ ID NO:15 is the mature (no signal peptide) counterpart of the BRS-B of SEQ ID NO:13.

Nucleic acid mutations for encoding each amino acid substitution were individually prepared through PCR-based mutagenesis. Briefly, a DNA fragment containing an individual mutation was produced through a typical PCR reaction using GTF 2592-encoding DNA (SEQ ID NO:1) as template, an appropriate forward primer encoding the mutation, and an appropriate shared reverse primer (sequences not shown). The DNA fragment was then used to produce a DNA encoding a single amino acid-substituted version of GTF 2592 using the QuikChange® Lightning™ Site-Directed Mutagenesis Kit (AGILENT, cat. no. 210518) following the manufacturer's protocol.

Plasmids (pBAD vector, THERMO FISHER SCIENTIFIC) for individually expressing GTF 2592 (pBAD-GTF2592) and each single amino acid-substituted variant thereof were prepared in *E. coli* Bw25113 (ΔilvC), which is a derivative of the F⁻, λ⁻, *E. coli* K-12 strain BD792 (CGSC6159) with one additional knock-out, ΔilvC. The resulting plasmids encoding single amino acid-substituted enzymes were sequenced to verify each substitution. LB agar plates with 100 mg/L ampicillin were used to select transformants.

To produce GTF 2592 (SEQ ID NO:2) and single amino acid-substituted variants thereof, *E. coli* Bw25113 transformed with pBAD-GTF2592 or mutated versions thereof were cultivated in LB media with 100 mg/L ampicillin at 37° C. After the $OD_{600}$ of each culture reached 0.8, L-arabinose was added to a final concentration of 0.025% and then the cultures were grown at 18° C. overnight. The cells were then harvested and lysed with a 5% culture volume of B-PER™ (THERMO FISHER SCIENTIFIC) at room temperature for about 1 hour. Lysed cells were centrifuged to remove cell debris and the resultant supernatants were used in alpha-1, 3-branching reactions (below).

Individual reactions were conducted to test the alpha-1, 3-branching activity of each enzyme (GTF 2592 [SEQ ID NO:2] or a single amino acid-substituted variant thereof) on a dextran substrate. Dextran for this study was obtained from Sigma-Aldrich (cat. no. D1662, "Dextran from *Leuconostoc mesenteroides*", average mol. wt. of 35000-45000, about 95% alpha-1,6 linkages). Each branching reaction was prepared comprising dextran, sucrose, water and an enzyme as prepared above, and conducted with parameters that were the same as, or similar to, the following: vessel, 96-deep well plates agitated at 300 rpm; initial pH, 5.5; reaction volume, 0.8 mL; sucrose, 50 g/L; dextran, 50 g/L; GTF, 0.0875 mL of lysate of *E. coli* cells heterologously expressing enzyme; sodium acetate, 50 mM, pH 5.5; temperature, 30° C.; time, about two days. The reactions were then heat de-activated at 80° C. for 30 minutes. The resulting products were harvested and analyzed for alpha-1,3-linked branches by NMR. The branching activity of each single amino acid-substituted variant enzyme was normalized against the branching activity of GTF 2592 (SEQ ID NO:2), and is shown in Table 3 below.

TABLE 3

Alpha-1,3-Branching Activity of Single Amino Acid-Substituted Variants of GTF 2592 (SEQ ID NO: 2)

| Motif[d] no sub. | GTF[a] 2592[b] | Activity (%)[c] 100 |
|---|---|---|
| II | S734C | 154 |
| | S734D | 67 |
| | S734G | 86 |
| | S734H | 87 |
| | S734I | 14 |
| | S734K | 45 |
| | S734L | 100 |
| | S734M | 146 |
| | S734N | 154 |
| | S734P | 4 |
| | S734R | 4 |
| | S734T | 100 |
| | S734V | 100 |
| | S734W | 7 |
| | S734Y | 12 |
| | I735A | 247 |

TABLE 3-continued

Alpha-1,3-Branching Activity of Single Amino Acid-Substituted Variants of GTF 2592 (SEQ ID NO: 2)

| Motif[d] no sub. | GTF[a] 2592[b] | Activity (%)[c] 100 |
|---|---|---|
| | I735L | 309 |
| | I735V | 299 |
| | I737A | 46 |
| | I737C | 53 |
| | I737D | 51 |
| | I737E | 3 |
| | I737G | 39 |
| | I737H | 67 |
| | I737L | 43 |
| | I737M | 63 |
| | I737N | 86 |
| | I737R | — |
| | I737S | 33 |
| | I737T | 23 |
| | I737V | 107 |
| | I737W | 59 |
| | I737Y | 142 |
| | I740A | 259 |
| | I740L | 161 |
| | 1740V | 85 |
| | D744A | 111 |
| | D744C | 102 |
| | D744E | 114 |
| | D744F | 85 |
| | D744G | 114 |
| | D744H | 220 |
| | D744K | 102 |
| | D744M | 82 |
| | D744N | 173 |
| | D744P | 230 |
| | D744Q | 205 |
| | D744R | 170 |
| | D744S | 140 |
| | D744T | 190 |
| | D744V | 126 |
| | D744W | 51 |
| | D744Y | 189 |
| III | H771A | 81 |
| | V772A | 107 |
| | V772L | 101 |
| | S773A | 57 |
| | S773N | 189 |
| | V775A | 79 |
| | S778W | 116 |
| | A779D | 49 |
| | A779G | 133 |
| | A779S | 30 |
| | D780A | 161 |
| | D780Q. | 137 |
| | D780Y | 163 |
| IV | I845A | 37 |
| | I845F | 50 |
| | V846A | 96 |
| | V846I | 137 |
| | V846T | 94 |
| | H847R | 15 |
| | D852A | 103 |
| | D852E | 62 |
| | D852L | 97 |
| | D852N | 84 |
| | 1853V | 92 |
| | D855A | 101 |
| | D855G | 119 |
| | D855S | 39 |
| | S858A | 186 |
| | S858G | 124 |
| | S858Q | 136 |
| | S858R | 142 |
| | N859A | 70 |
| | N859D | 125 |
| | N859E | 252 |
| | N859K | 95 |
| | N859S | 283 |
| | N859T | 262 |

TABLE 3-continued

Alpha-1,3-Branching Activity of Single Amino Acid-Substituted
Variants of GTF 2592 (SEQ ID NO: 2)

| Motif[d]<br>no sub. | GTF[a]<br>2592[b] | Activity (%)[c]<br>100 |
|---|---|---|
| I | A1232C | 173 |
| | A1232D | 143 |
| | A1232E | 40 |
| | A1232F | 207 |
| | A1232G | 177 |
| | A1232H | 144 |
| | A1232K | 1 |
| | A1232L | 140 |
| | A1232M | 152 |
| | A1232N | 163 |
| | A1232P | 58 |
| | A1232Q | 63 |
| | A1232S | 200 |
| | A1232T | 146 |
| | A1232V | 183 |
| | A1232Y | 59 |
| | Y1234C | 168 |
| | Y1234E | 80 |
| | Y1234H | 36 |
| | Y1234L | 148 |
| | Y1234M | 51 |
| | Y1234P | 18 |
| | Y1234T | 50 |
| | Y1234V | 103 |
| | Y1234W | 204 |
| | N1237D | 59 |
| | N1237F | — |
| | N1237G | 89 |
| | N1237I | 3 |
| | N1237L | 8 |

[a]Each listed GTF with a substitution is a version of GTF 2592 comprising a substitution at a respective position, where the position number corresponds with the residue numbering of SEQ ID NO: 4 (full-length wild type version of GTF 2592). The wild type residue is listed first (before residue position number) and the substituting residue is listed second (after the residue position number) (this "wild type residue-position number-variant residue" annotation format applies throughout the present disclosure).
[b]GTF 2592, SEQ ID NO: 2. No amino acid substitutions (control).
[c]Percent alpha-1,3-branching activity with respect to the alpha-1,3-branching activity measured for control (GTF 2592 with no substitutions).
[d]The conserved motif in which the single amino acid substitution is located. Table 2 lists the locations of each of conserved motifs I-IV in GTF 2592.

Based on the data in Table 3, it appears that alpha-1,3-branching glucosyltransferases such as GTF 2592 retain most or all of their activity when modified with various single amino acid substitutions. Several amino acid substitutions enhanced this activity.

Example 2

Analysis of the Effects of Two or More Amino Acid Substitutions on Alpha-1,3-Branching Enzyme Activity This Example describes introducing multiple amino acid substitutions to an alpha-1,3-branching glucosyltransferase enzyme and determining their effect on alpha-1,3-branching activity. Various combinations of amino acid substitutions were identified that allowed similar alpha-1,3-branching activity of variant enzymes as compared to a non-amino acid-substituted control enzyme.

The amino acid sequence of the alpha-1,3-branching glucosyltransferase to which amino acid substitutions were made in this Example was SEQ ID NO:2 (GTF 2592) (encoded by SEQ ID NO:1), as in Example 1. Briefly, using the site-directed mutagenesis and enzyme expression techniques described above, enzymes were produced having multiple amino acid substitutions in (i) one of conserved motifs I-IV, or (ii) across all four of conserved motifs I-IV. Each variant enzyme was entered into a branching reaction with parameters that were the same as those described in Example 1, and products of these reactions were analyzed in the same manner. The branching activity of each multiple amino acid-substituted variant enzyme was normalized against the branching activity of GTF 2592 (SEQ ID NO:2), and is shown in Tables 4 and 5 below.

TABLE 4

Alpha-1,3-Branchinq Activity of Variants of GTF 2592 (SEQ ID NO: 2) Having Multiple Amino Acid Substitutions in One of Conserved Motifs I-IV

| Motif[d]<br>no sub. | GTF[a]<br>2592[b] | Activity (%)[c]<br>100 |
|---|---|---|
| II | S734G/I737V | 94 |
| | S734G/I737V/D744T | 57 |
| | S734G/I737V/D744N | 58 |
| | S734G/I737V/D744S | 53 |
| III | H771A/D780A | 30 |
| | V772L/Q781D | 66 |
| | S773N/D780A | 61 |
| | S773N/D780Q | 99 |
| | S773N/D780Y | 53 |
| | S773N/D780O/0781D | 52 |
| | S773N/D780Y/Q781D | 32 |
| | A779G/D780Y/Q781D | 60 |
| | A779D/D780O/0781D | 95 |
| | A779D/D780Y/Q781D | 55 |
| | A779D/D780A/Q781D | 17 |
| IV | I845F/D852E/I853V/D855G | 44 |
| | I845F/D852E/V857I | 76 |
| | 845F/D852A/V857L | 42 |
| | I845F/D852E/V857L | 69 |
| | I845F/V857 | 97 |
| I | A1232V/Y1234W | 103 |
| | A1232M/Y1234W | 95 |
| | A1232S/Y1234W | 59 |
| | A1232G/Y1234W | 49 |
| | A1232D/N1237G | 82 |
| | A1232G/N1237G | 91 |
| | A1232G/N1237D | 51 |
| | A1232S/N1237D | 50 |
| | A1232V/N1237G | 86 |
| | A1232V/N1237D | 81 |
| | A1232V/Y1234W | 103 |
| | A1232M/Y1234W | 95 |
| | A1232S/Y1234W | 59 |
| | A1232G/Y1234W | 49 |

[a]Each listed GTF with substitutions is a version of GTF 2592 comprising substitutions at respective positions, where each position number corresponds with the residue numbering of SEQ ID NO: 4 (full-length wild type version of GTF 2592).
[b]GTF 2592, SEQ ID NO: 2. No amino acid substitutions (control).
[c]Percent alpha-1,3-branching activity with respect to the alpha-1,3 branching activity measured for control (GTF 2592 with no substitutions),
[d]The conserved motif in which amino acid substitutions are located. Table 2 lists the locations of each of conserved motifs I-IV in GTF 2592.

TABLE 5

Alpha-1,3-Branching Activity of Variants of GTF 2592 (SEQ ID NO: 2) Having Multiple Amino Acid
Substitutions in More than One of Conserved Motifs I-IV

| GTF 2592[a] GTF[b] | | | | Activity (%)[c] |
| --- | --- | --- | --- | --- |
| Motif II | Motif III | Motif IV | Motif I | 100 |
| I735L | D780Y | I845F/D852E/I853V/D855G | A1232G/Y1234W | 62 |
| I735L | D780Y | I845F/D852E/I853V/D855G | A1232M/Y1234W | 112 |
| I735L | D780Y | I845F/D852E/I853V/D855G | A1232S/Y1234W | 55 |
| I735V | D780Y | I845F/D852E/I853V/D855G | A1232G/Y1234W | 100 |
| I735V | D780Y | I845F/D852E/I853V/D855G | A1232M/Y1234W | 56 |
| I735V | D780Y | I845F/D852E/I853V/D855G | A1232V/Y1234W | 67 |
| I735V | D780Y | I845F/D852E/I853V/D855G | A1232V/N1237G | 32 |
| S734C | D780Y | I845F/D852E/I853V/D855G | A1232V/Y1234W | 27 |
| S734C | S778W | I845F/D852E/I853V/D855G | A1232G/Y1234W | 124 |
| S734C | S778W | I845F/D852E/I853V/D855G | A1232G/Y1234W | 99 |
| S734C | S778W | I845F/D852E/I853V/D855G | A1232M/Y1234W | 67 |
| S734C | S778W | I845F/D852E/I853V/D855G | A1232S/Y1234W | 114 |
| S734C | S778W | I845F/D852E/I853V/D855G | A1232V/Y1234W | 100 |
| I735V | V775A/D780Y | I845F/D852E/I853V/D855G | A1232V/Y1234W | 63 |
| I735V | S778W/D780Y | I845F/D852E/I853V/D855G | A1232V/Y1234W | 53 |
| I735V | S778W/D780Y | I845F/D852E/I853V/D855G | A1232V/Y1234W | 57 |
| S734C | V775A/S778W/D780Y | I845F/D852E/I853V/D855G | A1232G/Y1234W | 13 |
| S734C/I735V | V775A/S778W | I845F/D852E/I853V/D855G | A1232V/Y1234W | 50 |
| S734C/I735V | V775A/S778W | I845F/D852E/I853V/D855G | A1232V/Y1234W | 63 |
| S734C/I735V | V775A/S778W/D780Y | I845F/D852E/I853V/D855G | A1232G/Y1234W | 31 |
| S734C/I735V | V775A/S778W/D780Y | I845F/D852E/I853V/D855G | A1232G/Y1234W | 61 |
| S734C/I735L/I740A | S778W/D780Y | I845F/D852E/I853V/D855G | A1232G/Y1234W | 25 |
| S734C/I735V/I740A | S778W/D780Y | I845F/D852E/I853V/D855G | A1232V/Y1234W | 13 |
| S734C/I735V/D744T | S778W/D780Y | I845F/D852E/I853V/D855G | A1232G/Y1234W | 20 |
| S734C/I735V/D744T | V775A/S778W/D780Y | I845F/D852E/I853V/D855G | A1232G/Y1234W | 23 |
| S734C/I735V/D744N | V775A/S778W/D780Y | I845F/D852E/I853V/D855G | A1232G/Y1234W | 42 |
| S734C/I735V/I740L | V775A/S778W/D780Y | I845F/D852E/I853V/D855G | A1232G/Y1234W | 80 |
| S734C/I735V/I740A | V775A/S778W/D780Y | I845F/D852E/I853V/D855G | A1232G/Y1234W | 24 |

[a]GTF 2592, SEQ ID NO: 2. No amino acid substitutions (control).
[b]Each following row represents a version of GTF 2592 comprising substitutions at respective positions, where each position number corresponds with the residue numbering of SEQ ID NO: 4 (full-length wild type version of GTF 2592). The substitutions in each enzyme are organized according to the motif (I-IV) in which they are located.
[c]Percent alpha-1,3-branching activity with respect to the alpha-1,3-branching activity measured for control (GTF 2592 with no substitutions).

Based on the data in Tables 4 and 5, it appears that alpha-1,3-branching glucosyltransferases such as GTF 2592 retain branching activity when modified to have multiple amino acid substitutions. Several of the substitution combinations could be useful for applications in which lower branching activity is desirable, for example.

What is claimed is:

1. A non-native glucosyltransferase comprising at least one amino acid substitution at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4, wherein the non-native glucosyltransferase is capable of forming at least one alpha-1,3 branch from an acceptor molecule, wherein said at least one alpha-1,3 branch consists of a single glucose unit, wherein the non-native glucosyltransferase comprises an amino acid sequence that shares at least 80% sequence identity with residues 477-1322 of SEQ ID NO:2, and wherein said amino acid sequence does not share 100% sequence identity with residues 477-1322 of SEQ ID NO:2.

2. The non-native glucosyltransferase of claim 1, wherein:

the amino acid substitution at the position corresponding with amino acid residue Ser-734 is with a Cys, Asp, Gly, His, Lys, Leu, Met, Asn, Thr, or Val residue;

the amino acid substitution at the position corresponding with amino acid residue Ile-735 is with an Ala, Leu, or Val residue;

the amino acid substitution at the position corresponding with amino acid residue Ile-737 is with an Ala, Cys, Asp, Gly, His, Leu, Met, Asn, Ser, Val, Trp, or Tyr residue;

the amino acid substitution at the position corresponding with amino acid residue Ile-740 is with an Ala, Leu, or Val residue;

the amino acid substitution at the position corresponding with amino acid residue Asp-744 is with an Ala, Cys, Glu, Phe, Gly, His, Lys, Met, Asn, Pro, Gln, Arg, Ser, Thr, Val, Trp, or Tyr residue;

the amino acid substitution at the position corresponding with amino acid residue His-771 is with an Ala residue;

the amino acid substitution at the position corresponding with amino acid residue Val-772 is with an Ala or Leu residue;

the amino acid substitution at the position corresponding with amino acid residue Ser-773 is with an Ala or Asn residue;

the amino acid substitution at the position corresponding with amino acid residue Val-775 is with an Ala residue;

the amino acid substitution at the position corresponding with amino acid residue Ser-778 is with a Trp residue;

the amino acid substitution at the position corresponding with amino acid residue Ala-779 is with an Asp, Gly, or Ser residue;

the amino acid substitution at the position corresponding with amino acid residue Asp-780 is with an Ala, Gln, or Tyr residue;

the amino acid substitution at the position corresponding with amino acid residue Ile-845 is with an Ala or Phe residue;

the amino acid substitution at the position corresponding with amino acid residue Val-846 is with an Ala, Ile, or Thr residue;

the amino acid substitution at the position corresponding with amino acid residue Asp-852 is with an Ala, Glu, Leu, or Asn residue;

the amino acid substitution at the position corresponding with amino acid residue Ile-853 is with a Val residue;

the amino acid substitution at the position corresponding with amino acid residue Asp-855 is with an Ala, Gly, or Ser residue;

the amino acid substitution at the position corresponding with amino acid residue Ser-858 is with an Ala, Gly, Gln, or Arg residue;

the amino acid substitution at the position corresponding with amino acid residue Asn-859 is with an Ala, Asp, Glu, Lys, Ser, or Thr residue;

the amino acid substitution at the position corresponding with amino acid residue Ala-1232 is with a Cys, Asp, Glu, Phe, Gly, His, Leu, Met, Asn, Pro, Gln, Ser, Thr, Val, or Tyr residue;

the amino acid substitution at the position corresponding with amino acid residue Tyr-1234 is with a Cys, Glu, His, Leu, Met, Thr, Val, or Trp residue; and/or the amino acid substitution at the position corresponding with amino acid residue Asn-1237 is with an Asp or Gly residue.

3. The non-native glucosyltransferase of claim 1, comprising two or more amino acid substitutions, wherein at least one of the substitutions is at a position corresponding with amino acid residue Ser-734, Ile-735, Ile-737, Ile-740, Asp-744, His-771, Val-772, Ser-773, Val-775, Ser-778, Ala-779, Asp-780, Ile-845, Val-846, Asp-852, Ile-853, Asp-855, Ser-858, Asn-859, Ala-1232, Tyr-1234, or Asn-1237 of SEQ ID NO:4.

4. The non-native glucosyltransferase of claim 3, wherein at least one of the substitutions is at a position corresponding with amino acid residue Ser-734, Ile-735, Ser-778, Asp-780, Ile-845, Asp-852, Ile-853, Asp-855, Ala-1232, or Tyr-1234 of SEQ ID NO:4.

5. The non-native glucosyltransferase of claim 1, wherein the acceptor molecule comprises glucan.

6. The non-native glucosyltransferase of claim 5, wherein the glucan is soluble glucan.

7. The non-native glucosyltransferase of claim 5, wherein the glucan comprises alpha-glucan.

8. The non-native glucosyltransferase of claim 7, wherein the alpha-glucan comprises dextran.

9. The non-native glucosyltransferase of claim 1, wherein the amino acid sequence of the non-native glucosyltransferase only differs from SEQ ID NO:2 at the substitution position(s), wherein the alpha-1,3 branching activity of the non-native glucosyltransferase is at least 50% of the alpha-1,3 branching activity of SEQ ID NO:2.

10. The non-native glucosyltransferase of claim 1, wherein the non-native glucosyltransferase comprises an amino acid sequence that shares at least 90% sequence identity with residues 477-1322 of SEQ ID NO:2.

11. The non-native glucosyltransferase of claim 1, wherein the non-native glucosyltransferase comprises an amino acid sequence that is at least 80% identical to SEQ ID NO:2.

12. A polynucleotide comprising a nucleotide sequence encoding a non-native glucosyltransferase according to claim 1.

13. A reaction composition comprising water, sucrose, an acceptor molecule, and a non-native glucosyltransferase according to claim 1.

14. The reaction composition of claim 13, wherein the acceptor molecule comprises dextran.

15. A method of producing a glucan composition that comprises at least one alpha-1,3 branch, the method comprising:

(a) contacting at least water, sucrose, a glucan substrate, and a non-native glucosyltransferase according to claim 1, whereby a glucan composition comprising at least one alpha-1,3 branch is produced; and (b) optionally isolating the glucan composition produced in step (a).

16. The polynucleotide of claim 12, wherein one or more regulatory sequences are operably linked to the nucleotide sequence.

17. The polynucleotide of claim 16, wherein said one or more regulatory sequences include a promoter sequence.

18. The non-native glucosyltransferase of claim 4, wherein:

the amino acid substitution at the position corresponding with amino acid residue Ser-734 is with a Cys residue;

the amino acid substitution at the position corresponding with amino acid residue Ile-735 is with a Val residue;

the amino acid substitution at the position corresponding with amino acid residue Ser-778 is with a Trp residue;

the amino acid substitution at the position corresponding with amino acid residue Asp-780 is with a Tyr residue;

the amino acid substitution at the position corresponding with amino acid residue Ile-845 is with a Phe residue;

the amino acid substitution at the position corresponding with amino acid residue Asp-852 is with a Glu residue;

the amino acid substitution at the position corresponding with amino acid residue Ile-853 is with a Val residue;

the amino acid substitution at the position corresponding with amino acid residue Asp-855 is with a Gly residue;

the amino acid substitution at the position corresponding with amino acid residue Ala-1232 is with a Gly, Met, Ser, or Val residue; and/or the amino acid substitution at the position corresponding with amino acid residue Tyr-1234 is with a Trp residue.

* * * * *